United States Patent
Bierman et al.

(10) Patent No.: US 8,956,327 B2
(45) Date of Patent: Feb. 17, 2015

(54) ACCESS DEVICE

(75) Inventors: Steven F. Bierman, Del Mar, CA (US); Richard A. Pluth, San Diego, CA (US)

(73) Assignee: Access Scientific, LLC, San Diego, CA (US)

( * ) Notice: Subject to any disclaimer, the term of this patent is extended or adjusted under 35 U.S.C. 154(b) by 28 days.

(21) Appl. No.: 13/577,653

(22) PCT Filed: Feb. 8, 2011

(86) PCT No.: PCT/US2011/024097
§ 371 (c)(1),
(2), (4) Date: Aug. 7, 2012

(87) PCT Pub. No.: WO2011/097639
PCT Pub. Date: Aug. 11, 2011

(65) Prior Publication Data
US 2012/0316500 A1     Dec. 13, 2012

Related U.S. Application Data

(60) Provisional application No. 61/302,486, filed on Feb. 8, 2010.

(51) Int. Cl.
*A61M 5/178* (2006.01)
*A61M 25/06* (2006.01)
(Continued)

(52) U.S. Cl.
CPC ........... *A61M 25/0662* (2013.01); *A61M 29/00* (2013.01); *A61M 39/06* (2013.01); *A61M 25/0693* (2013.01); *A61M 2039/062* (2013.01)
USPC ..................................................... 604/164.1

(58) Field of Classification Search
CPC .................... A61M 2039/062; A61M 25/0662; A61M 25/0693; A61M 29/00; A61M 39/06
USPC ........................................ 604/164.01–167.06
See application file for complete search history.

(56) References Cited

U.S. PATENT DOCUMENTS

| 3,565,074 A | 2/1971 | Foti et al. |
| 4,068,659 A | 1/1978 | Moorehead |

(Continued)

FOREIGN PATENT DOCUMENTS

| EP | 0139091 | 7/1984 |
| EP | 0502714 | 11/1995 |

(Continued)

OTHER PUBLICATIONS

Arrow Trauma Products No. TRM-C 12/00 11M, Arrow International, dated 2000.

(Continued)

*Primary Examiner* — Aarti B Berdichevsky
(74) *Attorney, Agent, or Firm* — Knobbe Martens Olson & Bear LLP

(57) ABSTRACT

An access device for placing a medical article within a body space includes a needle, a dilator, and a medical article. The needle can include an elongated needle body with a distal end and a hub from which the needle body extends. The elongated needle body can include at least one side fenestration and an outer diameter. The dilator can be slideably disposed on the needle body and include a dilator hub and an elongated dilator shaft that extends from the dilator hub. The dilator shaft can include at least one side fenestration in communication with the needle side fenestration. The dilator shaft can also include an inner diameter that is less than the outer diameter of the needle. The medical article can include a tubular section and a hub. The tubular section can be disposed on the dilator and define a space between the medical article and the dilator in communication with the needle side fenestration through the dilator side fenestration. At a least portion of the medical article can be configured to allow visual determination of the presence of a body fluid within the space.

30 Claims, 45 Drawing Sheets

(51) Int. Cl.
*A61M 29/00* (2006.01)
*A61M 39/06* (2006.01)

(56) References Cited

U.S. PATENT DOCUMENTS

| | | |
|---|---|---|
| 4,205,675 A | 6/1980 | Vaillancourt |
| 4,230,123 A | 10/1980 | Hawkins, Jr. |
| 4,417,886 A | 11/1983 | Frankhouser et al. |
| 4,525,157 A | 6/1985 | Vaillancourt |
| 4,581,019 A | 4/1986 | Curelaru et al. |
| 4,610,665 A * | 9/1986 | Matsumoto et al. ..... 604/167.04 |
| 4,629,450 A | 12/1986 | Susuki et al. |
| 4,655,750 A | 4/1987 | Vaillancourt |
| 4,661,300 A | 4/1987 | Daugherty |
| 4,791,937 A | 12/1988 | Wang |
| 4,850,975 A | 7/1989 | Furukawa |
| 4,869,259 A | 9/1989 | Elkins |
| 4,894,052 A | 1/1990 | Crawford |
| 4,961,729 A | 10/1990 | Vaillancourt |
| 4,978,334 A | 12/1990 | Toye et al. |
| 5,059,186 A * | 10/1991 | Yamamoto et al. ........... 604/537 |
| 5,066,284 A | 11/1991 | Mersch et al. |
| 5,105,807 A * | 4/1992 | Kahn et al. ............... 128/207.18 |
| 5,108,374 A | 4/1992 | Lemieux |
| 5,112,308 A | 5/1992 | Olsen et al. |
| 5,167,637 A * | 12/1992 | Okada et al. ............. 604/167.04 |
| 5,171,218 A | 12/1992 | Fonger et al. |
| 5,242,410 A | 9/1993 | Melker |
| 5,246,426 A | 9/1993 | Lewis et al. |
| 5,250,038 A | 10/1993 | Melker et al. |
| 5,255,691 A | 10/1993 | Otten |
| 5,295,969 A | 3/1994 | Fischell |
| 5,295,970 A | 3/1994 | Clinton et al. |
| 5,306,253 A | 4/1994 | Brimhall |
| 5,312,355 A | 5/1994 | Lee |
| 5,366,441 A | 11/1994 | Crawford |
| 5,380,290 A | 1/1995 | Makower et al. |
| 5,542,932 A | 8/1996 | Daugherty |
| 5,589,120 A | 12/1996 | Khan et al. |
| 5,676,689 A | 10/1997 | Kensery et al. |
| 5,688,249 A | 11/1997 | Chang et al. |
| 5,704,914 A | 1/1998 | Stocking et al. |
| 5,712,229 A | 1/1998 | Hopkins et al. |
| 5,795,339 A | 8/1998 | Erskine |
| 5,810,780 A | 9/1998 | Brimhall et al. |
| 5,820,596 A | 10/1998 | Rosen et al. |
| 5,827,202 A | 10/1998 | Miraki et al. |
| 5,830,190 A | 11/1998 | Howell |
| 5,833,662 A | 11/1998 | Stevens |
| 5,858,002 A | 1/1999 | Jesch |
| 5,885,253 A | 3/1999 | Liu |
| 5,910,132 A | 6/1999 | Schultz |
| 5,935,110 A | 8/1999 | Brimhall |
| 6,046,143 A | 4/2000 | Khan et al. |
| 6,074,377 A | 6/2000 | Sanfilippo |
| 6,080,141 A | 6/2000 | Castro et al. |
| 6,120,494 A | 9/2000 | Jonkman |
| 6,156,010 A | 12/2000 | Kuracina et al. |
| 6,179,813 B1 | 1/2001 | Ballow et al. |
| 6,277,100 B1 | 8/2001 | Raulerson |
| 6,436,070 B1 | 8/2002 | Botich et al. |
| 6,461,362 B1 | 10/2002 | Halseth et al. |
| 6,524,277 B1 | 2/2003 | Chang |
| 6,607,511 B2 | 8/2003 | Halseth et al. |
| 6,641,564 B1 | 11/2003 | Kraus |
| 6,692,462 B2 | 2/2004 | Mackenzie et al. |
| 6,726,659 B1 | 4/2004 | Stocking et al. |
| 6,808,520 B1 | 10/2004 | Fourkas et al. |
| 6,994,693 B2 | 2/2006 | Tal |
| 7,001,396 B2 | 2/2006 | Glazier et al. |
| 7,025,746 B2 | 4/2006 | Tal |
| 7,182,755 B2 | 2/2007 | Tal |
| 7,192,433 B2 | 3/2007 | Osypka et al. |
| 7,270,649 B2 | 9/2007 | Fitzgerald |
| 7,556,617 B2 | 7/2009 | Voorhees, Jr. et al. |
| 7,722,567 B2 | 5/2010 | Tal |
| 7,922,696 B2 | 4/2011 | Tal et al. |
| 8,105,286 B2 | 1/2012 | Anderson et al. |
| 8,192,402 B2 | 6/2012 | Anderson et al. |
| 8,202,251 B2 | 6/2012 | Bierman et al. |
| 2002/0072712 A1 | 6/2002 | Nool et al. |
| 2004/0092879 A1 | 5/2004 | Kraus et al. |
| 2004/0171988 A1 | 9/2004 | Moretti |
| 2008/0262431 A1* | 10/2008 | Anderson et al. .......... 604/164.1 |
| 2009/0221961 A1 | 9/2009 | Tal et al. |
| 2011/0021994 A1* | 1/2011 | Anderson et al. ........ 604/164.01 |
| 2011/0202006 A1* | 8/2011 | Bierman et al. ......... 604/164.03 |
| 2011/0218496 A1* | 9/2011 | Bierman .................. 604/164.13 |
| 2011/0276002 A1* | 11/2011 | Bierman .................... 604/164.1 |
| 2012/0065590 A1 | 3/2012 | Bierman et al. |
| 2012/0316500 A1 | 12/2012 | Bierman et al. |

FOREIGN PATENT DOCUMENTS

| | | |
|---|---|---|
| KR | 10-2005-0027359 | 3/2005 |
| WO | WO 2009-114833 | 9/2009 |
| WO | WO 2012/135761 | 10/2012 |
| WO | WO 2012/162677 | 11/2012 |
| WO | WO 2013/026045 | 2/2013 |

OTHER PUBLICATIONS

International Search Report and Written Opinion, PCT/US2011/024097, mailed on Oct. 25, 2011.

* cited by examiner

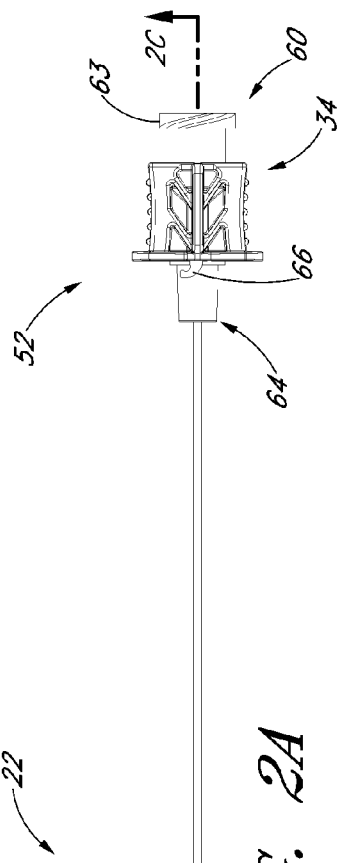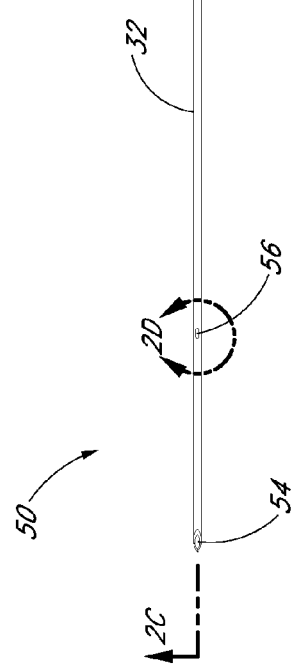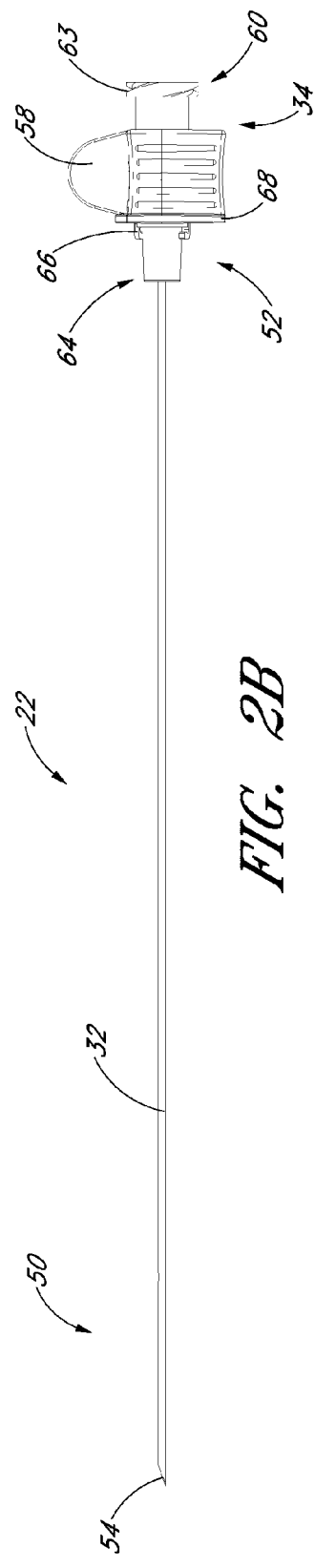

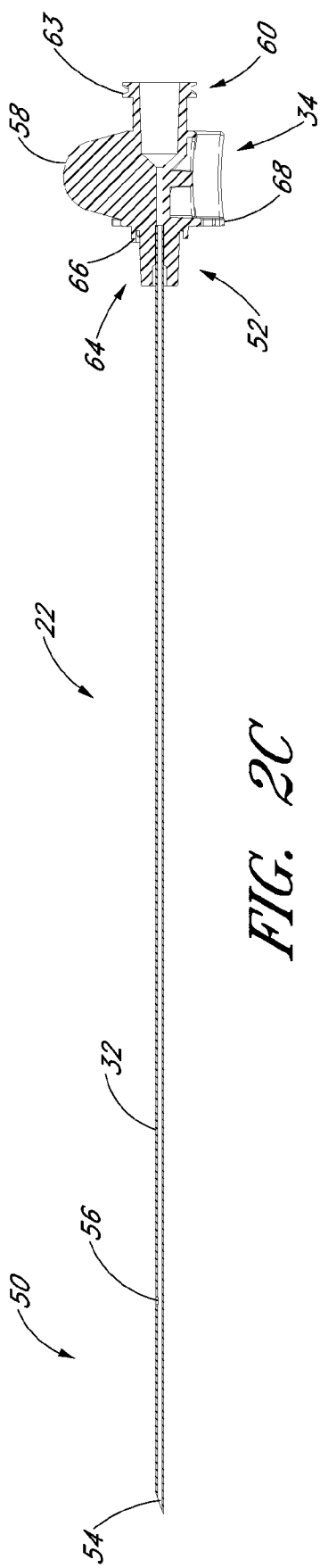
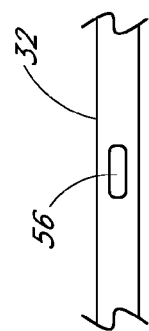
FIG. 2C
FIG. 2D

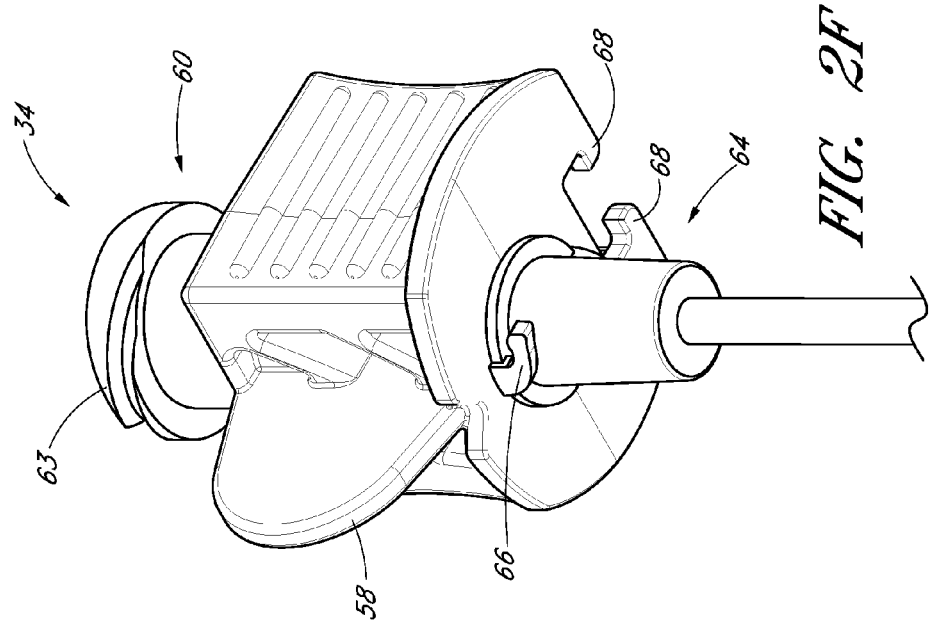
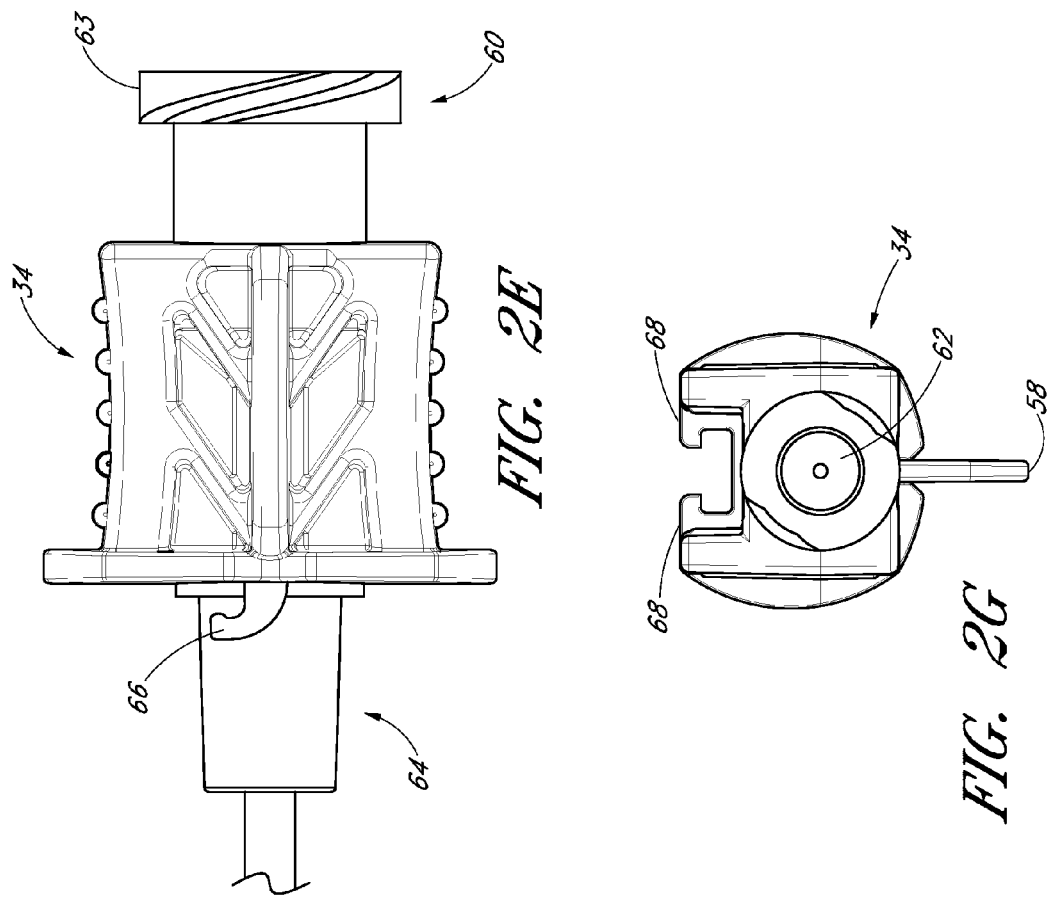

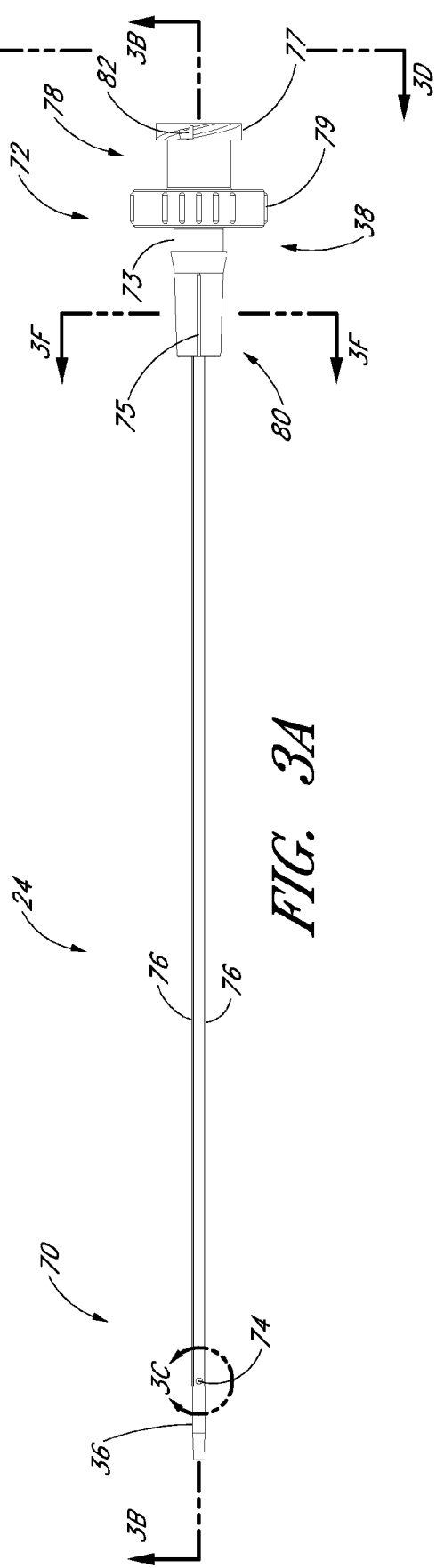
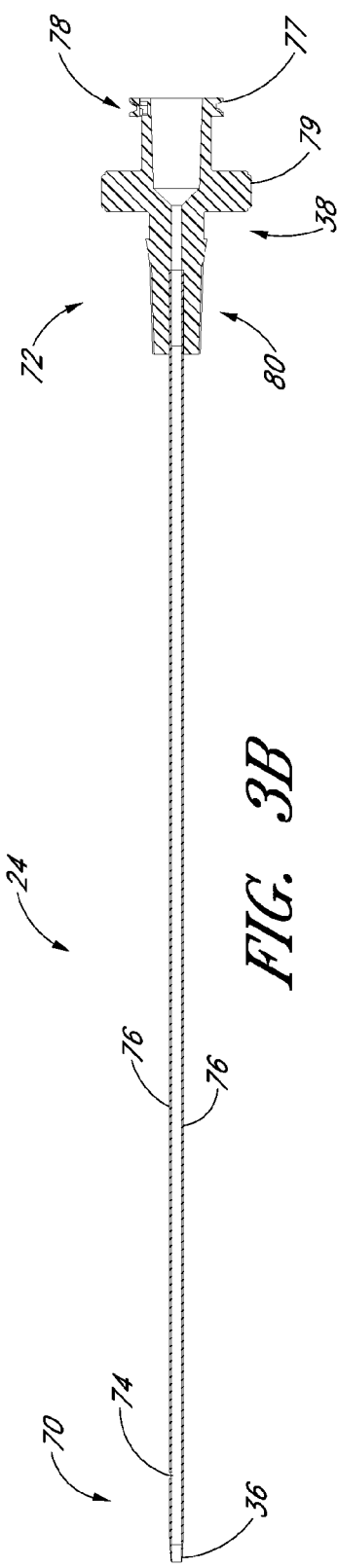
FIG. 3A
FIG. 3B

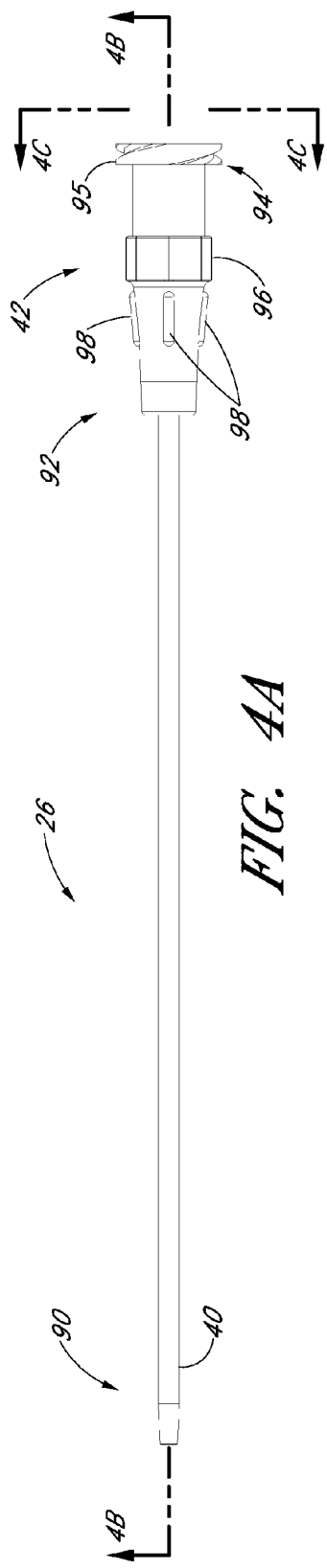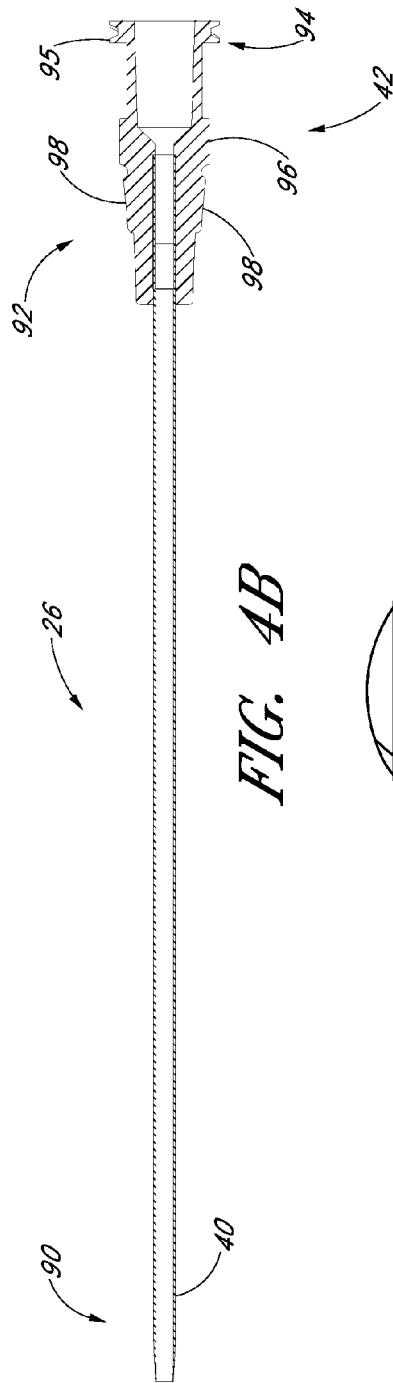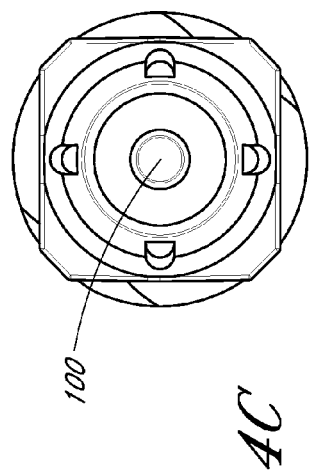
FIG. 4A
FIG. 4B
FIG. 4C

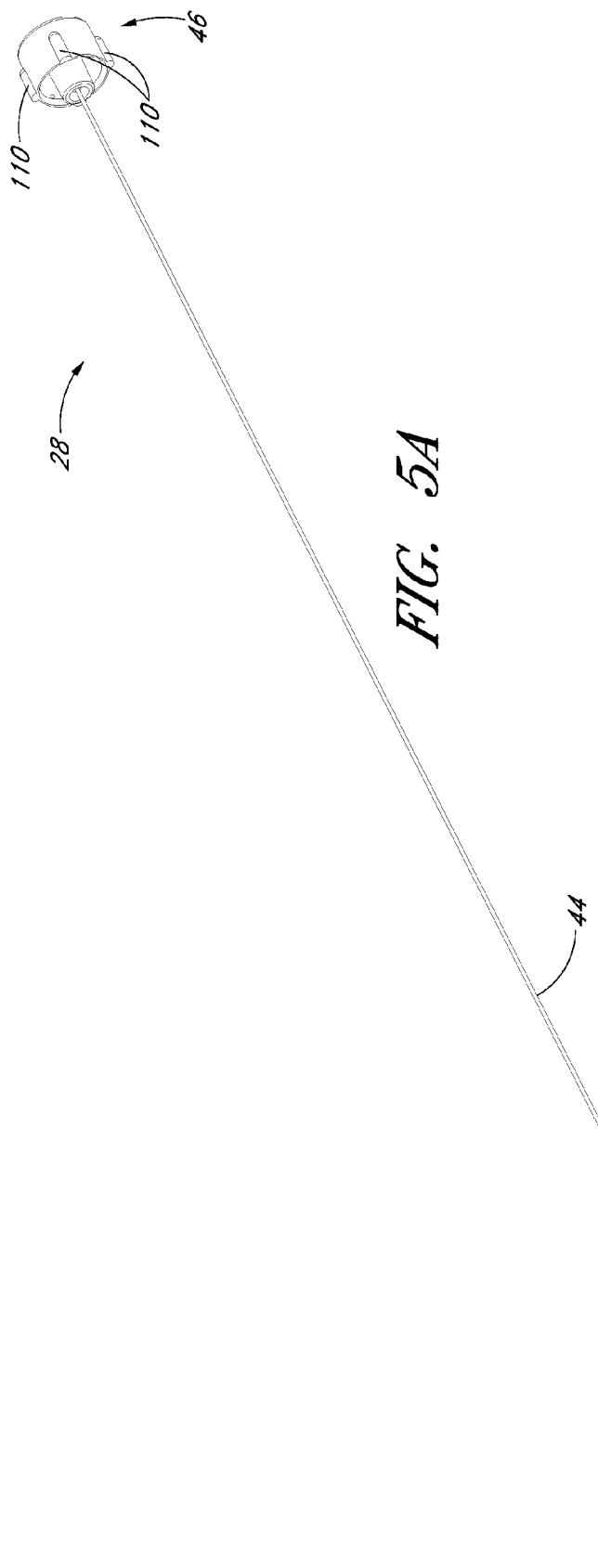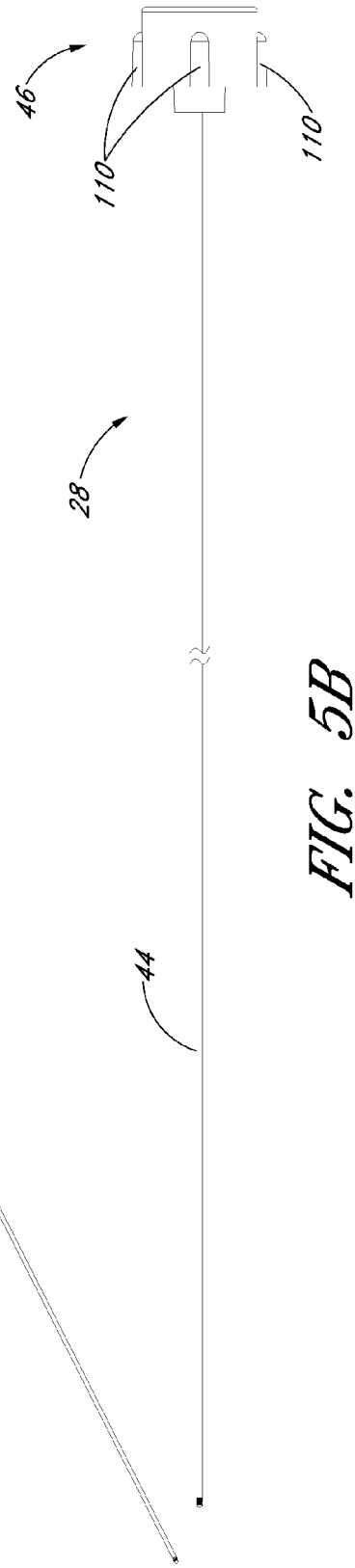

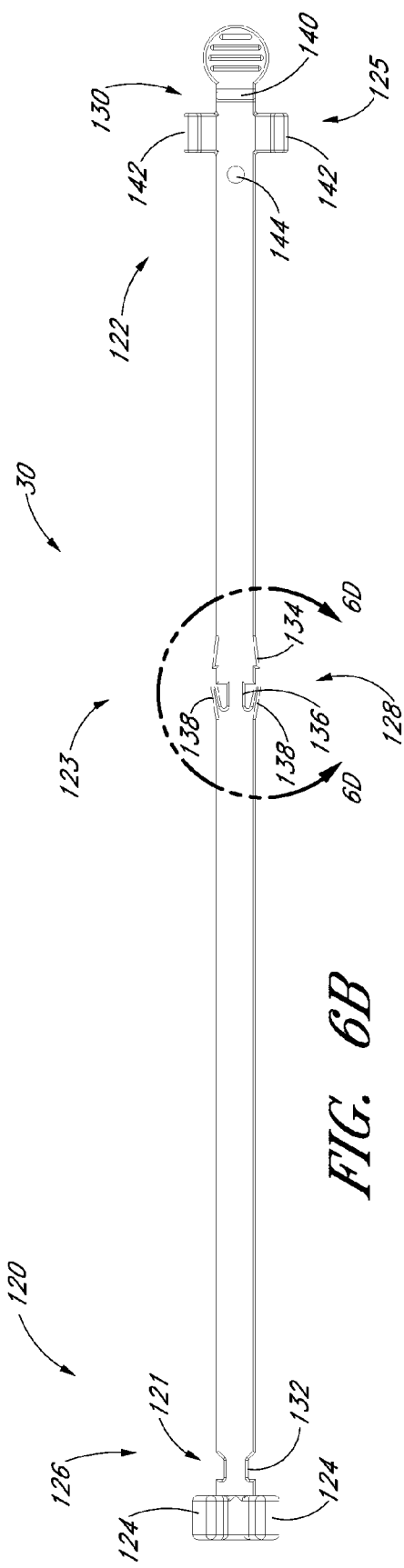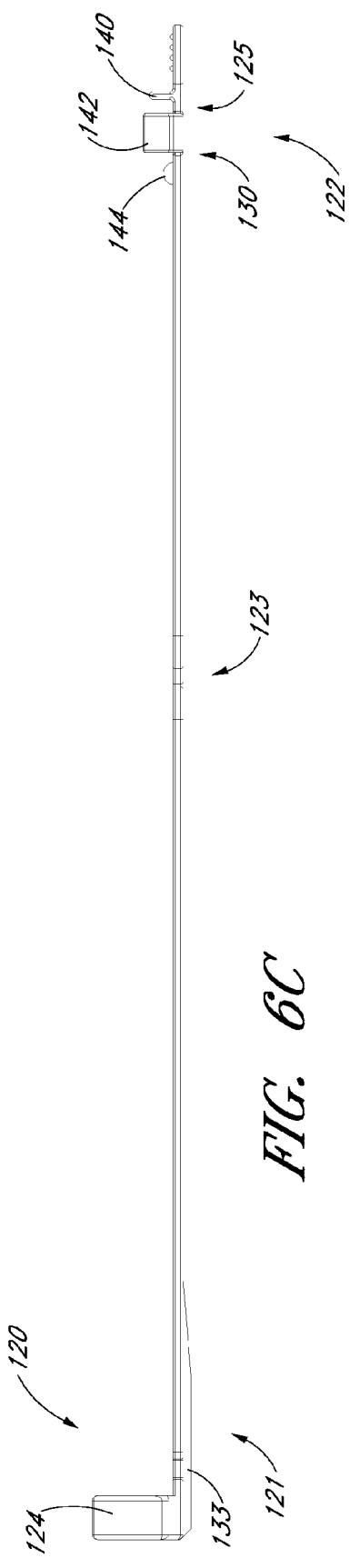
FIG. 6B
FIG. 6C

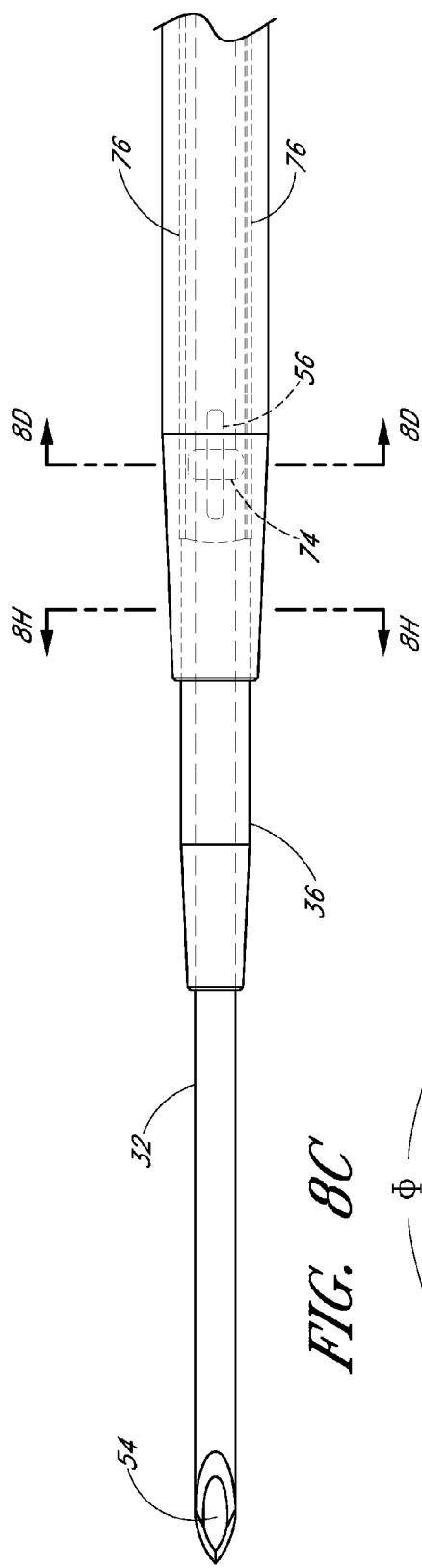
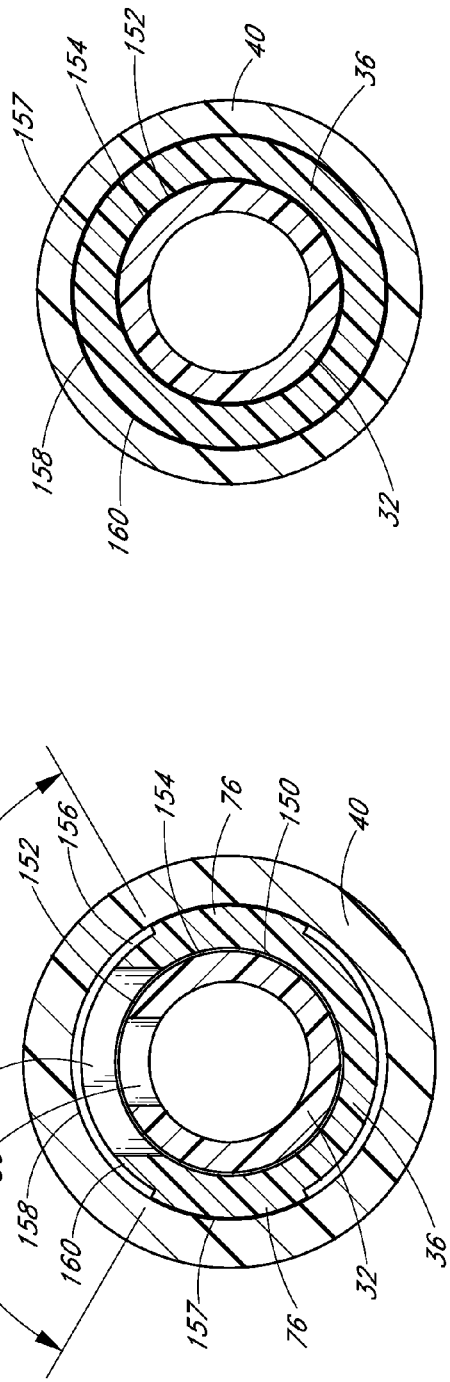
FIG. 8C
FIG. 8D
FIG. 8H

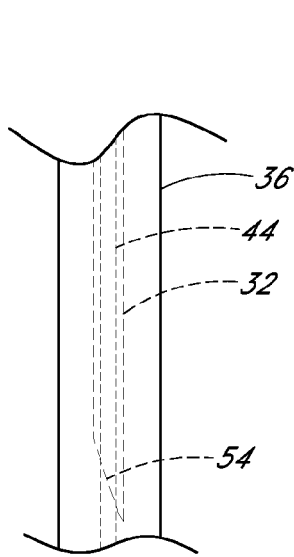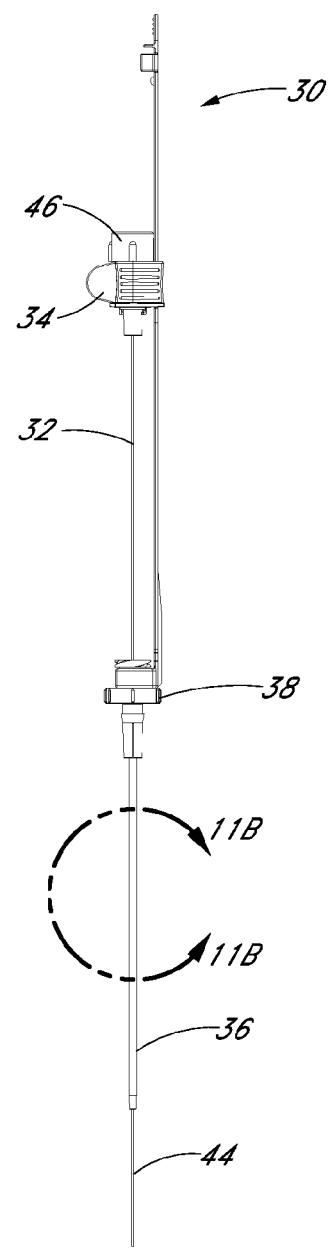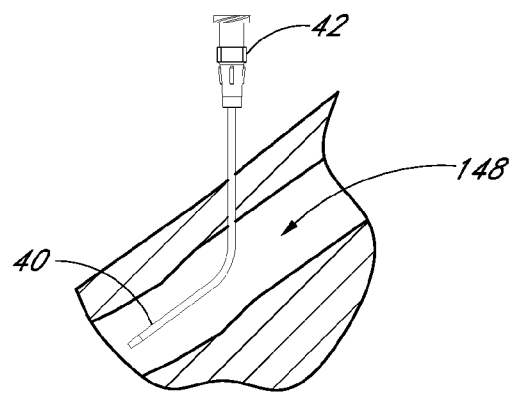
FIG. 11B
FIG. 11A

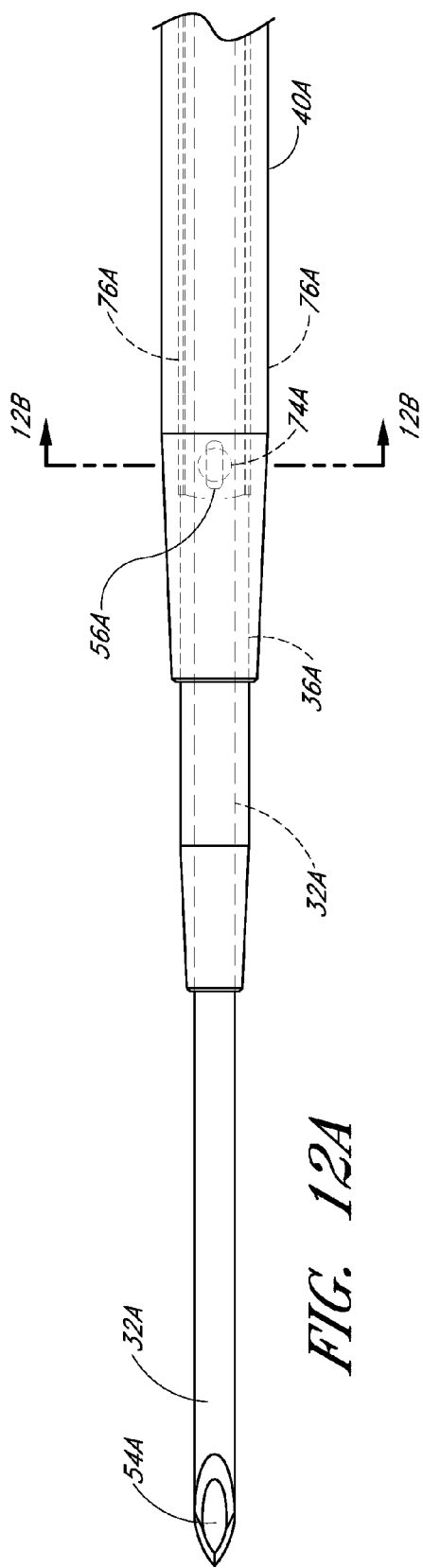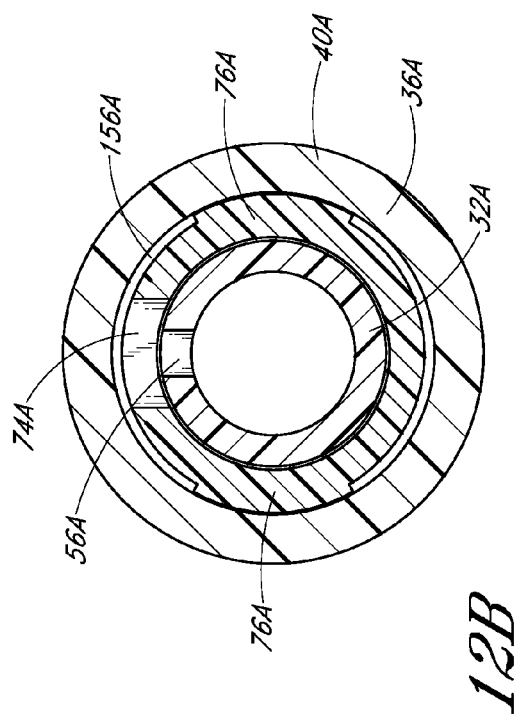
FIG. 12A
FIG. 12B

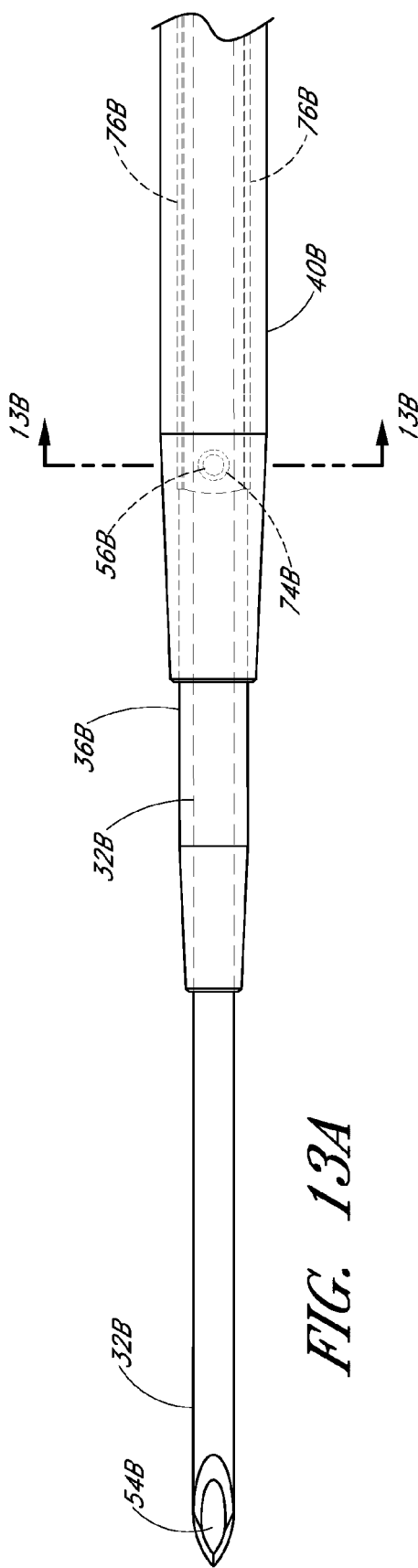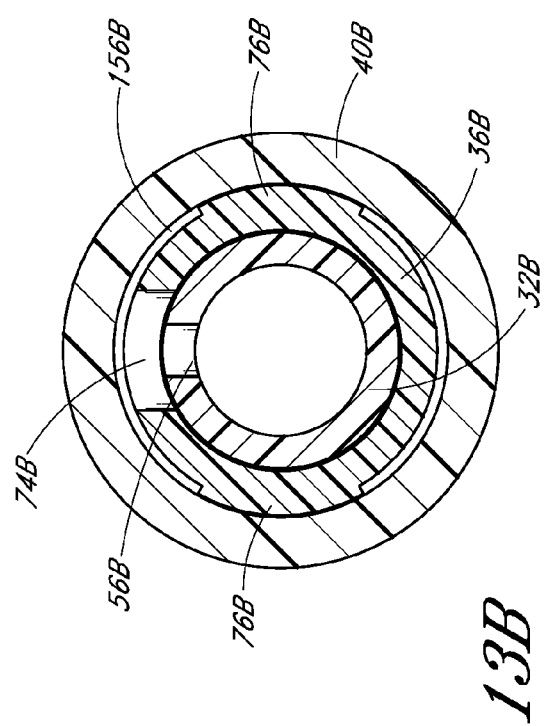
FIG. 13A
FIG. 13B

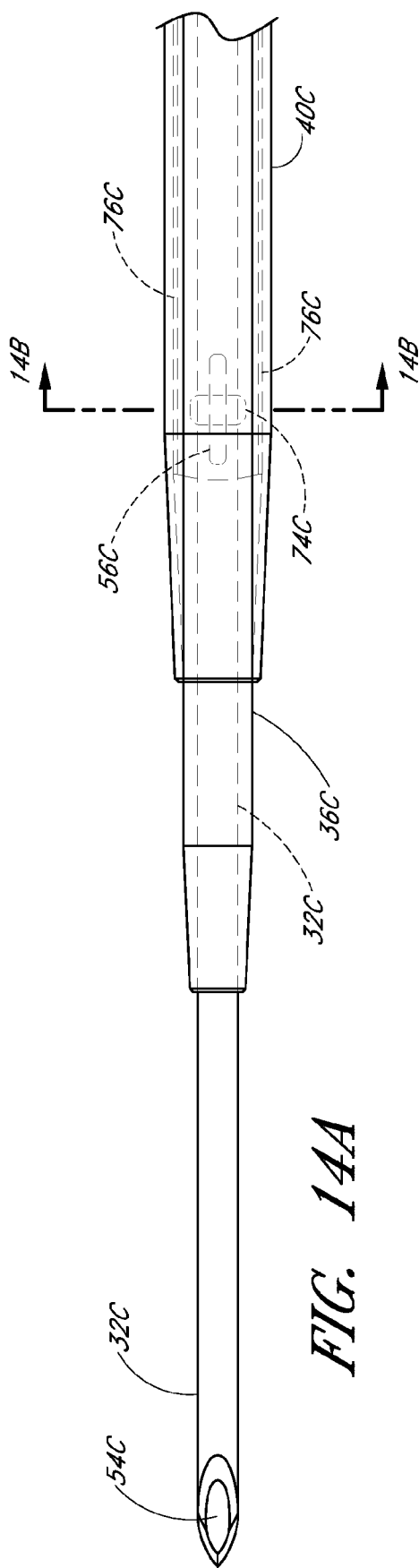
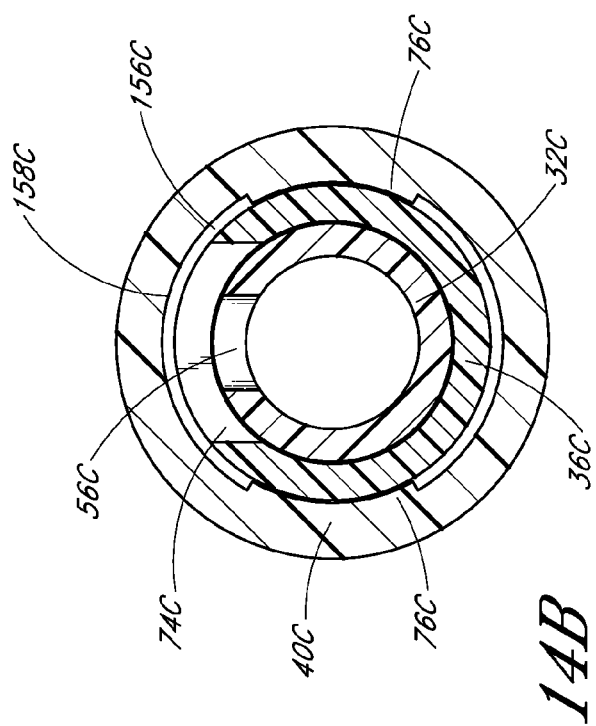
FIG. 14A
FIG. 14B

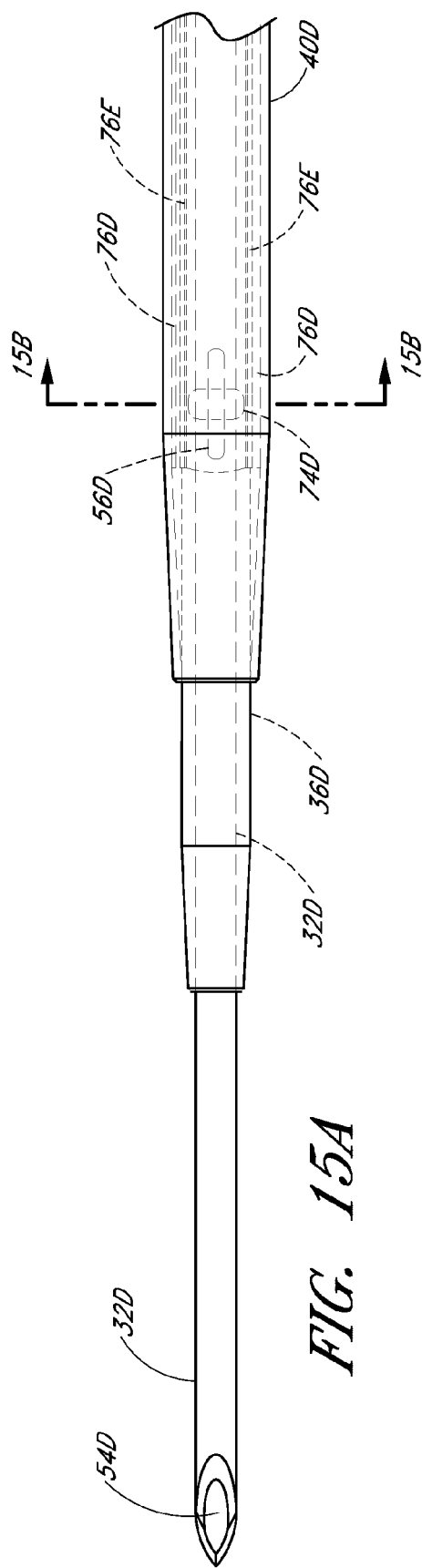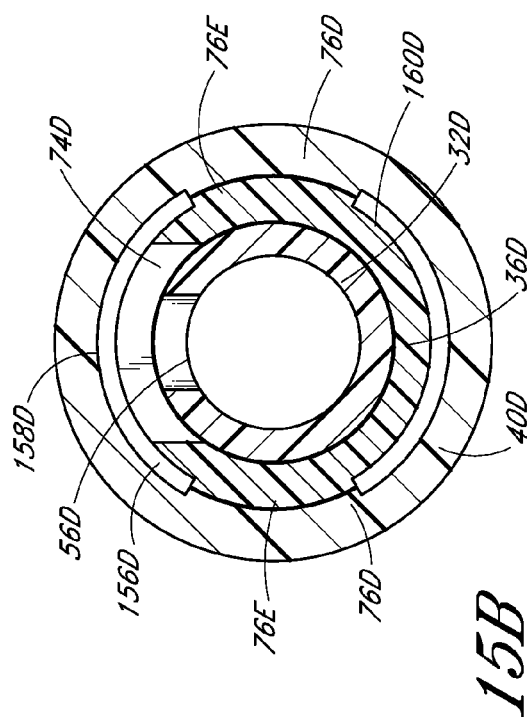

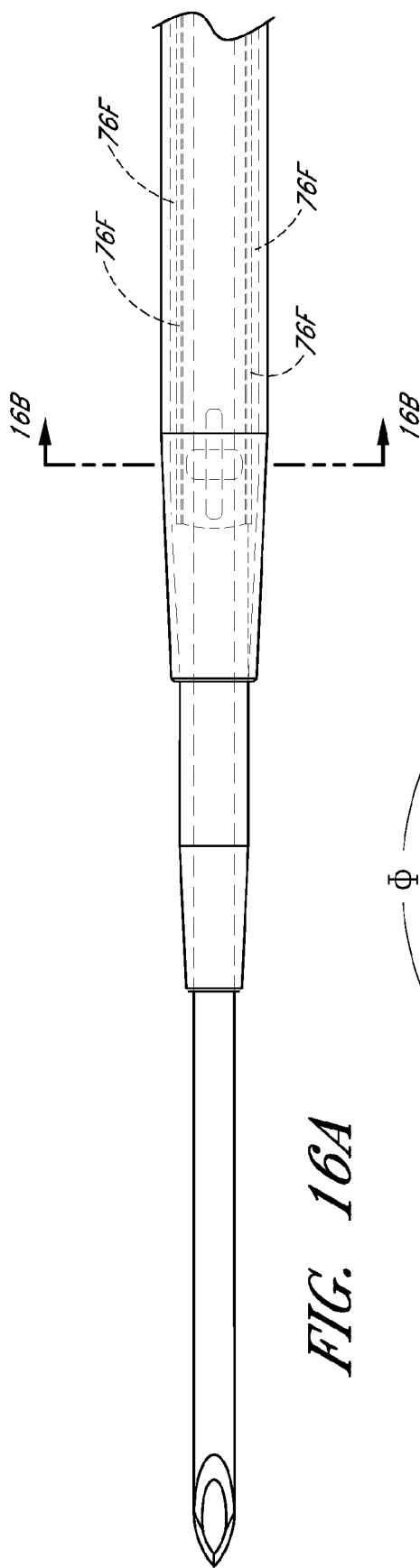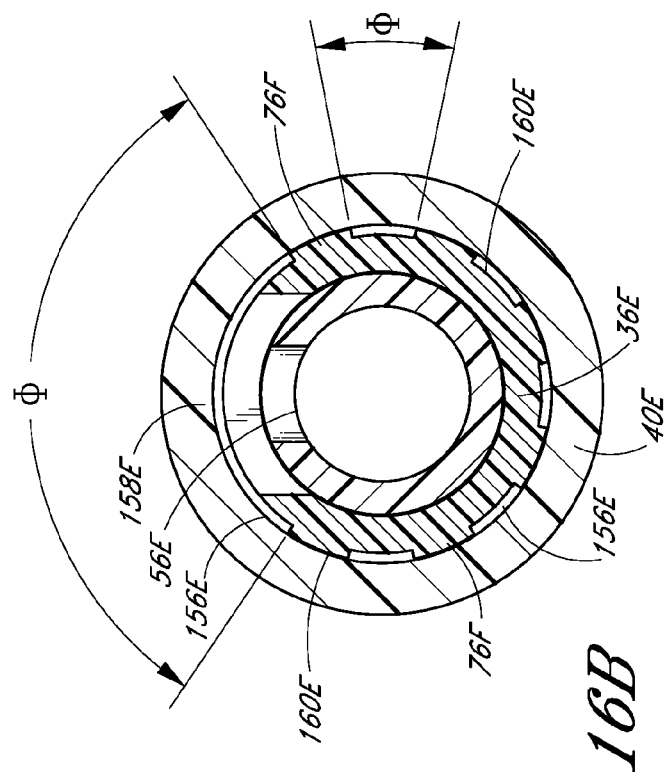
FIG. 16A
FIG. 16B

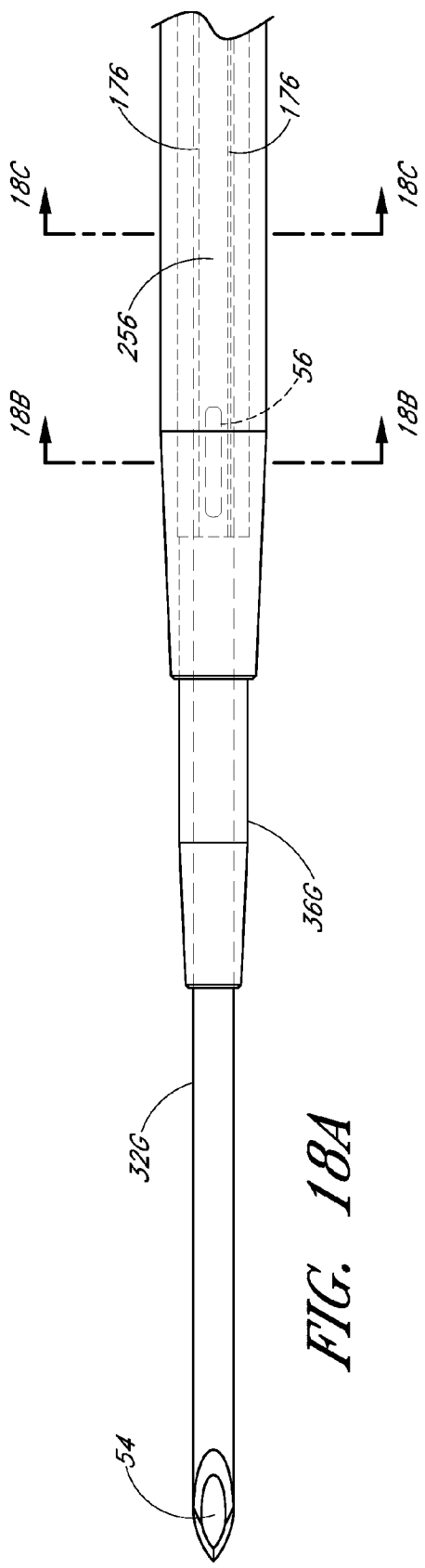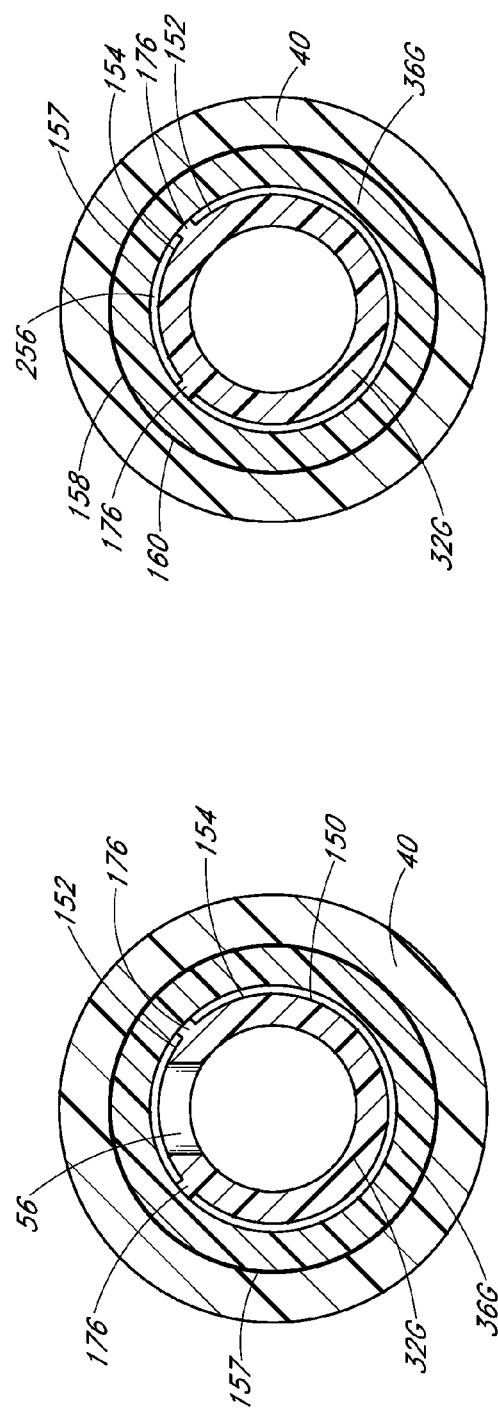
FIG. 18A
FIG. 18B
FIG. 18C

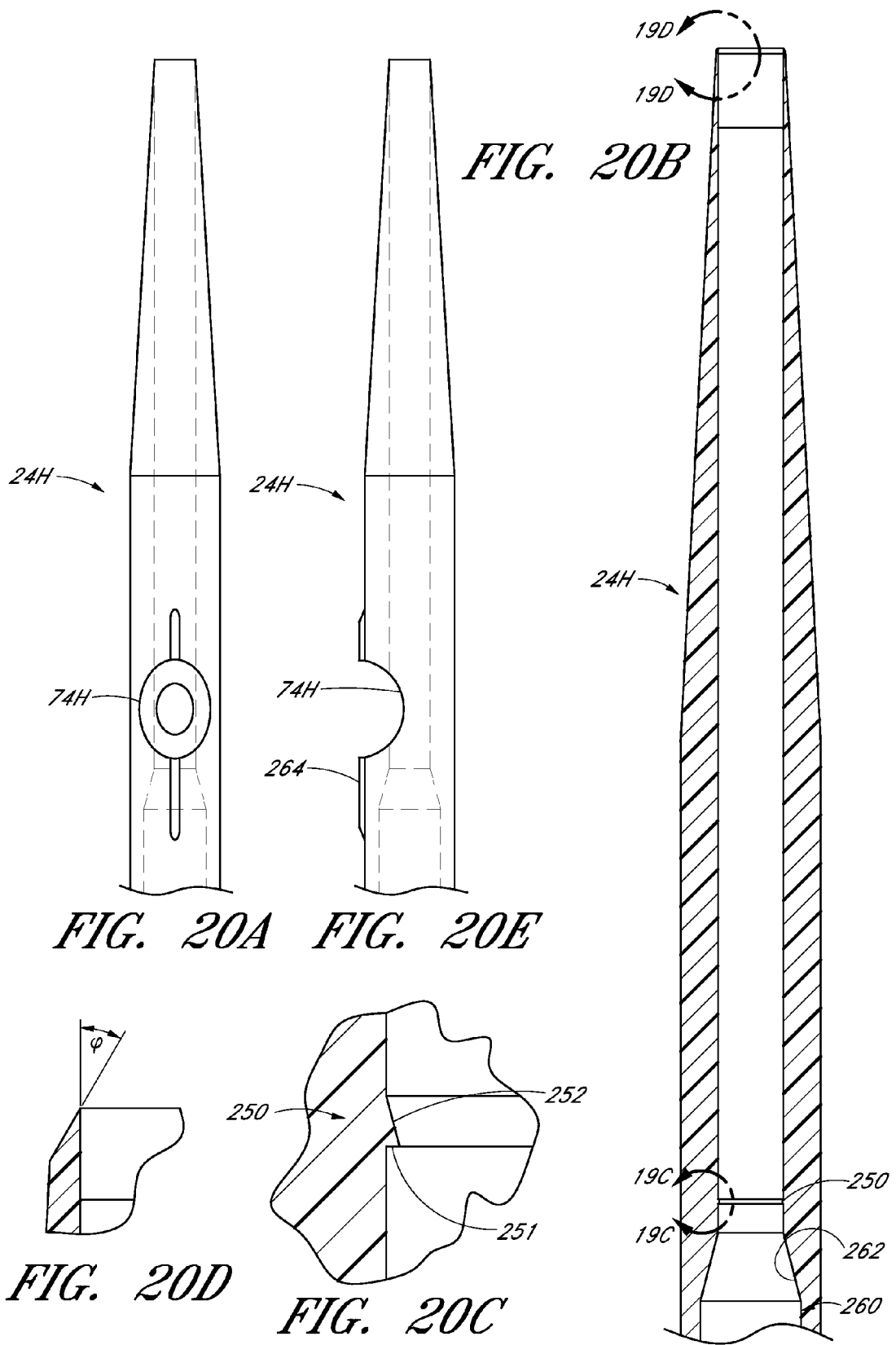

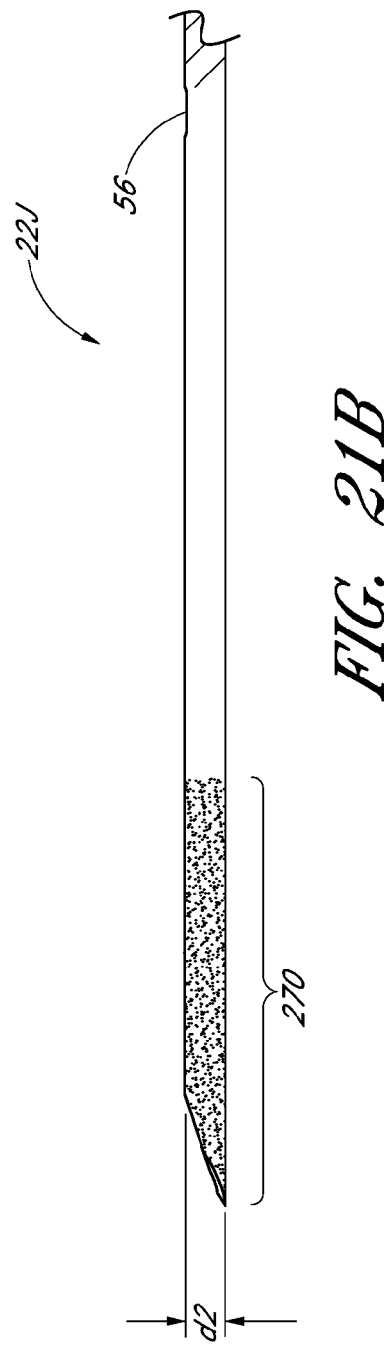

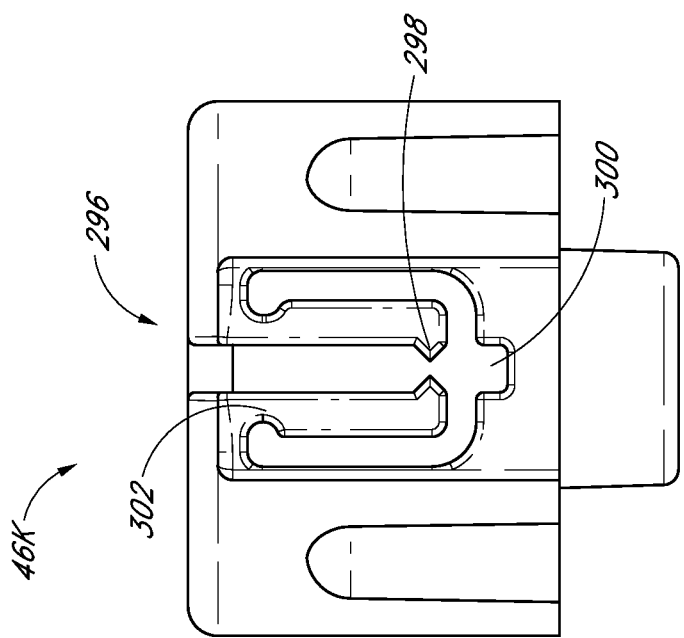
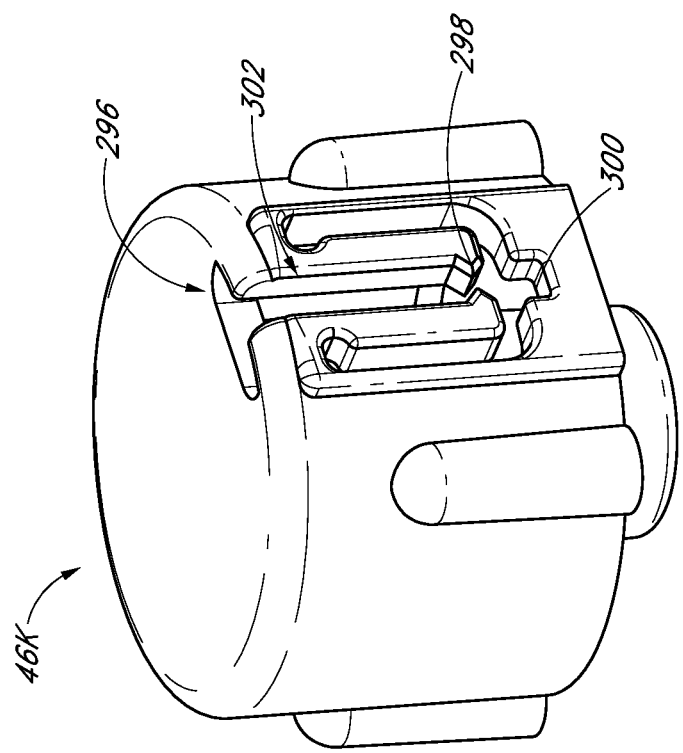
FIG. 23B
FIG. 23A

ACCESS DEVICE

CROSS-REFERENCE TO RELATED APPLICATIONS

This application is a U.S. National Phase of International Application No. PCT/US2011/024097, filed 8 Feb. 2011, designating the United States and published on 11 Aug. 2011 as WO 2011/097639, which claims the priority benefit under 35 U.S.C. §119(e) to U.S. Provisional Patent Application Ser. No. 61/302,486 (filed 8 Feb. 2010), the entirety of which being hereby expressly incorporated by reference herein.

BACKGROUND

1. Field of the Invention

This invention is generally directed to access devices for introducing and/or delivering a medical article (such as, for example, a catheter, cannula, sheath, etc.) into a body space, such as, for example, an artery, vein, vessel, body cavity, or drainage site.

2. Description of the Related Art

A preferred non-surgical method for inserting a catheter or vascular sheath into a blood vessel involves the use of the Seldinger or a modified Seldinger technique, which includes an access needle that is inserted into a patient's blood vessel. A guidewire is inserted through the needle and into the vessel. The needle is removed, and a dilator and sheath in combination or separately are then inserted over the guidewire. The dilator and sheath, together or separately, are then inserted a short distance through the tissue into the vessel, after which the dilator and guidewire are removed and discarded. A catheter or other medical article may then be inserted through the sheath into the vessel to a desired location, or the sheath may simply be left in the vessel.

A number of vascular access devices are known. U.S. Pat. Nos. 4,241,019, 4,289,450, 4,756,230, 4,978,334, 5,124,544, 5,424,410, 5,312,355, 5,212,052, 5,558,132, 5,885,217, 6,120,460, 6,179,823, 6,210,332, 6,726,659 and 7,025,746 disclose examples of such devices. None of these devices, however, has the ease and safety of use that physicians and other healthcare providers would prefer. Thus, there exists a need for an easier-to-use and safer vascular access device, especially one that would clearly and promptly indicate when a blood vessel has been punctured and one that would reduce accidental needle sticks and other attendant risks of over-wire vascular access.

SUMMARY

The described embodiments involve several features for an access device useful for the delivery of a catheter or sheath into a space within a patient's body, such as, for example, a blood vessel or drainage site. Without limiting the scope of this invention, its more prominent features will be discussed briefly. After considering this discussion, and particularly after reading the Detailed Description of the Preferred Embodiments section below in combination with this section, one will understand how the features and aspects of these embodiments provide several advantages over prior access devices.

In one embodiment, an access device for placing a medical article within a body space includes a needle, a dilator, and a medical article. The needle can include an elongated needle body with a distal end and a hub from which the needle body extends. The elongated needle body can include at least one side fenestration and an outer diameter. The dilator can be slideably disposed on the needle body and include a dilator hub and an elongated dilator shaft that extends from the dilator hub. The dilator shaft can include at least one side fenestration in communication with the needle side fenestration. The dilator shaft can also include an inner diameter that is less than the outer diameter of the needle. The medical article can include a tubular section and a hub. The tubular section can be disposed on the dilator and define a space between the medical article and the dilator in communication with the needle side fenestration through the dilator side fenestration. At a least portion of the medical article can be configured to allow visual determination of the presence of a body fluid within the space.

In another embodiment an access device for placing a medical article within a body space can include a needle, a dilator, and a medical article. The needle can include an elongated needle body with a distal end and a hub from which the needle body extends. The dilator can be slideably disposed on the needle body and include a dilator hub and an elongated dilator shaft that extends from the dilator hub. The dilator shaft can include at least one side fenestration in communication with the needle side fenestration and a raised ridge through which the fenestration passes. The medical article includes a tubular section and a hub. The tubular section can be disposed on the dilator and define a space between the medical article and the dilator in communication with the needle side fenestration through the dilator side fenestration. At a least portion of the medical article can be configured to allow visual determination of the presence of a body fluid within the space.

In yet another embodiment, an access device for placing a medical article within a body space can include a needle, a dilator, and a medical article. The needle can include an elongated needle body with a distal end and a hub from which the needle body extends. The dilator can be slideably disposed on the needle body and include a dilator hub and an elongated dilator shaft that extends from the dilator hub to a distal end. The dilator shaft can include at least one side fenestration in communication with the needle side fenestration, and the dilator distal end can taper at approximately 30 degrees. The medical article includes a tubular section and a hub. The tubular section can be disposed on the dilator and define a space between the medical article and the dilator in communication with the needle side fenestration through the dilator side fenestration. At a least portion of the medical article can be configured to allow visual determination of the presence of a body fluid within the space.

In a further embodiment, an access device for placing a medical article within a body space can include a needle, a dilator, a sealing piece, and a medical article. The needle can include an elongated needle body with a distal end and a hub from which the needle body extends. The dilator can be slideably disposed on the needle body and include a dilator hub and an elongated dilator shaft that extends from the dilator hub to a distal end. The dilator shaft can include at least one side fenestration in communication with the needle side fenestration. The sealing piece can be slideably disposed on the needle body and be disposed between the dilator and the needle to inhibit fluid flow between the dilator and needle hubs. The medical article includes a tubular section and a hub. The tubular section can be disposed on the dilator and define a space between the medical article and the dilator in communication with the needle side fenestration through the dilator side fenestration. At a least portion of the medical article can be configured to allow visual determination of the presence of a body fluid within the space.

In another embodiment, a method of accessing a body cavity is provided. A needle with a hollow bore, a side fenestration, and a needle hub can be inserted into a body cavity. A dilator with a side fenestration and a dilator hub can be axially disposed on the needle and a medical article can be axially disposed on the dilator. A body fluid can be drawn from the body cavity through the needle bore to the needle side fenestration. Further, the body fluid can be drawn through the needle side fenestration and through the dilator side fenestration into a space between the dilator and the medical article. Movement of the body fluid proximally between the needle and the dilator hub can be inhibited.

In yet another embodiment an access device for placing a medical article within a body space can include a guidewire section, a needle, a dilator, and two locking mechanisms. The guidewire section can include a guidewire and a guidewire hub. The needle can be disposed on the guidewire and have an elongated needle body with a distal end and a hub from which the needle body extends. The dilator can be disposed on the needle body, the needle and the dilator being moveable relative to each other from a first position, wherein the distal end of the needle lies distal of the dilator, and a second position wherein the distal end of the needle lies within the dilator. The dilator can also include a dilator hub and an elongated dilator shaft that extends from the dilator hub. The first locking mechanism can operate between the needle and the dilator, and can include a portion spaced from the dilator that inhibits movement of the needle relative to the dilator when in the second position. The first locking mechanism can be configured to allow movement of the needle from the first position toward the second position without engagement by the locking mechanism so as to lessen resistance to the movement. The second locking mechanism can operate between the dilator and the guidewire, and can include a T-shaped locking section disposed on the guidewire that interengages with the guidewire hub to form a reversible snap-fit grip.

These and other aspects of the present invention will become readily apparent to those skilled in the art from the following detailed description of the preferred embodiments, which refers to the attached figures. The invention is not limited, however, to the particular embodiments that are disclosed.

BRIEF DESCRIPTION OF THE DRAWINGS

These and other features, aspects, and advantages of the access device disclosed herein are described below with reference to the drawings of preferred embodiments, which are intended to illustrate and not to limit the invention. Additionally, from figure to figure, the same reference numerals have been used to designate the same components of an illustrated embodiment. Like components between the illustrated embodiments are similarly noted as the same reference numbers with a letter suffix to indicate another embodiment. The following is a brief description of each of the drawings.

FIG. 2A is a plan view of the needle from FIG. 1A and shows a fenestration near a distal end.

FIG. 2B is a side view of the needle from FIG. 1A and shows a fin near a proximal end.

FIG. 2C is a cross-sectional view taken along the lines 2C-2C in FIG. 2A.

FIG. 2D is an enlarged plan view of a portion of the needle of FIG. 2A and shows the fenestration.

FIG. 2E is an enlarged plan view of the needle hub of the needle of FIG. 2A.

FIG. 2F is an enlarged side view of the needle hub of the needle of FIG. 2A.

FIG. 2G is an enlarged proximal end view of the needle hub of the needle of FIG. 2A.

FIG. 3A is a plan view of the dilator from FIG. 1A and shows a fenestration near a distal end. FIG. 3A also shows longitudinally arranged grooves in the luer surface for venting air from between the dilator and sheath.

FIG. 3B is a cross-sectional view taken along the lines 3B-3B in FIG. 3A.

FIG. 4A is a plan view of the sheath from FIG. 1A and shows a sheath hub connected to a proximal end of a sheath.

FIG. 4B is a cross-sectional view taken along the lines 4B-4B in FIG. 4A.

FIG. 4C is an enlarged end view of the sheath from FIG. 4A.

FIG. 5A is a perspective view of the guidewire section from FIG. 1A and shows a guidewire hub connected to a proximal end of a guidewire.

FIG. 5B is a plan view of the guidewire section of the embodiment depicted in FIG. 5A.

FIG. 6B is a plan view of the track in FIG. 6A and shows a locking mechanism for locking the needle relative to the dilator.

FIG. 6C is a side view of the track in FIG. 6B.

FIG. 8C is an enlarged view of a portion of the embodiment depicted in FIG. 8B and illustrates the needle opening or fenestration aligned with the dilator opening or fenestration in hidden lines.

FIG. 8D is an enlarged cross-sectional view of a portion of the embodiment depicted in FIG. 8C and shows the needle opening or fenestration aligned with the dilator opening or fenestration so as to allow fluid to flow from inside the needle to a channel formed between the sheath and dilator.

FIG. 8H is an enlarged cross-sectional view of a portion of the embodiment depicted in FIG. 8C taken through a region distal of the channel in the dilator.

FIG. 11A is a side view of the embodiment depicted in FIG. 1A illustrating the removal of the guidewire, needle body, and dilator from the sheath.

FIG. 11B is an enlarged view of the portion of the embodiment illustrated in FIG. 11A showing the needle tip covered by the dilator during removal of the guidewire, needle body, and dilator from the sheath.

FIG. 12A is an enlarged plan view that illustrates another embodiment of the aligned openings or fenestrations in the needle and dilator.

FIG. 12B is an enlarged cross-sectional view along lines 13B-13B in FIG. 12A and shows the needle opening or fenestration aligned with the dilator opening or fenestration so as to allow fluid to flow from inside the needle to a channel formed between the sheath and dilator.

FIG. 13A is an enlarged plan view that illustrates another embodiment of the aligned openings or fenestrations in the needle and dilator.

FIG. 13B is an enlarged cross-sectional view along lines 13B-13B in FIG. 13A and shows the needle opening or fenestration aligned with the dilator opening or fenestration so as to allow fluid to flow from inside the needle to a channel formed between the sheath and dilator FIG. 14A is an enlarged plan view that illustrates another embodiment of the channel formed between the dilator and the sheath.

FIG. 14B is a cross-sectional view along lines 14B-14B in FIG. 14A and shows the thickness of the channel extending into the sheath.

FIG. 15A is an enlarged plan view that illustrates another embodiment of the channel formed between the dilator and the sheath.

FIG. 15B is a cross-sectional view along lines 15B-15B in FIG. 15A and shows the thickness of the channel extending into both the dilator and the sheath.

FIG. 16A is an enlarged plan view that illustrates another embodiment of the channel formed between the dilator and the sheath.

FIG. 16B is a cross-sectional view along lines 16B-16B in FIG. 15A and shows a plurality of equally spaced channels in the form of splines extending into the dilator.

FIG. 18A is an enlarged plan view of a portion of another embodiment of the access device and illustrates another embodiment of a channel this time formed between the needle and the dilator.

FIG. 18B is an enlarged cross-sectional view through the embodiment of FIG. 18A taken at 18B-18B.

FIG. 18C is an enlarged cross-sectional view through the embodiment of FIG. 18A taken at 18C-18C.

FIG. 20A is a plan view of a distal portion of another embodiment of a dilator.

FIG. 20B is a cross-sectional view of the distal portion of the dilator of FIG. 20A, with a fenestration in phantom.

FIG. 20C is an enlarged view of a section of the dilator of FIG. 20B taken at 20C-20C.

FIG. 20D is an enlarged view of a section of the dilator of FIG. 20B taken at 20D-20D.

FIG. 20E is a side view of the dilator of FIG. 20A, with interior features in phantom.

FIG. 21A is a side view of another embodiment of a needle.

FIG. 21B is an enlarged view of a distal end of the needle of FIG. 21A.

FIG. 23A is a perspective view of another embodiment of a guidewire hub.

FIG. 23B is a bottom view of the guidewire hub of FIG. 23A.

DETAILED DESCRIPTION OF THE PREFERRED EMBODIMENTS

Figure 1A:
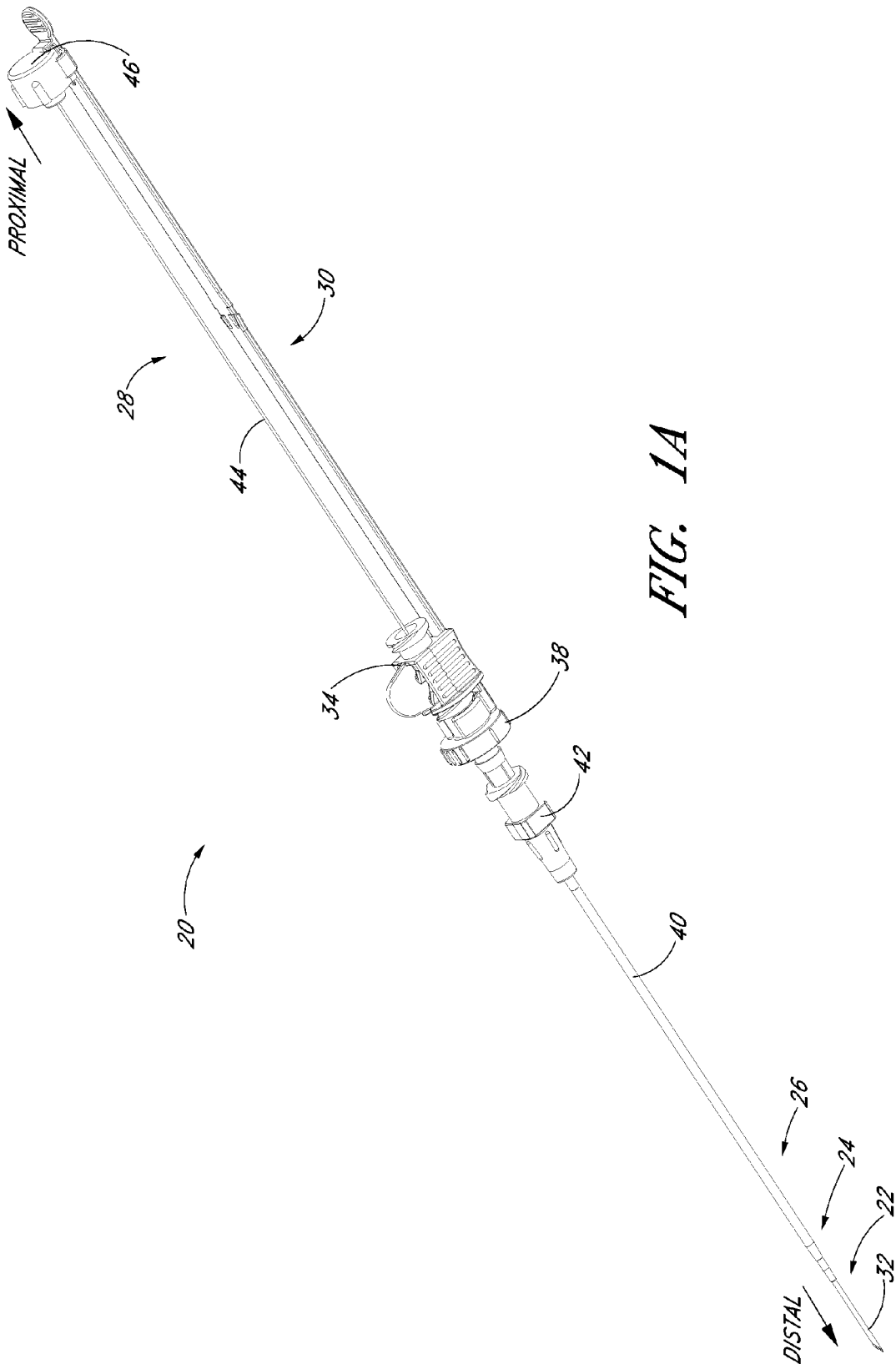
FIG. 1A is a perspective view of a preferred embodiment of an access device configured in accordance with the present invention and shows a pre-loaded guidewire section coaxially aligned with a needle, a dilator, and a medical article.

The present disclosure provides an access device for the delivery of a medical article (e.g., catheter or sheath) to a blood vessel or drainage site. FIG. 1A illustrates an access device 20 that is configured to be inserted into a blood vessel (e.g., a vein or an artery) in accordance with a preferred embodiment of the present invention. While the access device is described below in this context (i.e., for vascular access), the access device also can be used to access and place a medical article (e.g., catheter or sheath) into other locations within a patient's body (e.g., a drainage site) and for other purposes (e.g., for draining an abscess).

The present embodiment of the access device is disclosed in the context of placing an exemplary single-piece, tubular medical article into a body space within a patient. Once placed, the tubular article can then be used to receive other medical articles (e.g., catheters, guidewires, etc.) to provide access into the body space and/or be used to provide a passage way for introducing fluids into the body space or removing (e.g., draining) fluids from the body space. In the illustrated embodiment, the tubular medical article is a sheath or catheter that is configured primarily to provide a fluid passage into a vein. The principles of the present invention, however, are not limited to the placement of single piece sheaths or catheters, or to the subsequent insertion of a medical article via the sheath or catheter. Instead, it will be understood by one of skill in this art, in light of the present disclosure, that the access device disclosed herein also can be successfully utilized in connection with placing one or more other types of medical articles, including other types of sheaths, fluid drainage and delivery tubes, and single or multi-lumen catheters directly in the patient or indirectly via another medical article.

For example, but without limitation, the access device disclosed herein can also be configured to directly or indirectly place central venous catheters, peripherally inserted central catheters, hemodialysis catheters, surgical drainage tubes, tear-away sheaths, multi-piece sheaths, scopes, as well as electrical conduit for wires or cables connected to external or implanted electronic devices or sensors. As explained above, the medical articles listed above may be directly placed in the patient via the dilator, needle, and guidewire of the access device or subsequently placed within the patient via a medical article that was placed within the patient via the dilator, needle, and guidewire of the access device.

Further, the embodiments disclosed herein are not limited to co-axial insertion of a single medical article. For example, two catheters may be inserted in the patient via an inserted sheath or a second catheter may be inserted in the patient via an inserted first catheter. Further, in addition to providing a conduit into the vessel or other body space, the medical article inserted via the dilator, needle, and guidewire can form a lumen that is in addition to the lumen(s) of the subsequently inserted medical article. One skilled in the art can also find additional applications for the devices and systems disclosed herein. Thus, the illustration and description of the access device in connection with a sheath (e.g., for micro puncture applications) is merely exemplary of one possible application of the access device.

Figure 1B:
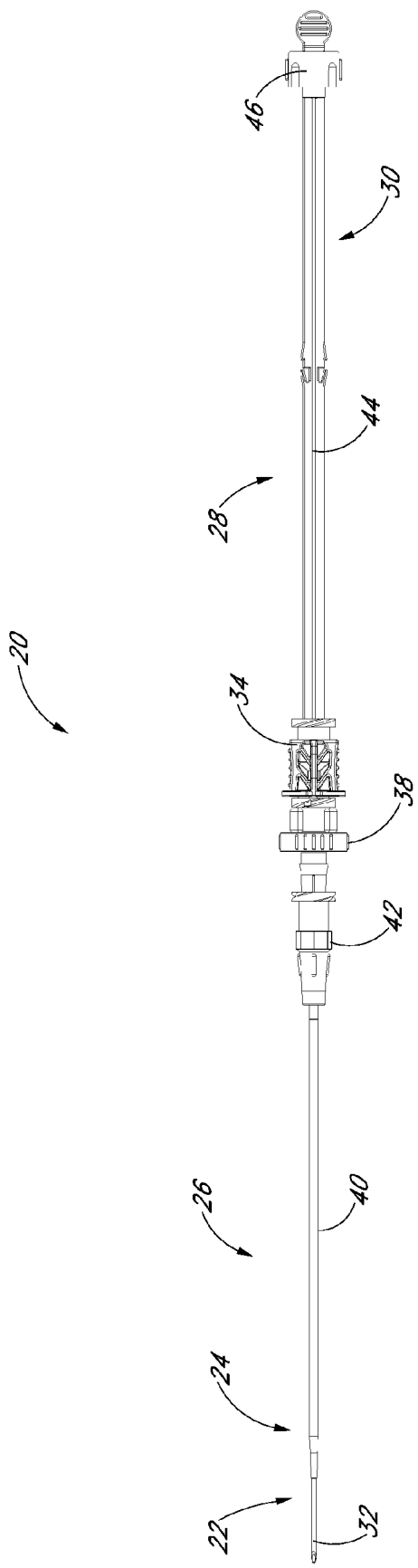
FIG. 1B is a plan view of the embodiment depicted in FIG. 1A.

FIGS. 1A and 1B illustrated a preferred embodiment of an access device 20. The access device 20 comprises a needle 22, a dilator 24, and a sheath 26. In the illustrated embodiment, the access device also includes a guidewire section 28 and a track 30. As best seen in FIG. 1B, the dilator 24 is preferably coaxially mounted on the needle 22, and the sheath 26 is coaxially mounted on the dilator 24. The telescoping nature of the access device's components can also be accomplished by arranging the components with their axes arranged substantially parallel rather than coaxially (e.g., a monorail-type design).

Each of these components includes a luminal fitting at a terminal end or transition (i.e., a hub) and elongated structure that extends from the fitting. Thus, in the illustrated embodiment, the needle 22 includes a needle body 32 that extends distally from the needle hub 34, the dilator 24 includes a dilator shaft 36 that extends distally from a dilator hub 38, and the sheath 26 includes a sheath body 40 that extends distally from a sheath hub 42. The guidewire section 28 comprises a guidewire 44 and preferably a guidewire hub or cap 46. In the illustrated embodiment, the guidewire hub 46 is disposed on the proximal end of the guidewire 44; however, in other applications, the hub 46 can be disposed at a location between the ends of the guidewire 44.

FIGS. 2A-2G illustrate the needle body 32 and needle hub 34 of the needle 22, which are configured in accordance with a preferred embodiment of the access device, in isolation from the other components of the access device 20. As best seen in FIGS. 2A and 2B, the needle hub 34 is disposed on a proximal end of the needle body 32. The needle body 32 terminates at a distal end near a distal portion 50 of the needle 22, and the needle hub 34 lies at a proximal portion 52 of the needle 22.

The needle body 32 preferably has an elongated tubular shape having a circular, constant-diameter inner bore and a circular, constant-diameter exterior surface. In other embodiments, however, the needle body 32 can have other bore and exterior shapes (such as, for example, but without limitation, an oval cross-sectional shape). The interior or exterior of the needle can also include grooves or channels. The grooves or channels may guide fluids within the needle bore either around or to certain structures of the needle 22 or within the needle 22 (e.g., around the guidewire). In some embodiments, the grooves or channels may assist in maintaining a desired orientation of the needle 22 with respect to the dilator.

The needle body 32 has a sufficiently long length to access a targeted subcutaneous body space and has a sufficient gauge size to withstand the insertion forces when accessing the body space without causing undue trauma. For many applications, the needle body can have a length between 3-20 cm, and more preferably between 3-10 cm. For example, to access a body space (e.g., a vessel) in the thorax of an adult human, the needle body 32 preferably has a length of 7 cm or greater, and more preferably has a length of 9 cm or greater, and most preferably has a length of 9 to 10 cm. The size of the needle preferably is 18 gauge or smaller, and more preferably between 18-28 gauge, and most preferably between 18-26 gauge for micro-puncture applications (peripheral IVs). For applications with a neonate, the length and gauge of the needle body 32 should be significantly shorter and smaller, for example preferably between 3-4 cm and between 26-28 gauge.

As best seen in FIGS. 2A and 2D, the needle body 32 includes at least one fenestration or opening 56 near a distal end of the needle body 32. The fenestration 56 extends through the wall of the needle body 32 and can have a variety of shapes and orientations on the needle body 32, as described in detail below. In addition, the needle body 32 can have a bevel tip 54 disposed on the distal portion 50.

As is illustrated in FIGS. 2A and 2B, a fin 58 is preferably disposed at a circumferential location around the needle hub 34 that is aligned with the circumferential locations of the bevel on the needle tip and the opening or fenestration 56 in the needle. That is, the fin 58 is indexed with the bevel and fenestration. During use, the physician or healthcare provider can determine the orientation of the beveled needle tip (and the fenestration 56) by noting the orientation of the exposed fin 58 even though the bevel is inside the vessel and the fenestration is covered by the sheath and/or dilator. For example, in the illustrated embodiment, an orientation of the fin 58 away from the patient coincides with a bevel up orientation of the needle tip within the vessel. The fenestration 56 is also on the same side as the fin 58, as seen in FIG. 2C.

The fin 58 also provides a grasping region to manipulate the needle hub 34. For example, a physician or healthcare provider can place an index finger and thumb on the sides of the fin 58 to stabilize the needle hub 34, relative to the dilator 24 and/or sheath 26. In the illustrated embodiment, as the dilator/sheath slides distally over the needle, the needle hub 34 slides relatively along the track 30 between a first position 121 and a second position 123 (example portions illustrated in FIG. 6A). The fin 58 can be held when performing the insertion step (which will be described below). In addition, the fin 58 can be used to stabilize the needle hub 34 while rotating the dilator hub 38. Furthermore, the fin 58 can be used by a physician or healthcare provider as an aid to grasp the access device 20 when the needle hub 34 is disposed at any position along the track 30.

FIG. 2D is an enlarged view of the side opening or fenestration 56 in the needle body 32. The one or more fenestration 56 provides a path through the side of the needle body 32. The fenestration 56 illustrated in FIG. 2D has an oblong shape. The shape of the side opening 56, however, is not limited to the illustrated embodiment and may be round, oblong, square, or another shape.

With specific reference now to FIGS. 2E-2G, the needle hub 34 preferably includes locking structures at the proximal portion and distal portion of the needle hub 34. These locking structures may be a luer-thread-type or another type of connections.

The locking structure on the proximal portion 52 of the needle hub 34 allows the physician or healthcare provider to secure another medical article to the proximal end of the needle hub 34. For example, the needle hub 34 in the illustrated embodiment includes an annular flange or lip 63. The lip 63 is threaded to allow the needle hub 34 to attach to other medical articles with a corresponding luer-nut locking feature. Additionally, a physician or healthcare provider may attach a syringe or monitoring equipment to the locking structure on the proximal end to perform other procedures as desired. The needle hub 34 can also include a septum at its proximal end and/or a side port if these features are desirably for a particular application.

The locking structure on the distal portion of the needle hub 34 allows the physician or healthcare provider, for example, to lock the needle hub 34 to the dilator hub 38 when the needle hub 34 is in the first position 121. In the illustrated embodiment, the locking structure includes a latch element 66 on the needle hub 34. The latch element 66 releasably locks the needle hub 34 to the dilator hub 38. The locking structure allows the healthcare provider to advance the needle into a patient while grasping the needle hub 34, the dilator hub 38 or both.

As explained below in greater detail, the guidewire 44 is introduced through a hollow portion 62 of the needle hub 34, through the needle body 32, and into a punctured vessel. The guidewire 44 allows the healthcare provider to guide the dilator 24 and sheath 26 into the vessel.

The needle hub 34 may also comprise two tangs 68 that allow the needle hub 34 to slide along the track 30 between a first position 121 and a second position 123. While in the preferred embodiment the two tangs 68 of the needle hub 34 are engaged with the track 30 between the first position 121 and the second position 123, in other embodiments the needle hub 34 is only engaged with the track 30 over a portion of the length of the track 30 between the first position 121 and the second position 123. The sliding interconnection between the track 30 and the needle hub 34 also can be accomplished using other cooperating structures (e.g., a corresponding pin and tail of dovetail connection).

FIG. 3A is a plan view of the dilator 24 of the embodiment depicted in FIG. 1A. FIG. 3B is a cross-sectional view of the dilator 24 of the embodiment depicted in FIG. 3A, taken along line 3B-3B. As shown in FIGS. 3A and 3B, the illustrated dilator 24 comprises a dilator shaft 36, a dilator hub 38, a distal region 70, and a proximal region 72. In the illustrated embodiment, the dilator shaft 36 includes a side openings or fenestrations 74; however, in other embodiments, the dilator shaft 36 can include fewer or greater numbers of fenestrations 74. For example, the dilator shaft 36 may not include a fenestration 74 where a blood flash chamber(s) is disposed within the dilator (as will be described in more detail below).

The dilator hub 38 may comprise one or more vents. In the illustrated embodiments, the vents in the dilator hub 38 are formed by grooves 75. Additionally, the dilator shaft 36 may comprise one or more longitudinal channels formed in the outer surface of the dilator shaft 36. In the illustrated embodiment, the channel is an open channel. The side walls of the open channel are formed by ridges 76. In the illustrated embodiment, the ridges 76 define generally smooth, arcuate exterior surfaces that interface with the sheath 26; however, in other embodiments, the ridges can have other shapes (e.g., can define more pronounced apexes). Once assembled within a sheath body 40, the open channel in the dilator shaft 36 is closed by the inside diameter of the sheath body 40.

Figure 3C:
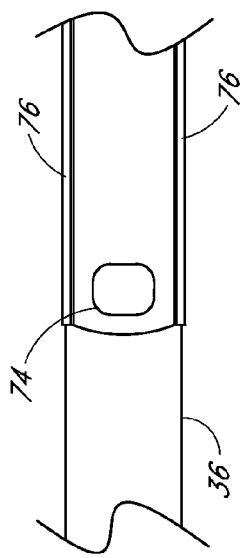
FIG. 3C is an enlarged plan view of a portion of the dilator from FIG. 3A and shows the fenestration and longitudinal channel.

FIG. 3C is an enlarged plan view of a portion of the embodiment illustrated in FIG. 3A. As noted above, the illustrated dilator shaft 36 comprises one or more side openings 74 and one or more channels formed between ridges 76. The side opening or fenestration 74 provides a fluid path through the side of the dilator shaft 36. The shape of the side opening 74 is not limited to the illustrated embodiment and may be round, oblong, square, or have another shape. The opening or fenestration 74 illustrated in FIG. 3C has an oblong shape.

In the illustrated embodiment, the opening 74 in the dilator shaft 36 has an oblong shape with its major axis being non-parallel relative to the major axis of the oblong opening 56 in the needle 22. For example the needle opening 56 may extend in a longitudinal direction and the dilator opening 74 may extend in a circumferential direction or vice versa. In other words, the long axis of the dilator opening 74 is disposed generally perpendicular to the long axis of the needle opening 56. As explained in connection with additional embodiments below, these openings 56, 76 can have other shapes, sizes and orientations that preferably obtain a significant degree of overlap to account for manufacturing tolerances and rotational misalignments. For this reason, it is preferred that one of the fenestrations has a greater dimension in at least one direction than the other one of the fenestrations in the same direction. Accordingly, in the illustrated embodiment, the needle fenestration 56 has a longer longitudinal dimension than the longitudinal dimension of the dilator fenestration 74.

The channel formed between the ridges 76 extends in a proximal direction from a point distal to the opening 74. The ridges 76 in the illustrated embodiment are disposed along the dilator shaft 36 and on opposite sides of the dilator shaft 36 so as to balance the dilator shaft 36 within the sheath. In the illustrated embodiment, the ridges 76 form two channels there between. Balancing the dilator within the sheath allows the dilator to apply equal pressure to the inside circumference of the sheath.

The dilator hub 38 may include locking structures at the proximal region 72 and the distal region of the dilator 24. Each locking structure may be a luer type or other type of connection. In the illustrated embodiment, the dilator hub 38 comprises a first luer connection 78, a second luer connection 80, a lip 77, and a base 79. The first luer connection 78 engages to the needle hub 34 on the needle 22 illustrated in FIG. 2E. The second luer connection 80 is disposed distal to the first luer connection 78. In some embodiments, the second luer connection 80 (e.g., a male luer slip connector) can be configured to engage to the sheath hub 42 (e.g., a female luer slip connector) on the sheath 26 illustrated in FIG. 1A. Additionally, the male-female lure slip connectors on these components can be reversed.

Figure 3D:
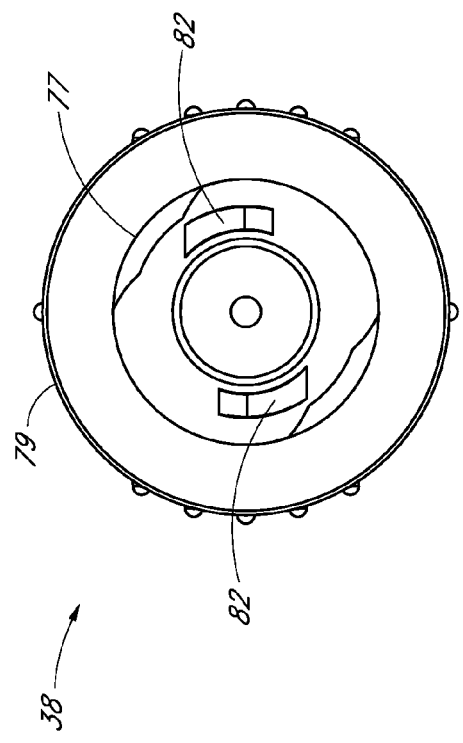
FIG. 3D is an enlarged end view of the dilator hub from FIG. 3A.

FIG. 3D is an enlarged proximal end view of the dilator 24 of FIG. 3A. As shown most clearly in FIG. 3D, the dilator hub 38 comprises an opening 82 that releasably engages the latch element 66 on the needle hub 34 illustrated in FIG. 2E-2F to secure the dilator hub 38 to the needle hub 34 when the needle hub 34 is in the first position 121. Again, the male-female lure slip connectors on the dilator hub and the needle hub 34 can also be reversed in other embodiments.

The color of the dilator 24 may be selected to enhance the contrast between the blood or other fluid and the dilator 24. During blood flash, for example, blood is observed flowing between the dilator 24 and the sheath to confirm proper placement of the needle in a blood vessel. To increase the visibility of the fluid as the fluid flows between the sheath and dilator 24, the sheath is preferably manufactured from a clear or transparent material with the dilator 24 having a color that contrasts with the color of the fluid. For example, the dilator 24 may have a white color to enhance its contrast with red blood. Other colors of dilator 24 could be employed depending on the color of the fluid and the degree of contrast desired. Further, only a portion of the dilator in the region of the blood flash can have the contrasting color with the remainder having a different color. For embodiments that have a channel formed between the needle and dilator 24, the dilator 24 may be manufactured of a clear or transparent material similar to the sheath to allow the physician to observe the blood flash through both the sheath and dilator 24.

Figure 3E:
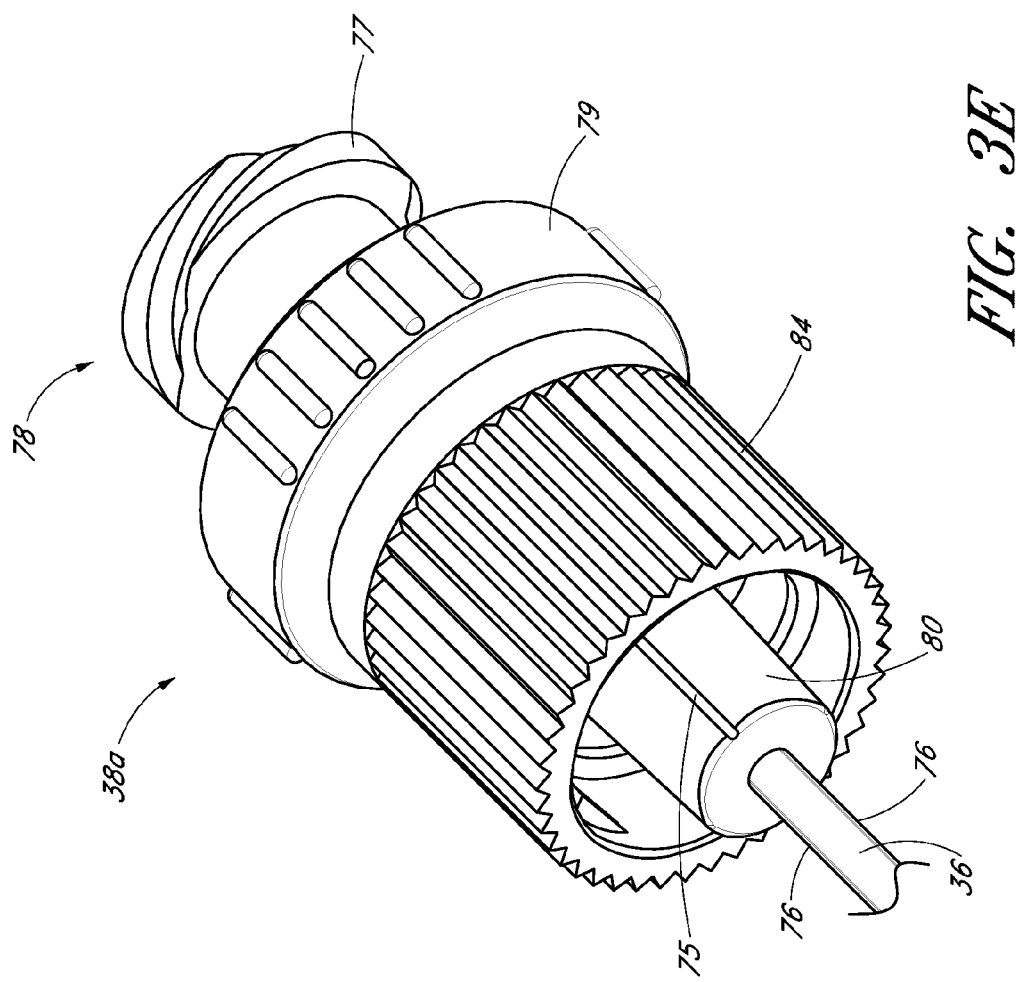
FIG. 3E is a perspective view of another embodiment of the dilator hub that includes a locking spin nut configured to secure to a sheath that has a corresponding screw thread.

FIG. 3E is an enlarged perspective view of another embodiment of a dilator hub 38A. The dilator hub 38A is similar to the dilator hub 38 illustrated in FIG. 3A except that the dilator hub 38A further includes a spin nut or collar 84. The proximal end of the spin nut 84 rotates about an annular groove 73 in the dilator hub 38 (see FIG. 3A). Once disposed within the annular groove 73, the spin nut 84 is inhibited from moving in the distal direction but is free to rotate about the dilator hub 38A. The spin nut 84 can have an interengaging element that locks to a corresponding interengaging element on the sheath 26. In the illustrated embodiment, the spin nut 84 includes an internal thread which engages with an external thread on the sheath hub 42 on the sheath 26 illustrated in FIG. 1A.

The dilator 24 or sheath 26 may separately, or together, form one or more passages to allow air or gas to escape or vent from between the dilator 24 and sheath 26 and/or between the needle and the dilator. The one or more passages may further be sized to inhibit the flow of a liquid, such as blood, while allowing air to pass therethrough. The one or more passages may be in the wall of the sheath 26, the sheath hub, the dilator hub 38, an exposed section of the dilator shaft, and/or formed between adjacent surfaces of the dilator 24 and sheath 26. For example, FIG. 3A shows longitudinally arranged grooves 75 that are formed between adjacent surfaces of the dilator 24 and sheath 26. Such venting passages can also be labyrinth. The adjacent surfaces form a luer slip connection between the sheath 26 and dilator 24.

Figure 3F:
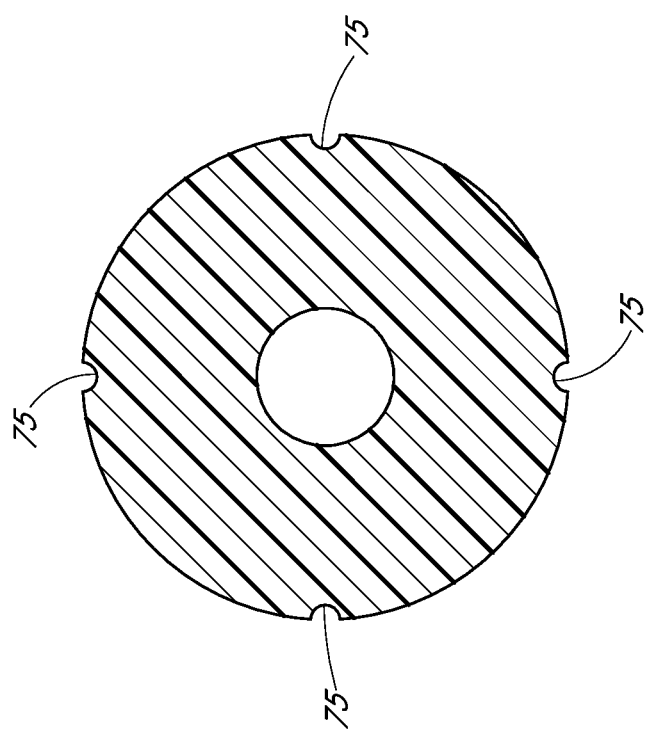
FIG. 3F is a cross-sectional view taken along the lines 3F-3F in FIG. 3A and shows the grooves equally spaced about the circumference of the luer surface.

FIG. 3F is a cross-sectional view taken along lines 3F-3F in FIG. 3A and shows the grooves 75 equally spaced, though not required to be equally spaced, about the circumference of the luer slip surface. The grooves 75 are sized to allow air to escape from between the dilator and the medical article, such as a sheath, when the blood flash occurs. As mentioned above, the one or more passages need not be in the form of a surface groove 75 and instead may be in the form of an opening or passageway.

In the illustrated embodiment, the one or more passages allow air to pass through the luer connection between the sheath and dilator hubs. In the illustrated embodiment, a distal end of the passage 75 is located on the distal side of the luer connection with the proximal end of the passage 75 being located on the proximal side of the luer connection.

The one or more passages may be sized to filter blood or other liquid or may include a filter or other structure that inhibits the passage of a liquid while allowing the passage of air. For example, the sheath itself may include one or more passages in the form of small openings, pores or porous material. Depending on the size of the one or more passages and the expected size of the fluid molecules and formed elements (e.g. red blood cells), the one or more small openings, pores or porous material in the sheath can form a porous vent that allows air to pass yet retain blood.

A method of manufacturing a ridged dilator will now be described. First, an extrusion process is used to create a long tubular body having one or more longitudinal grooves or channels on its outer diameter (OD) or within the substance of the dilator. The long tubular body exceeds the required length of a single dilator and preferably has a length that is many times greater than the length of a single dilator. A manufacturing die is employed in the extrusion process having geometry that reflects the desired geometry for the inside and outside diameters of the dilator and the thickness and circumferential span of the longitudinal grooves or channels or interior channels. In the illustrated embodiment of FIGS. 1-11, the long tubular body includes two longitudinal OD channels on opposite sides of the body to enhance the balance of the dilator within the sheath. However, a single channel can provide a visible indicator for the blood flash. The two channels preferably extend along the length of the extruded tubular body. While the illustrated embodiment includes one or more channel disposed between the dilator and the sheath, one or more channels can in addition or in the alternative be formed between the needle and the dilator, within the dilator, and/or within the sheath. In some embodiments, the dilator 24 thus is made partially or completely from clear, translucent, transparent, or semi-opaque material to visualize the fluid flash within the channel.

With reference back to the illustrated embodiment, the extruded tubular body is cut to the appropriate length for a single dilator. In the preferred method, the two OD grooves extend for the entire length of the cut dilator.

A tipping process is then employed on an end of the cut dilator to reform the tip. An end of the cut dilator is forced into a die/mandrel having geometry that matches the desired geometry of the tip of the finished dilator. The desired geometry is selected depending on, for example, the inside diameter of the sheath. It is desirable for the sheath and dilator to form a close fit or seal near the tip to promote blood flow in the proximal direction up the channel formed between the grooved dilator and sheath. Preferably, the OD of the dilator in the tip region tapers in the distal direction.

When in the die/mandrel, thermal energy is applied to the tip to reform the tip to match the die/mandrel. The thermal energy may be applied by any known technique, including using radiant heating from an infrared or RF heat source. As part of the tipping process, the dilator in the tip region is reformed so that the grooves are essentially removed. With the grooves removed, the dilator is able to form the close fit or seal with the sheath near the tip. The grooves are maintained along the remainder of the dilator on the proximal side of the location where the tip of the sheath 26 sits on the dilator. After removal from the die/mandrel, the tip end of the dilator may be cleaned and cut as necessary to remove any manufacturing remnants.

The one or more fenestrations in the dilator is cut through the dilator near the tip region and in or near the groove. Each fenestration may be cut by any known means, including a drill or laser. Further, the cutting device may be moved with respect to the dilator or vice versa to achieve an oblong or other shape for the fenestration.

The end of the dilator opposite from the tip end can be flared to facilitate over molding the dilator hub onto the dilator.

Figure 4D:
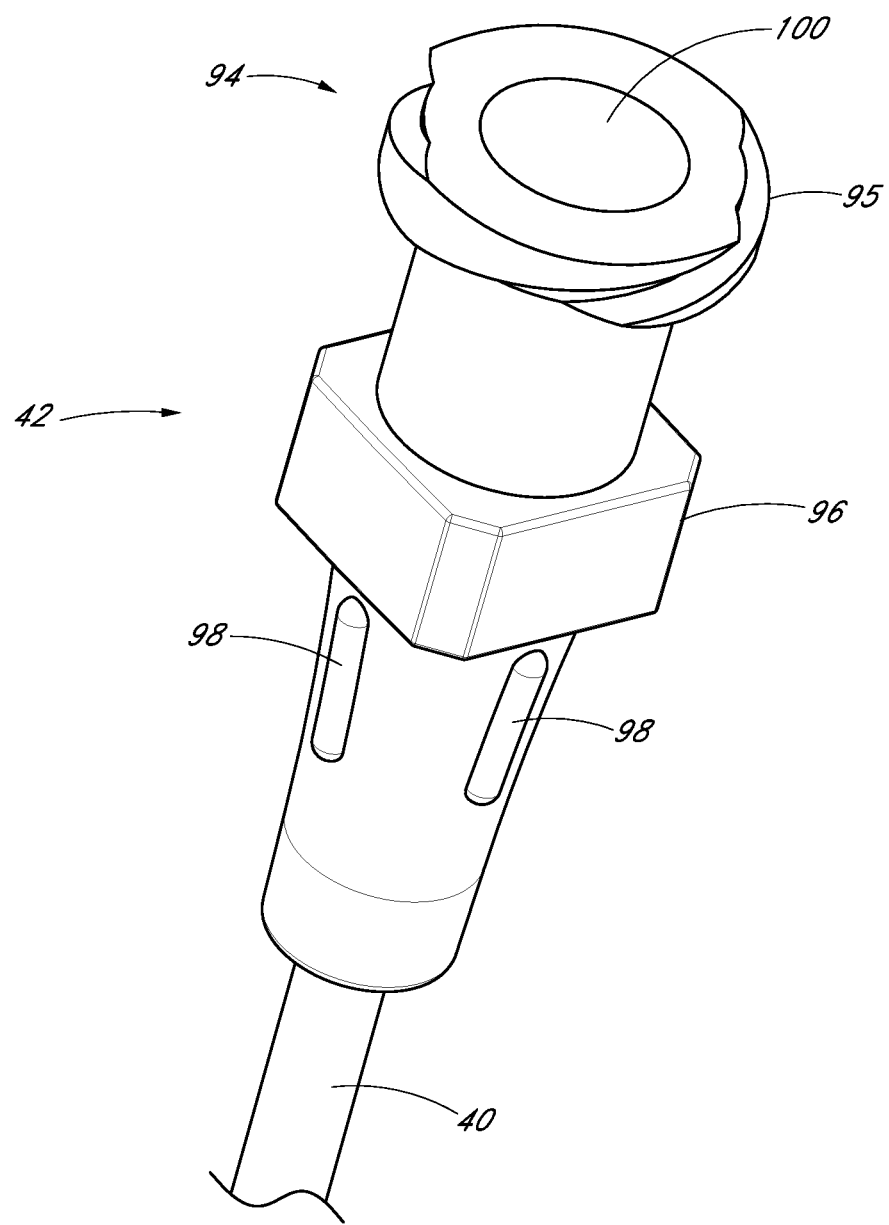
FIG. 4D is an enlarged perspective view of a proximal portion of the sheath from FIG. 4A.

FIG. 4A is a plan view of the sheath 26 of the embodiment depicted in FIG. 1A. FIG. 4B is a cross-sectional view of the sheath 26 of the embodiment depicted in FIG. 4A, taken along line 4B-4B. FIG. 4C is an enlarged proximal end view of the sheath 26 of FIG. 4A. FIG. 4D is an enlarged perspective view of the sheath hub 42 of the sheath 26 of FIG. 4A. As shown in FIGS. 4A-4D, the sheath 26 may comprise a sheath body 40, a sheath hub 42, a distal portion 90, and a proximal region 92. The sheath body 40 may be made partially or completely from clear, translucent, transparent, or semi-opaque material. The sheath body 40 can also include one or more radio opaque markers, such as, for example, barium sulfate stripes. In a preferred embodiment, the sheath includes two such radio opaque stripes disposed on diametrically opposite sides of the body 40.

The sheath body 40 may be a single piece sheath through which a catheter or other medical article (e.g., a guidewire) is inserted into the vessel. In such an embodiment, the sheath body 40 forms a conduit for insertion of the catheter or other medical article (e.g., a guidewire). In addition to providing a conduit, the sheath or a portion of the sheath can form a lumen that is in addition to the lumen(s) of the catheter. For example, an equivalent to a triple lumen catheter can be formed by inserting a dual lumen catheter through the sheath body 40 with the sheath body 40 itself forming a third lumen.

It may be advantageous to remove a portion or the entire sheath body 40 depending on the type of catheter or medical article that is to be inserted into the vessel after employing the access device 20. For example, after the catheter or other medical article is inserted into the vessel, a portion of the sheath body 40 can be separated or peeled-away and removed. A peel-away sheath can include perforations, serrations, skives, or other structures, or include other materials (e.g., PTFE with bismuth) to allow the physician or healthcare provider to remove easily a portion or the entire sheath body 40.

The sheath hub 42 may include a luer slip connection and a lock member 94. The locking member 94 may comprise a locking or attaching structure that mates or engages with a corresponding structure. For example, the lock member 94 can be a luer connection 94 which can be configured to engage with the second luer connection 80 of the dilator hub 38.

The sheath hub 42, as best seen in FIGS. 4C and 4D, preferably is designed so that the locking mechanism or second luer connection 80 of the dilator hub 38 can enter the sheath hub 42 substantially unobstructed. However, in use, once the sheath hub 53 is placed at a desired location over the dilator shaft 36, the physician or healthcare provider can push, pull, or twist the sheath hub 42 and possibly disengage or engage the locking member 94 with a corresponding connector on another medical article. The locking member 94 can be, for example, a luer connection, a protruding bump, dent, etc., that creates a mechanical fit so that the dilator hub 38 and the sheath hub 42 are releasably interlocked. In the illustrated embodiment, the locking member 94 of the sheath hub 42 comprises a luer connection. The sheath hub 42 preferably engages with the corresponding second luer connection 80 on the dilator hub 38. Preferably, the locked position can be disengaged or engaged by pulling, squeezing, pushing or twisting the dilator hub 38 relative to the sheath hub 42.

In some embodiments, the sheath hub 42 can comprise a lip 95. The lip 95 can be threaded to allow the sheath hub 42 to attach to other medical articles with a corresponding locking feature.

The sheath hub 42 preferably comprises one or more surface features to allow the physician or healthcare provider to easily grasp or manipulate the sheath 26 and/or access device 20. In the illustrated embodiment, the sheath hub 42 includes a squared grip 96 and ridges 98.

In additional embodiments, the sheath hub 42 may comprise radially extending wings or handle structures to allow for easy release and removal of the sheath body 40 from other parts of the access device 20. In some applications, the wings are sized to provide the healthcare provider with leverage for breaking apart the sheath hub 42. For example, the sheath hub 42 may comprise a thin membrane connecting the halves of the sheath hub 42. The membrane is sized to keep the halves of the sheath hub 42 together until the healthcare provider decides to remove the sheath hub 42 from the access device. The healthcare provider manipulates the wings to break the membrane and separate the sheath hub 42 into removable halves.

FIG. 5A is a perspective view of the guidewire section 28 of the embodiment depicted in FIG. 1A. FIG. 5B is a plan view of the guidewire section 28 depicted in FIG. 5A, which preferably includes the guidewire hub 46. The guidewire hub 46 can comprise one or more surface features to allow the physician or healthcare provider to easily grasp or manipulate the guidewire hub 46 and/or access device 20. In the illustrated embodiment, the guidewire hub 46 comprises one or more ridges 110. In a pre-loaded state, the outer surface of the guidewire hub 46 engages with a locking mechanism 130 on the track 30 when the guidewire hub 46 is in a third position 125 (example third position illustrated in FIG. 6A).

In some embodiments, the guidewire 44 may form a close fit with the inside diameter of the needle body so as to provide a self-aspirating function when retracted. For example, an outside diameter of the guidewire 44 may be selected to form a close fit with the needle along the length of the guide wire or along only a portion of the guidewire 44.

In some embodiments, the distal end portion of the guidewire can have a reduced diameter in comparison to other sections of the guidewire. The size of such reduced diameter section can be selected to permit fluid to pass to the fenestration 56 in the needle body even when the guidewire has been advanced beyond the distal tip of the needle.

Figure 6A:
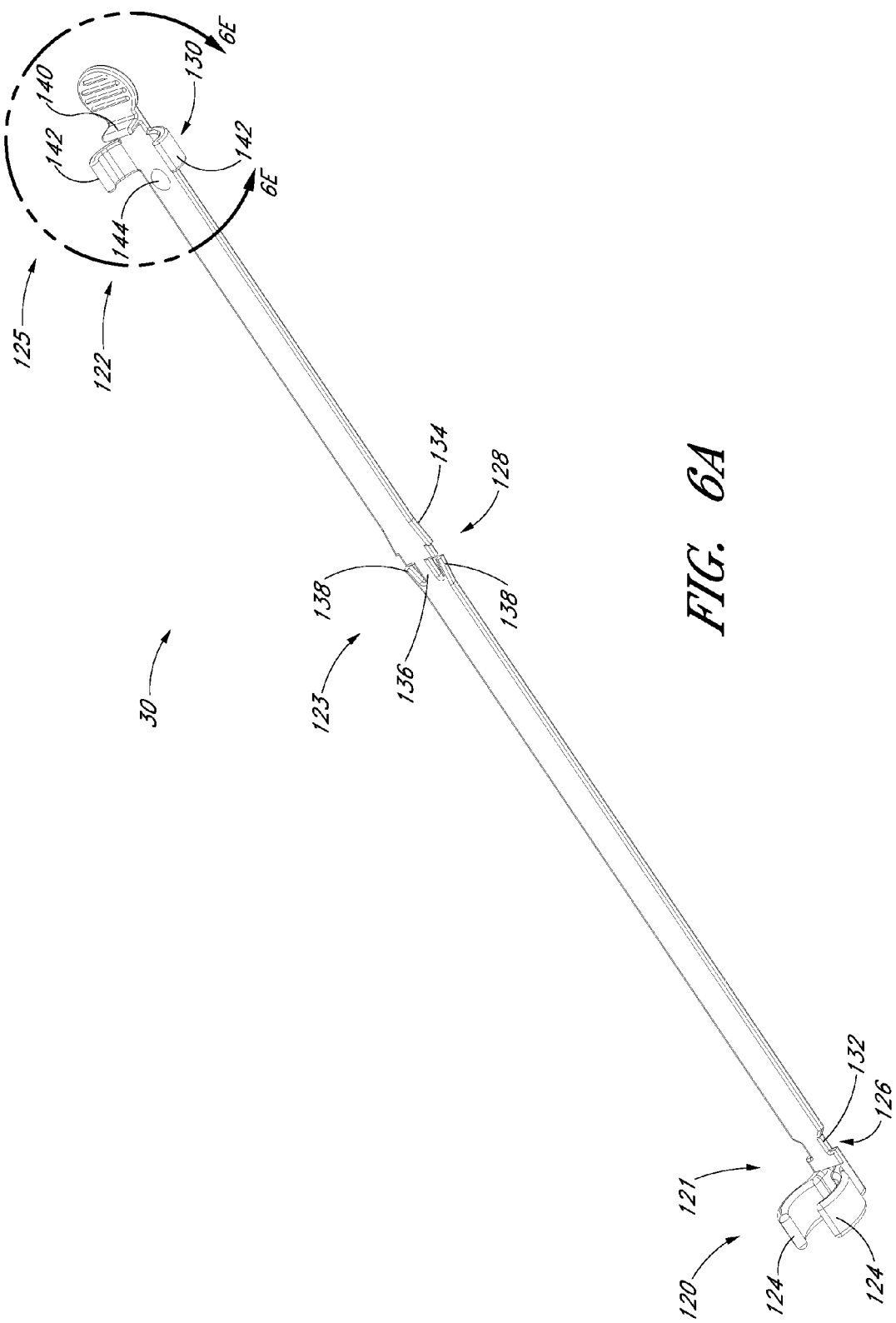
FIG. 6A is a perspective view of a track from FIG. 1A.

FIG. 6A is a perspective view of the track 30 of the embodiment depicted in FIG. 1A. FIG. 6B is a plan view of the track 30 illustrated in FIG. 6A. FIG. 6C is a side view of the track 30 illustrated in FIG. 6A. As shown in FIGS. 6A-6C, the track 30 in the illustrated embodiment comprises a distal portion 120, a proximal portion 122, a distal locking member 124 that connects the track to the dilator hub 38, a locking mechanism 128 that inhibits further proximal and distal movement of the needle hub 34 once the needle hub 34 is slid from the first position 121 to the second position 123 along the track 30, and a locking mechanism 130 that allows the guidewire hub 46 to attach to the track 30 when the guidewire hub is in the pre-loaded state or third position 125. Preferably, the track is made of polycarbonate material; however, as explained below, other materials can be used.

The track 30 may further include a track section 132 of reduced width as shown most clearly in FIGS. 6A and 6B. The reduced width facilitates assembly of the needle hub to the track 30. The illustrated embodiment includes a rib 133 on the distal portion 120 of the track 30. The rib 133 provides additional structural reinforcement between the distal locking member 124 and the remainder of the track 30.

As illustrated in FIG. 1A, the distal locking member 124 connects to the dilator 24 and allows the track 30 to extend proximally from the dilator 24. For example, the locking member 124 can comprise two curved arms 124 that connect to the dilator hub 38 between the dilator hub lip 77 and the dilator hub base 79. The locking member 124 limits movement of the track 30 in a distal or proximal direction relative to the dilator hub 38 but allows the track to rotate freely around the dilator hub 38.

Figure 6E:
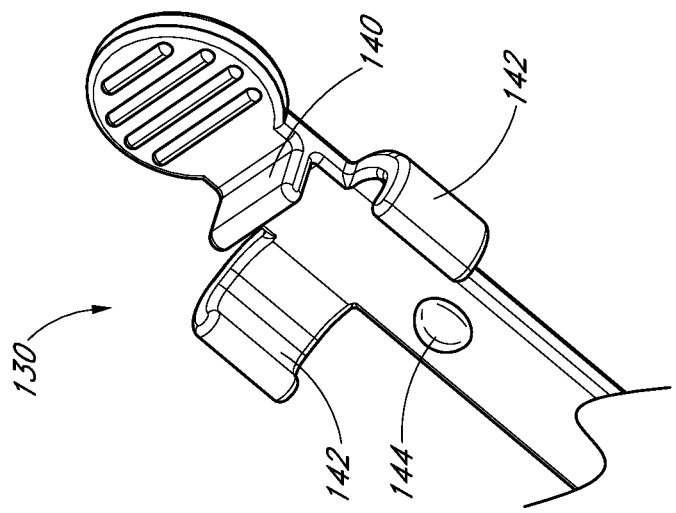
FIG. 6E is an enlarged view of another locking mechanism that locks the guidewire section in a pre-loaded state.
Figure 6D:
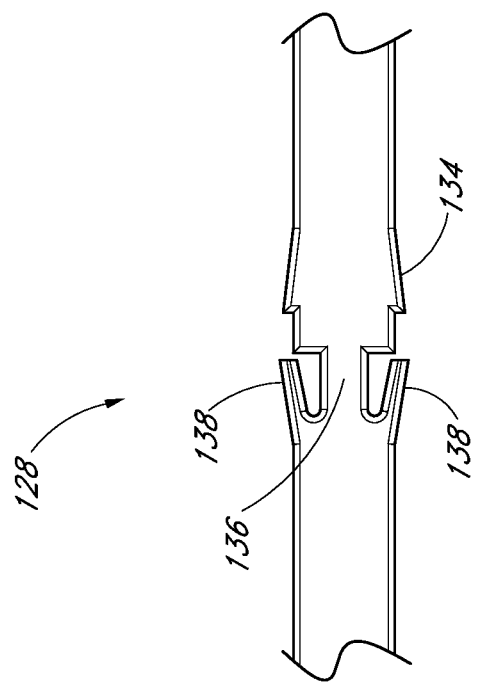
FIG. 6D an enlarged view of the locking mechanism from FIG. 6B.

FIG. 6D is an enlarged view of a portion of the embodiment depicted in FIG. 6B. As shown, the locking mechanism 128 is formed by varying the width of the track in the region of the second position 123. For example, the illustrated embodiment includes a track section 134 of increasing width in the distal direction, a track section 136 of reduced width distal to the track section 134 of increasing width, and two finger elements 138. The two finger elements 138 project from the distal end of the track section 136 toward the proximal end of the track 30 and flare away from the longitudinal axis of the track 30.

FIG. 6E is an enlarged view of a portion of the embodiment depicted in FIG. 6B. The locking mechanism 130 is formed by a clip, clasp or other structure that engages with a portion of the guidewire hub or with a portion of the track 30 when the guidewire hub is in the third position. Some or all of the engagement structure may be part of the track 30, be part of the guidewire hub, or be split between the track 30 and guidewire hub. In the illustrated embodiment, the locking mechanism 130 extends from the track 30 and engages with the guidewire hub. The locking mechanism 130 comprises a rectangular element 140 protruding from the track 30, two track arms 142 projecting from the track 30 distal to the rectangular element 140, and a stop 144 protruding from the track 30 distal to the track arms 142.

In the illustrated embodiment, the locking mechanism between the needle hub and the dilator resides on the proximal side of the dilator hub. In other embodiments, however, the locking mechanism can be disposed at other locations as well. For example, where the locking mechanism includes two pivotal levers which are joined by a locking hinge, the locking mechanism can be disposed radially relative to the needle hub. In such an embodiment, one lever is pivotally coupled to the dilator and the other lever is pivotally coupled to the needle. When the needle hub is moved away from the dilator hub, the levers straighten to a point where the hinge locks. A similar effect can be obtained by a tether limiting proximal movement of the needle hub relative to the dilator beyond a particular point, thereby locking the components together. In a further embodiment, an elongated structure can extend parallel to the needle body from the needle hub within the dilator. Once the needle hub is moved a sufficient distance away from the dilator, additional structure of the locking mechanism (e.g., a detent) engages the elongated structure to inhibit further movement of the needle relative to the dilator. Accordingly, as illustrated by these additional embodiments, the locking mechanism operating between the needle and the dilator can be disposed at a variety of locations relative to the dilator hub.

Figure 7A:
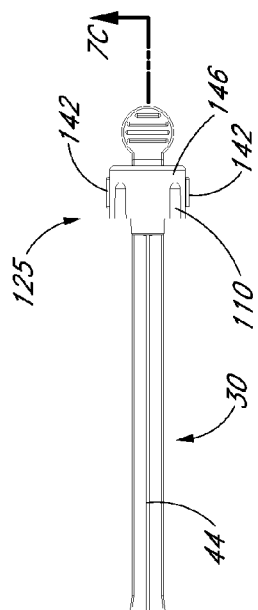
FIG. 7A is a plan view of the access device from FIG. 1A and shows the locking mechanism from FIG. 6E with the guidewire section locked to the track in the pre-loaded state.
Figure 7B:
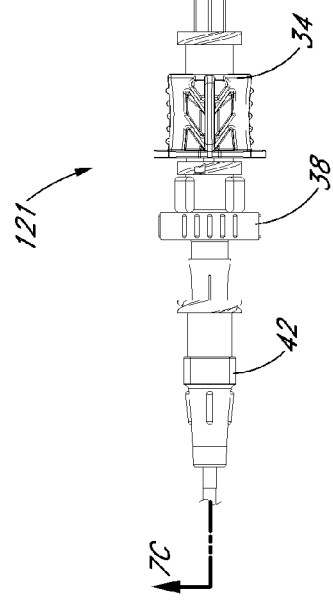
FIG. 7B is a side view of the access device and locking mechanism from FIG. 7A.
Figure 7C:
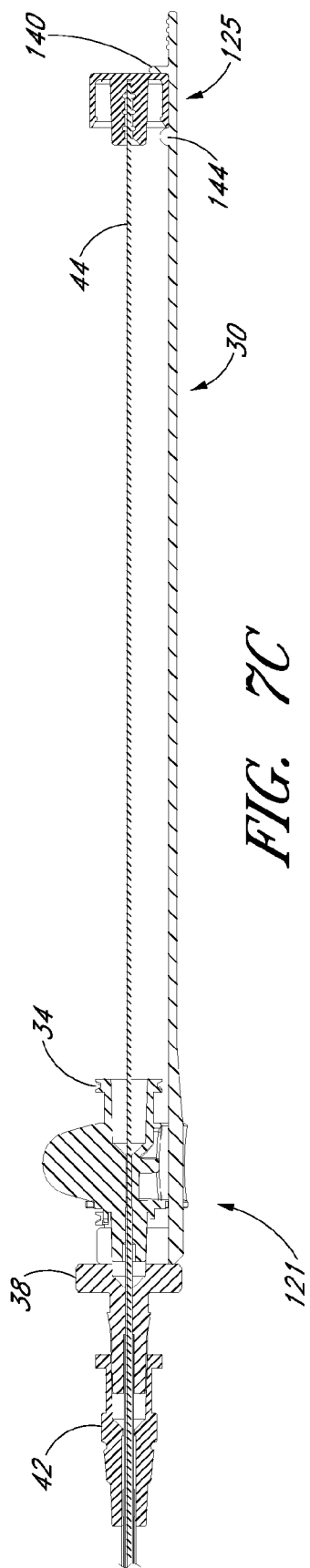
FIG. 7C is a cross-sectional view through the access device of FIG. 7A and shows the guidewire hub disposed between an element and stop of the track.
Figure 7D:
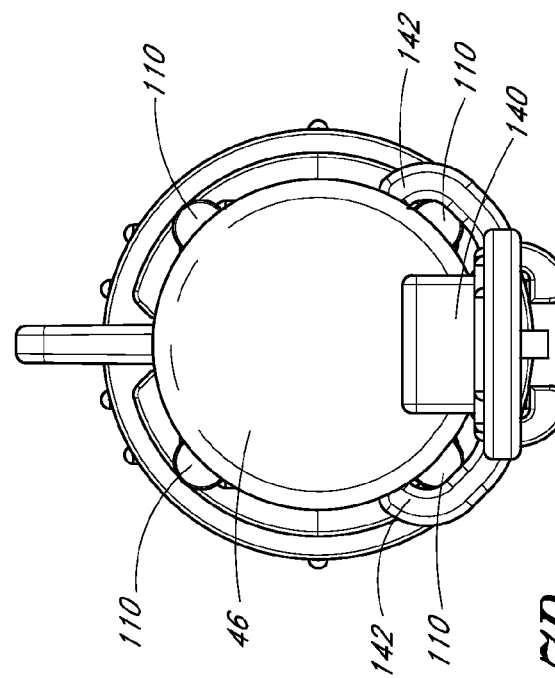
FIG. 7D is an enlarged end view of the access device from FIG. 7B and shows two arms extending from the track and around at least a portion of the guidewire hub.

FIG. 7A is an enlarged plan view of the access device of the embodiment depicted in FIG. 1A pre-loaded with the guidewire. FIG. 7B is a side view of the embodiment depicted in FIG. 7A. FIG. 7C is a cross-sectional view of the embodiment depicted in FIG. 7A along line 7C-7C. FIG. 7D is a proximal end view of the access device 20 of FIG. 7A. In this pre-loaded state, the guidewire hub 46 is locked to the track 30 when the guidewire hub 46 is located in a third position 125. In this position, the guidewire hub 46 can be secured to the track 30 between the rectangular element 140 and the stop 144. For example, the guidewire hub 46 can releasably lock between the rectangular element 140 and the stop 144. In addition, the track arms 142 can further secure the guidewire hub 46 to the track 30. This locking mechanism can arrest unintended rotational and axial movement of the guidewire 44 at least in the distal direction when the guidewire hub 46 is in the third position 125. Of course, the healthcare provider may disengage the guidewire hub 46 from the track 30 to allow distal movement of the guidewire through the access device 20.

In the preloaded-state illustrated in FIGS. 7A-7C, the needle hub 34 is locked to the dilator hub 38 when the needle hub 34 is in the first position 121. Preferably, in the locked position, the openings or fenestrations in the needle and dilator are in register or in alignment with each other. When locked, the needle 22 and the dilator 24 are inhibited from at least unintentional rotational and axial movement relative to each other. By preventing unintentional rotation of the dilator hub with respect to the needle 34, the fenestrations or openings maintain their general alignment.

In the pre-loaded state, the dilator hub 38 is secured to the sheath hub 42. This can inhibit at least unintentional rotational and axial movement between the dilator 24 and the sheath 26. In embodiments where the sheath hub 42 and the dilator 24 have only a luer slip connection, the dilator 24 and sheath hub 42 may rotate relative to each other.

Figure 8A:
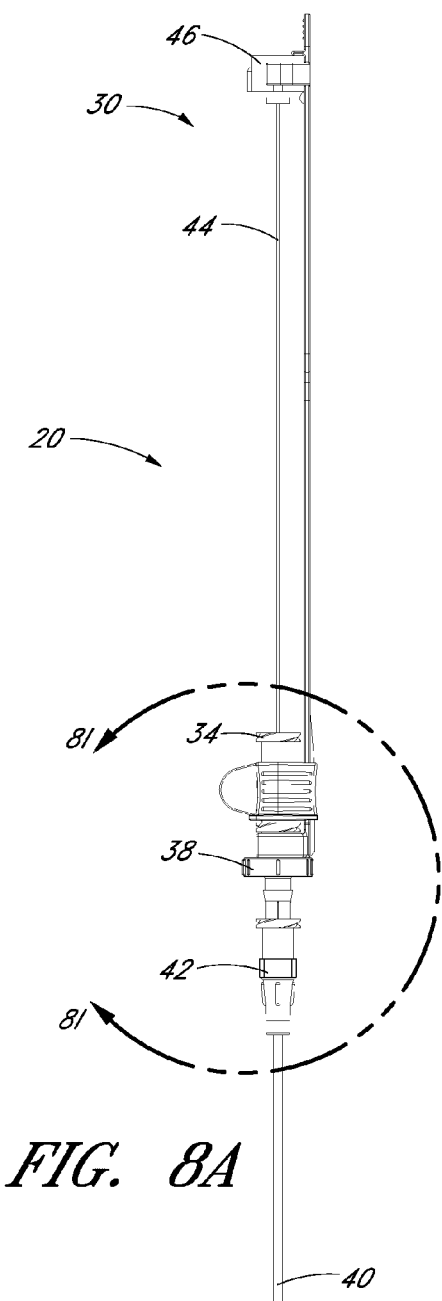
FIG. 8A is a plan view of the embodiment depicted in FIG. 1A illustrating the insertion of the distal end of the access device into a patient.

FIG. 8A is a plan view of the embodiment depicted in FIG. 1A that illustrates an operational step of one method of using the access device 20. FIG. 8A depicts the needle body 32 of the access device 20 inserted into a vessel 148, such as a vein. While the described method refers to vascular access, the access device 20 also can be used to access and place a catheter or sheath into other locations within a patient's body (e.g., for draining an abscess) and for other purposes.

Figure 8B:
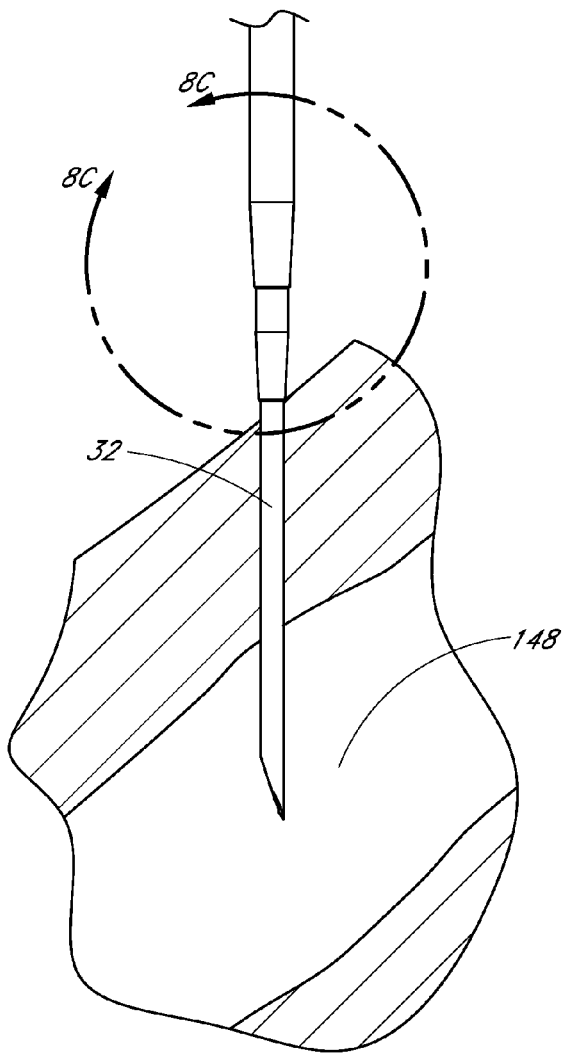
FIG. 8B is an enlarged view of the embodiment depicted in FIG. 8A focusing on the area of the access device adjacent to the patient.

FIG. 8B is an enlarged plan view of the portion of the embodiment illustrated in FIG. 8A which is circled by line 8B-8B. FIG. 8C is an enlarged plan view of the portion of the embodiment illustrated in FIG. 8B which is circled by line 8C-8C. FIG. 8D is an enlarged cross-sectional view of the embodiment depicted in FIG. 8C along line 8D-8D.

As noted above, the needle body 32 comprises one or more side openings 56 in its side wall. The dilator shaft 36 comprises one or more side openings 74. The side openings 56, 74 may have the same or different shapes as well as aspect ratios. In the illustrated embodiment, the side opening 56 in the needle body 32 has a different aspect ratio than the side opening 74 in the dilator shaft 36. The side opening 56 in the needle body 32 is elongated in one direction (e.g., substantially parallel to the longitudinal axis of the needle body 32).

The side opening 74 in the dilator shaft 36 is elongated in a different direction (e.g., along the circumference of the dilator shaft 36). Having offset elongated openings 56, 74 in the needle body 32 and the dilator shaft 36 increases the likelihood that the openings 56, 74 in the needle body 32 and dilator shaft 36 will be sufficiently aligned so that blood flows through the needle side opening 56 and dilator side opening 74. FIGS. 8A-D illustrate the alignment between only one set of corresponding side openings. Other sets of side openings can also be aligned or be misaligned depending upon the relative orientations of the needle body 32 and the dilator shaft 36.

In the illustrated embodiment, the dilator shaft 36 is coaxially positioned to minimize an annular space 150 between the needle body 32 and the dilator shaft 36. The inner surface 152 of the dilator shaft 36 need not, though it can, lie directly against the outer-surface 154 of the needle body 32. Preferably, in this embodiment, the annular space 150 between the outer-surface 154 of the needle body 32 and the inner surface 152 of the dilator shaft 36 is minimized to inhibit the flow of blood or its constituents (or other bodily fluids) into the annular space 150 between the dilator shaft 36 and needle body 32. Advantageously, this feature minimizes the blood's exposure to multiple external surfaces and reduces the risk of contamination, infection, and clotting.

As illustrated in FIG. 8A, the dilator shaft 36 is coaxially mounted to the needle body 32 such that at least part of one side opening 56 disposed on the needle body 32 is rotationally aligned with at least part of one side opening 74 on the dilator shaft 36. Preferably, the needle body 32 and dilator shaft 36 maintain rotational alignment so that blood flows through the needle side opening 56 and dilator side opening 74.

The sheath body 40, as noted previously, is preferably made partially or completely from clear, semi-opaque, translucent, or transparent material so that when blood flows into the needle body 32, (1) through the needle side opening 56, (2) through the dilator side opening 74, and (3) into a channel 156, the physician or healthcare provider can see the blood. In some modes, the channel 156 is formed between the dilator shaft 36 and the sheath body 40 and defined by one or more ridges 76 on the dilator shaft 36. In some modes, the channel 156 is formed within a wall of the dilator shaft 36 with the dilator shaft 36 preferably comprising a transparent material. Blood will indicate to the physician or healthcare provider that the bevel tip 54 of the needle body 32 has punctured a vessel 148.

In some embodiments, the needle body 32 and dilator shaft 36 may (both) have multiple side openings where some or all of these side openings can be rotationally aligned.

The channel 156 can have an axial length that is almost coextensive with the length of the sheath 26. In other embodiments, the channel 156 can be significantly smaller than the elongated channel 156 just described. For example, but without limitation, the channel 156 can be disposed within a distal, mid and/or proximal portion(s) of the sheath 26. The channel 156 alternatively can have a linear, curved or spiral shape along an axial length of the sheath 26 or can be formed by a plurality of such shapes. The channel 156 may have various thicknesses and span angles. The thickness of the channel 156 can range from almost close to zero to 0.010 inches. Preferably, the channel 156 has a thickness of about 0.0005 to about 0.003 inches. More preferably, the channel 156 can have a thickness of about 0.001 inches to about 0.002 inches. The channel 156 can have a span angle Φ about the axis of the dilator 24 of about 30 degrees to about 210 degrees or more, but preferably less than 360 degrees. More preferably, the channel 156 can have a span angle Φ of about 60 to 150. In the illustrated embodiment, the channel 156 spans 120 degrees. The thickness and span angle Φ can be chosen so as to optimize the capillary action that occurs within the channel 156 as fluid (e.g., whole blood) enters the channel 156 as may further be selected based on the expected pressure in the body cavity and viscosity of the liquid.

Figure 8E:
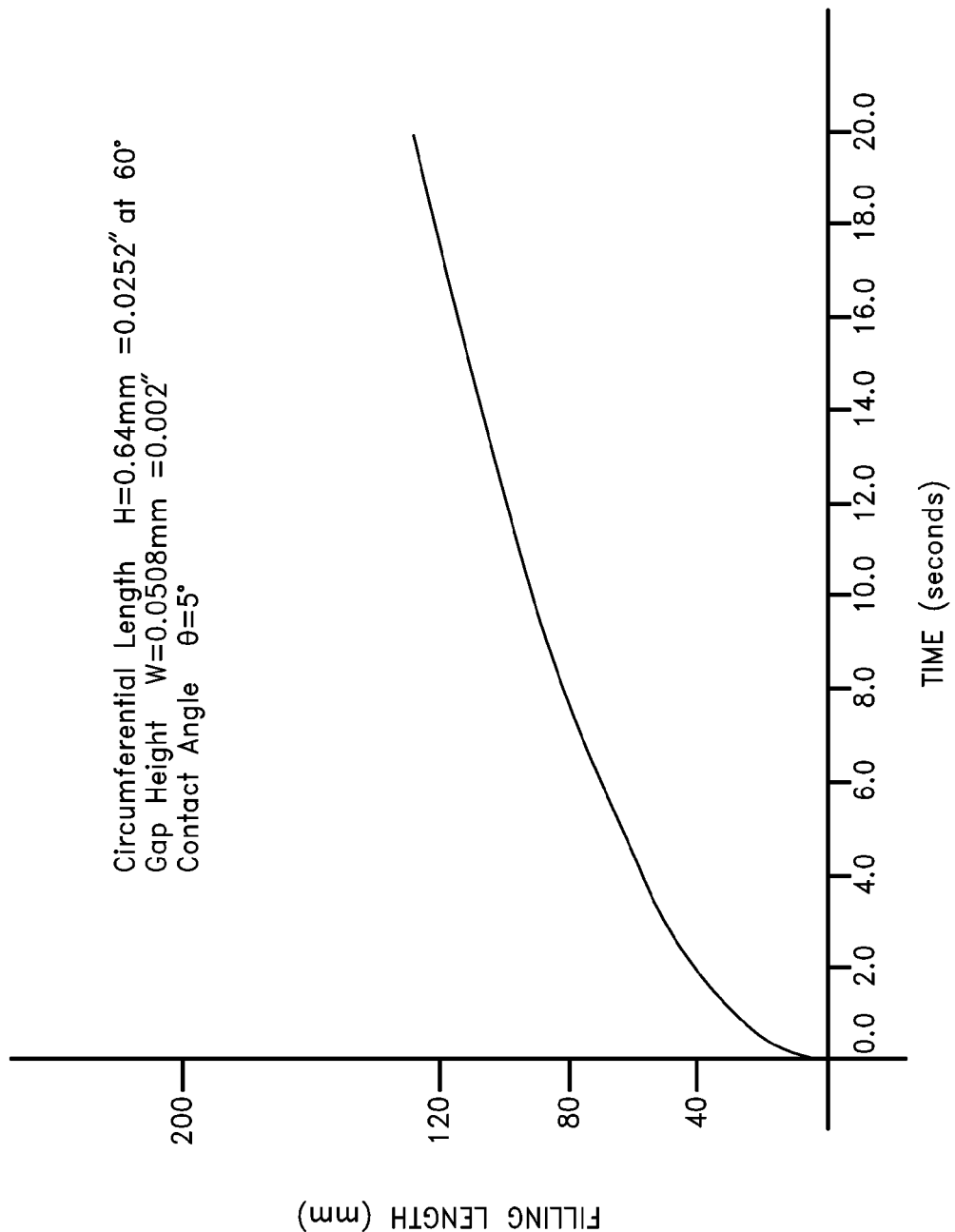
FIG. 8E is a graph showing the rate fluid is drawn up a channel with a gap height width of 0.002 inches.
Figure 8F:
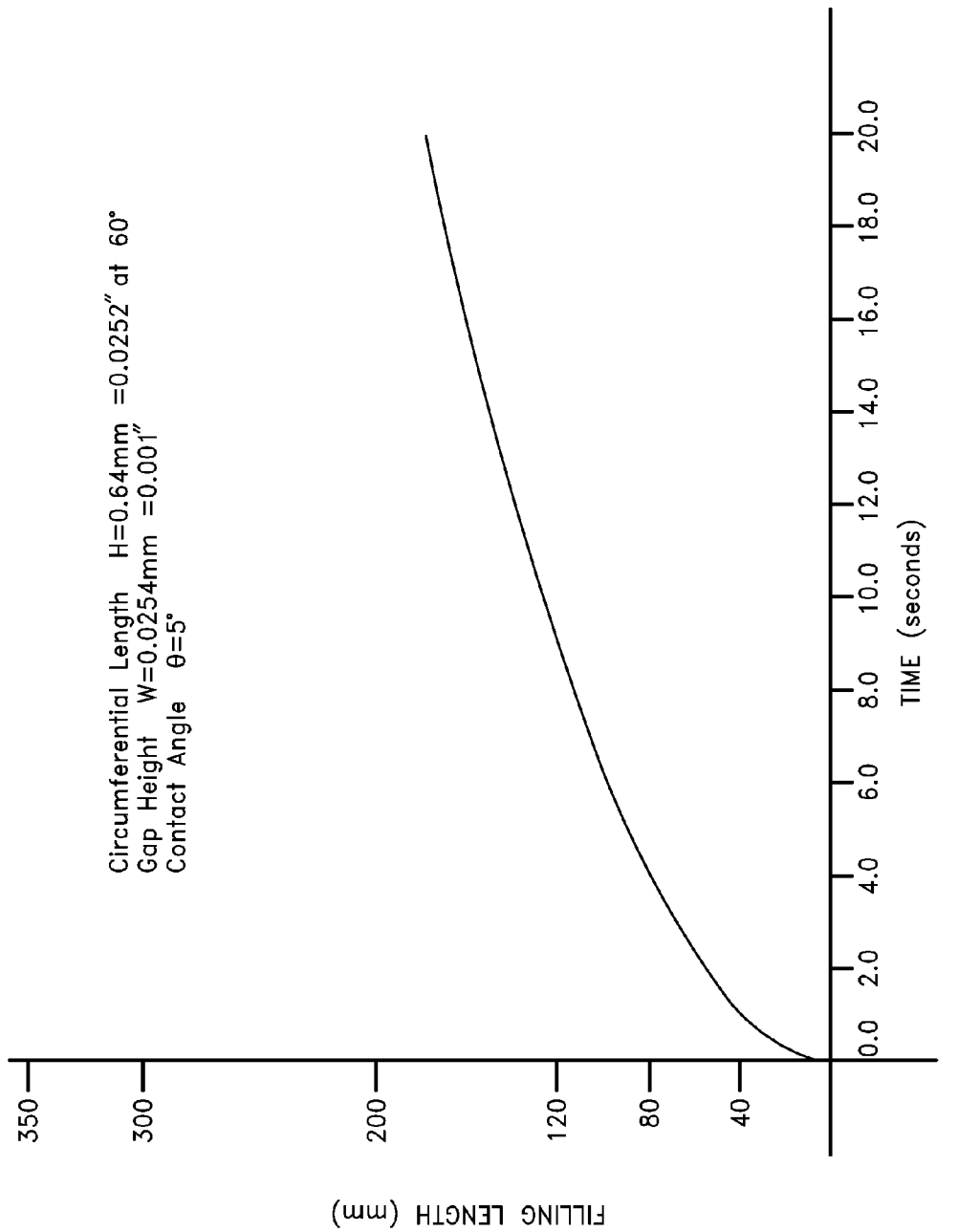
FIG. 8F is a graph showing the rate fluid is drawn up a channel with a gap height width of 0.001 inches.
Figure 8G:
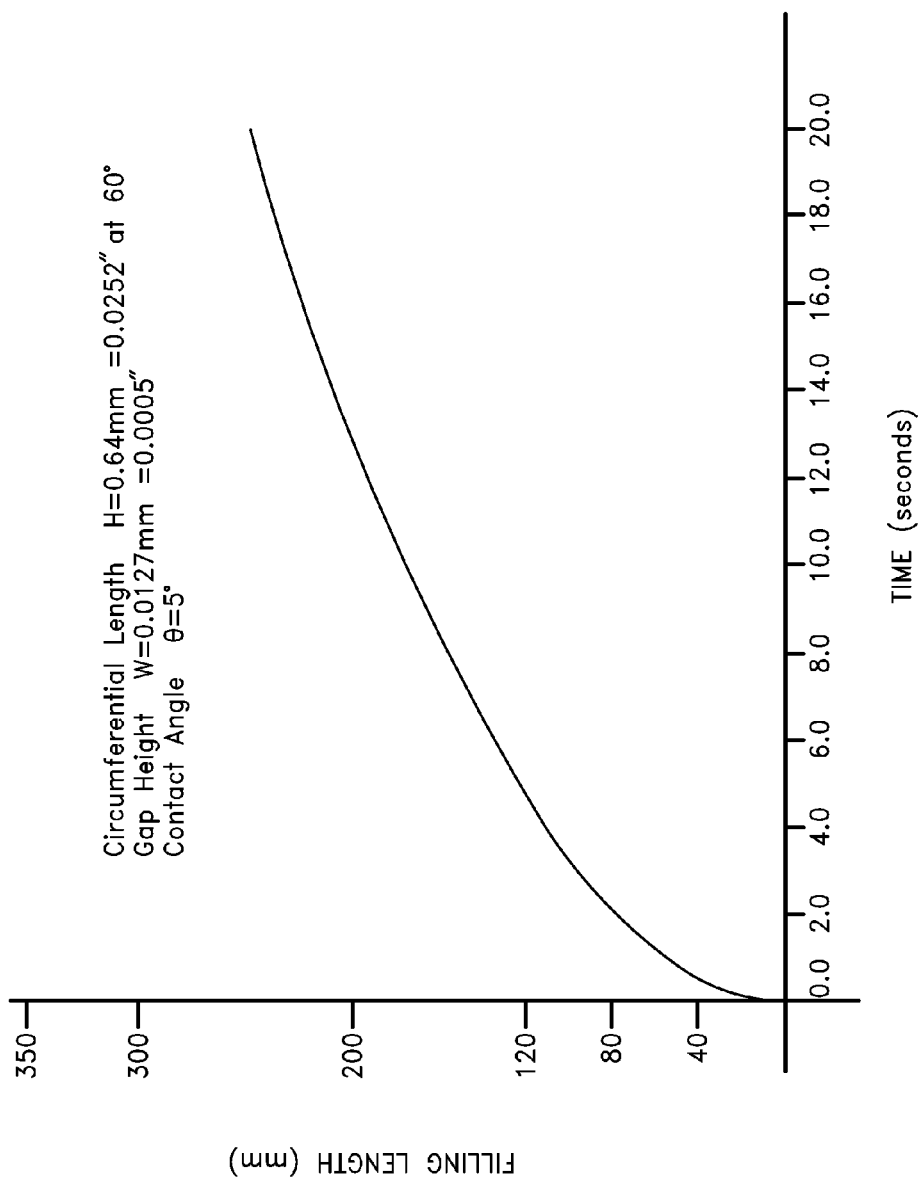
FIG. 8G is a graph showing the rate fluid is drawn up a channel with a gap height width of 0.0005 inches.

FIGS. 8E-8G are graphs of test data illustrating how quickly a fluid is drawn up the surfaces of the channel 156 when the span angle is 120 degrees, the contact angle (θ) is 5 degrees, and the circumferential length (H) is 0.64 mm at 60 degrees. On each graph, the filling length (mm) is plotted on the y-axis, and time (seconds) is plotted on the x-axis. The tests were performed at hydrodynamic pressures similar to pressures experienced in peripheral vessels. FIG. 8E illustrates the rate fluid is drawn up a channel 156 with a gap height width of 0.002 inches, FIG. 8F illustrates the rate fluid is drawn up a channel 156 with a gap height width of 0.001 inches, and FIG. 8G illustrates the rate fluid is drawn up a channel 156 with a gap height width of 0.0005 inches. As shown in FIGS. 8E-G, fluid is drawn up the fastest in a channel with a gap height width of 0.0005 inches, followed by a channel with a gap height width of 0.001 inches, followed by a channel with a gap height width of 0.002 inches.

The shape of the channel 156 described above and the resulting capillary action was optimized for use with whole blood as opposed to other fluids having a different viscosity than whole blood (e.g. leukocytes, pus, urine, plasma). However, the shape of the channel 156 is not limited to the disclosed shape and may be optimized for draining other liquids, such as pus. Further, the shape of the channel 156 described above was optimized for peripherally located vessels where the pressure in the vessel enhances the capillary action and resulting blood flash as well as for vessels located in the regions where the pressure may be low. For example, in the thorax region of the body, the expected pressure in the veins may be lower than in a peripherally located vein when the patient breathes. A different size of the channel for use of the access device 20 in other regions of the body may be employed taking into account the expected pressure within the vessel or body cavity.

Additionally, an outer-surface 160 of the dilator shaft 36 and/or an inner surface 158 of the sheath body 40 can be coated with a substance to promote or enhance the capillary action within the channel 156. For example a hydrophilic substance can be used to coat outer-surface 160 of the dilator shaft 36 and/or the inner surface 158 of the sheath body 40 to enhance capillary action. As another example, a surfactant can be used to coat the outer-surface 160 of the dilator shaft 36 and the inner surface 158 of the sheath body 40. One example of a surfactant that can be used is Lutrol 68™, commercially available from BASF™; other surfactants can also be used. Other surfaces that can be coated include the inner surface of the needle body 32, the outer surface 154 of the needle body 32, the inner surface 152 of the dilator shaft 36, and the guidewire 44. These surfaces, including the outer-surface 160 of the dilator shaft 36 and the inner surface 158 of the sheath body 40, can be coated with a surfactant individually, or in combination. In the embodiments described above it may be preferable to coat both the outer-surface 160 of the dilator shaft 36 and the inner surface 158 of the sheath body 40 to promote or enhance progression of a body fluid through the channel 156. However, in some embodiments it may be preferable to only coat one of these two surfaces with a surfactant.

Use of a surfactant can accelerate and facilitate the progression of blood through the needle, dilator, or sheath. Accordingly, smaller needles, dilators, and sheaths can be used while still allowing blood to travel through said pieces with sufficient speed to indicate to an operator that the needle has entered the vessel or drainage site. Notably, in most embodiments a body fluid will pass through the needle, and thus in most embodiments it can be desirable to apply a surfactant to the interior surface of the needle.

Similarly, one or more of these components can be made of a hydrophilic material. A hydrophilic substance additionally can be applied to the outer surface of the sheath 26 to act as a lubricant to ease insertion of the sheath 26 into a patient. Other lubricants or lubricous coatings can be used on the exterior of the sheath 26 or at least the outer surface of the sheath can be formed of a lubricous material. Additionally, the sheath 26 can be coated or formed with agents (e.g., heparin), which elute from the sheath, to facilitate the clinical application of the access device 20. In one example, the outer surface of the sheath 26 can include a coating of silicone, such as Dow Corning 360 Medical Fluid, 12,5000 CST™, commercially available from Dow Corning. Similarly, the sheath can be coated with a surfactant in some embodiments.

FIG. 8H is a cross sectional view of the embodiment depicted in FIG. 8C along line 8H-8H. In this region of the illustrated access device 20, the sheath body 40 is coaxially positioned to minimize the annular space 157 between the sheath body 40 and the dilator shaft 36 while still allowing relative movement of the sheath body 40 and the dilator shaft 36. The inner surface 158 of the sheath body 40 need not, though it can, lie directly against the outer-surface 160 of the dilator shaft 36. The annular interface 157 between the outer-surface 160 of the dilator shaft 36 and the inner surface 158 of the sheath body 40 may be reduced in this region to inhibit the distal flow of blood or its constituents (or other bodily fluids) from the opening 74 in the dilator shaft 36.

Figure 8J:
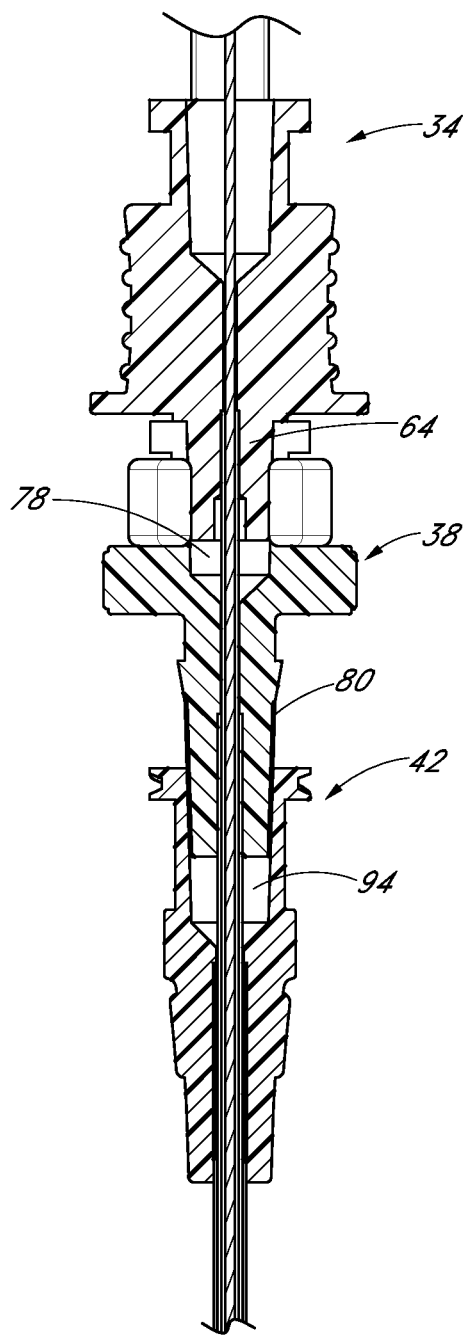
FIG. 8J is a cross-sectional view of the embodiment depicted in FIG. 8I.
Figure 8I:
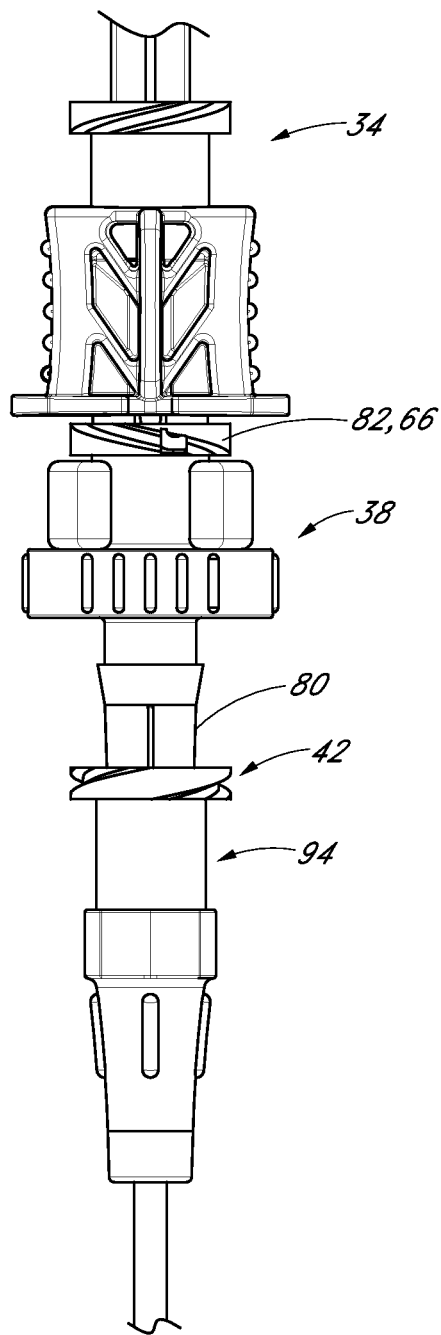
FIG. 8I is an enlarged view of the embodiment depicted in FIG. 8A focusing on the area where the needle hub is locked to the dilator hub when the needle hub is in the first position.

FIG. 8I is an enlarged plan view of the portion of the embodiment illustrated in FIG. 8A which is circled by line 8I-8I. FIG. 8J is a cross-sectional view of the embodiment depicted in FIG. 8I. FIGS. 8I and 8J illustrate the needle hub 34 locked to the dilator hub 38 when the needle hub is in the first position 121. The dilator shaft 36 may be coaxially mounted to the needle body 32 by slipping a hollow section 84 of the dilator shaft 36 over the needle body 32 and releasably securing the dilator hub 38 to the needle hub 34. The proximal end 86 of the dilator hub 38 is configured to mechanically fit and interlock with the needle hub 34.

The dilator shaft 36 may be releasably mounted to the needle body 32 so that the dilator shaft 36 can be mounted and released, or vice versa, from a coaxial position relative to the needle body 32. This locking mechanism can inhibit at least some unintentional rotational and axial movement between the needle 22 and the dilator 24 when the needle hub 34 is in the first position. As shown, the needle hub 34 may have a luer connection 64 that locks to the luer connection 78 of the dilator hub 38. Furthermore, the needle hub 34 may also have a latch element 66 that locks to the opening 82 in the dilator hub 38.

In addition, FIGS. 8I and 8J illustrate the dilator hub 38 engaged with the sheath hub 42 when the access device 20 is inserted into a vessel 148. Preferably, the proximal end 86 of the sheath hub 42 is configured to mechanically fit and releasably engaged with the dilator hub 38. As shown, the luer connection 80 in the dilator hub 38 can engage with the lock member 94 of the sheath hub. The resulting friction fit can inhibit at least some unintentional rotational and axial movement between the dilator 24 and the sheath 26 when the access device 20 is inserted into a vessel 148.

Figures 9A, 9B:
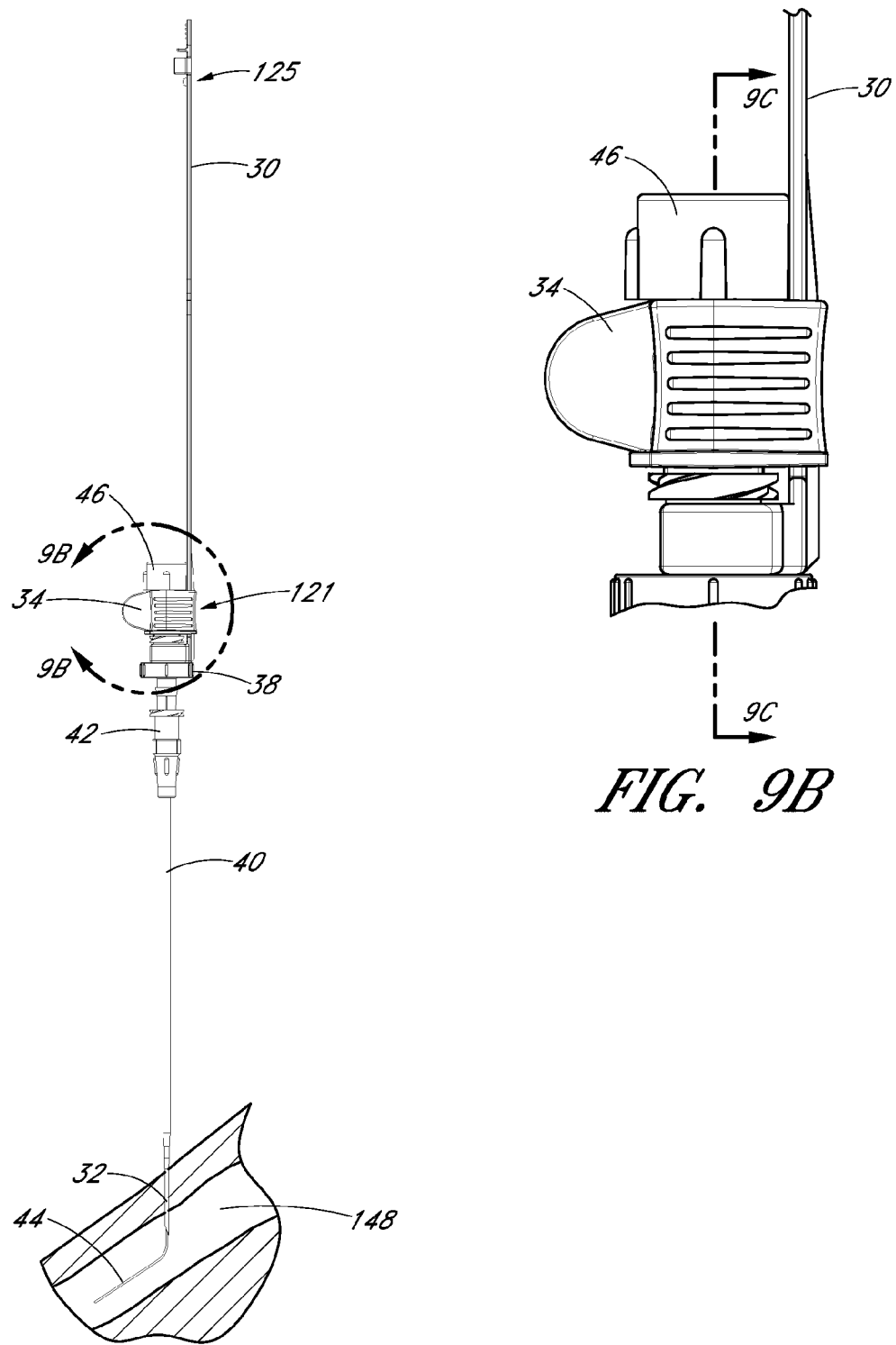
FIG. 9A is a side view of the embodiment depicted in FIG. 1A illustrating the guidewire advanced from the needle tip in a distal direction.
FIG. 9B is an enlarged view of the embodiment depicted in FIG. 9A focusing on the area where the guidewire hub is locked to the needle hub when the needle hub is in the first position.

FIG. 9A is a side view of the embodiment depicted in FIG. 1A that illustrates a further operational step of the access device 20. FIG. 9A depicts the guidewire 44 of the access device 20 advanced in a distal direction into a vessel 148. This can be achieved by advancing guidewire hub 46 from the third position 125 in a distal direction. The guidewire hub 46 is then locked to the needle hub 34 when the needle hub 34 is in the first position 121.

Figure 9C:
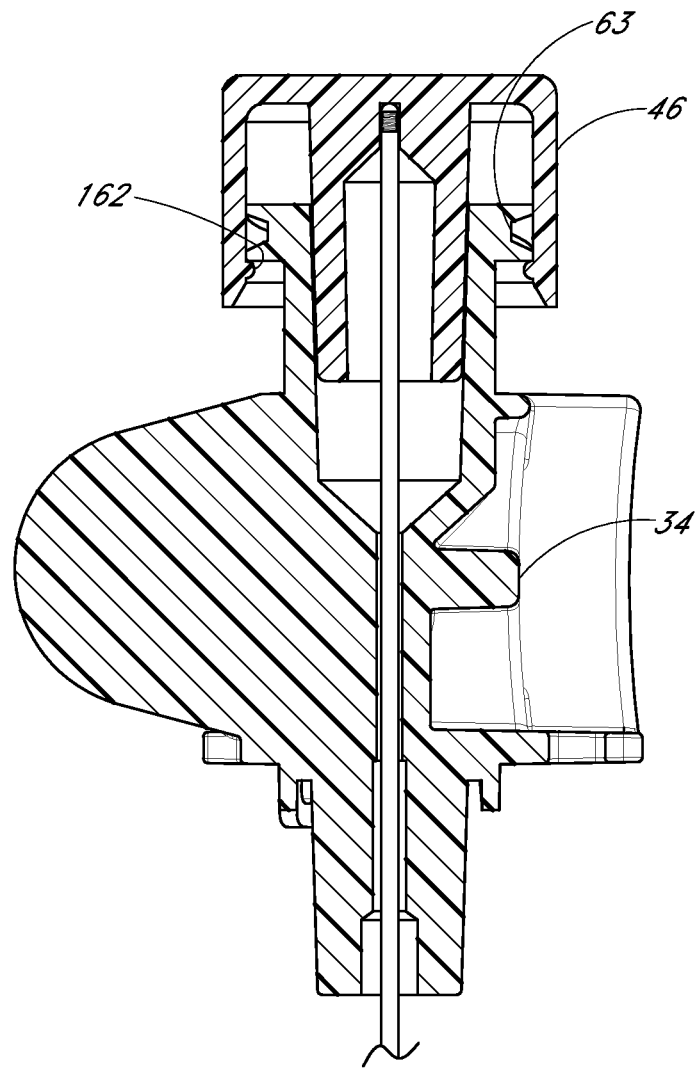
FIG. 9C is a cross-sectional view of the embodiment depicted in FIG. 9B.

FIG. 9B is an enlarged side view of the portion of the embodiment illustrated in FIG. 9A which is circled by line 9B-9B. FIG. 9C is a cross-sectional view of the embodiment depicted in FIG. 9B. FIG. 9C illustrates the locking mechanism between the guidewire hub 46 and the needle hub 34. Preferably, the guidewire hub 46 is configured to mechanically fit and releasably or irreversibly interlock with the needle hub 34. As shown, the guidewire hub 46 includes a nub 162 on the inner surface of the guidewire hub 46. The nub 162 of the guidewire hub can lock onto the needle hub 34 by advancing the guidewire hub 46 in a distal direction until the nub 162 is secured within the threaded groove on the lip of the needle hub 46. In other embodiments, the guidewire hub 46 can lock to the needle hub 34 via corresponding threaded elements.

Figures 10A, 10B:
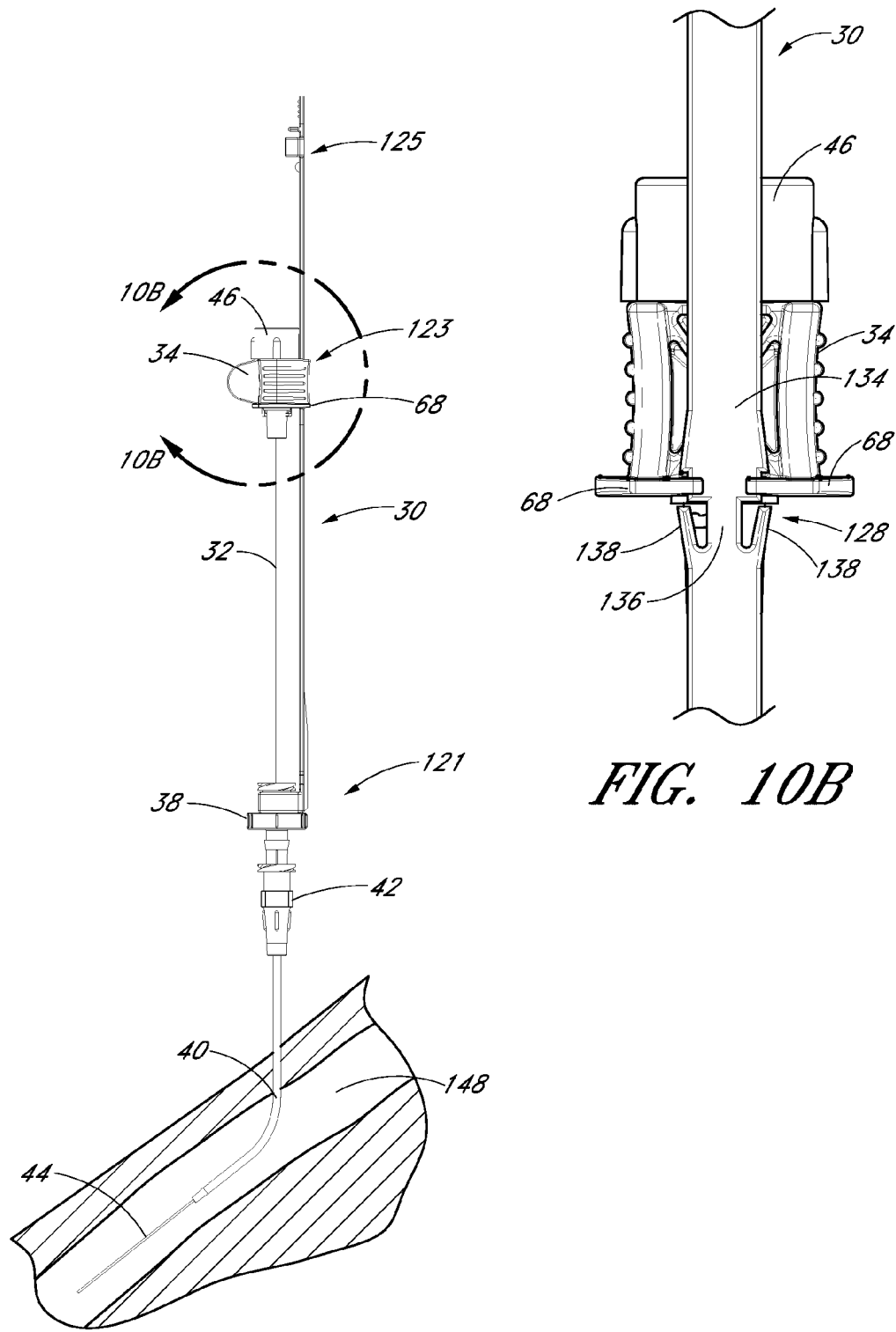
FIG. 10A is a side view of the embodiment depicted in FIG. 1A illustrating the dilator and sheath being advanced distally relative to the needle body from the position illustrated in FIG. 9A.
FIG. 10B is an enlarged rear view of the embodiment depicted in FIG. 10A focusing on the area where the needle hub is locked to the track when the needle hub is in the second position.

FIG. 10A is a side view of the embodiment depicted in FIG. 1A that illustrates another operational step of the access device 20. FIG. 10A depicts the dilator shaft 36 and the sheath body 40 advanced in a distal direction into a vessel 148. This can be achieved by releasing the dilator hub 38 from the needle hub 34 and advancing the dilator 24 and sheath 26 in a distal direction relative to the needle hub 34 along the guidewire and needle. FIG. 10A further illustrates the proximal movement of the needle 22 and guidewire section 28 relative to the dilator 24 and the sheath 26. The needle hub 34 will lock to the track 30 when the needle hub 36 reaches the second position 123.

FIG. 10B is an enlarged rear view of the portion of the embodiment illustrated in FIG. 10A which is circled by line 10B-10B. As depicted in FIG. 10B, the needle hub 34 locks onto the track 30 via the locking mechanism 128 in the second position 123. The needle hub tangs 68 slide in a proximal direction over the track fingers 138 and the tangs 68 can lock into place between the track fingers 138 and the track section of increasing width 134. This arrests and, more preferably, substantially irreversibly prevent axial movement of the needle body 32 at least in the distal direction when the needle hub 34 is in the second position 123. In the illustrated embodiment, the locking mechanism 128 irreversibly prevents the needle hub 34 from moving in either the proximal or distal directions once engaged. Furthermore, the distal tip 54 of the needle 22 is drawn into the dilator 24 to sheath the distal tip 54 when the needle hub 34 is in the second position 123. Thus, this locking mechanism 128 inhibits the bevel tip 54 disposed on the distal portion 50 of the needle body 32 from being advanced beyond the distal end of the dilator shaft 36 once the dilator shaft 36 has been advanced over the needle body 32 during use. The dilator shaft 36 thus sheaths the sharp bevel tip 54 of the needle body 32 to inhibit accidental needle sticks from occurring.

FIG. 11A is a side view of the embodiment depicted in FIG. 1A that illustrates the final operational step of the access device 20. FIG. 11A illustrates the removal of the guidewire 44 and the dilator shaft 36 from the vessel leaving the sheath body 40 properly inserted within the vessel 148. FIG. 11B is an enlarged plan view of the portion of the embodiment illustrated in FIG. 11A which is circled by line 11B-11B. As clearly shown in FIG. 11B, the distal end of the dilator shaft 36 and the guidewire 44 extend beyond the sharp bevel tip 54 of the needle body 32 to inhibit accidental needle sticks from occurring.

As noted above, having openings 56, 74 in the needle body 32 and dilator shaft 36 with different aspect ratios will increase the likelihood that the openings 56, 74 in the needle body 32 and dilator shaft 36 will be aligned so that blood flows substantially unobstructed through the needle side opening 56 and dilator side opening 74.

In the following embodiments, structure from one embodiment that is similar to structure from another embodiment share the same root reference number with each embodiment including a unique suffix letter (32, 32A, 32B, etc.). FIG. 12A is a plan view of another embodiment of the openings 56, 74 in the needle body 32 and dilator shaft 36 illustrated in FIGS. 8B and 8C. FIG. 12B is an enlarged cross-sectional view of the embodiment depicted in FIG. 12A along line 12B-12B. FIGS. 12A and 12B depict a needle body 32A with an oblong opening 56A and a dilator shaft 36A with a circular opening 74A. In other embodiments, the needle can have a circular opening and the dilator can have an oblong opening. These embodiments can increase the likelihood that the openings 56A, 74A will be at least substantially aligned so that blood flows through the needle side opening 56A and dilator side opening 74A.

FIG. 13A is a plan view of another embodiment of the openings 56, 74 in the needle body 32 and dilator shaft 36 illustrated in FIGS. 8B and 8C. FIG. 13B is an enlarged cross-sectional view of the embodiment depicted in FIG. 13A along line 13B-13B. FIGS. 13A and 13B depict a needle body 32B with a circular opening 56B and a dilator shaft 36B with a circular opening 74B that is larger than the circular opening 56B in the needle body 32B. In other embodiments, the opening in the dilator can be smaller than the opening in the needle. These embodiments can also increase the likelihood that the openings 56B, 74B will be at least substantially aligned so that blood flows through the needle side opening 56B and dilator side opening 74B.

As noted above, the dilator shaft 36 may have one or more channels 156 formed between ridges 76 to form a conduit or flow path between the sheath body 40 and the dilator shaft 36 to enable the physician or health care provider to view the blood after the bevel tip 54 of the needle body 32 has properly punctured a vessel or the channels may be formed without ridges but by extruding axial indentations of various possible configurations or by forming fully enclosed channels within the dilator shaft or body.

FIG. 14A is a plan view of another embodiment of the ridges 76 depicted in FIG. 8C. FIG. 14B is an enlarged cross-sectional view of another embodiment of the ridges 76 depicted in FIG. 8D. FIGS. 14A and 14B depict two ridges 76C on the inner surface 158C of the sheath body 40C that form at least one channel 156C between the sheath body 40C and the dilator shaft 36C.

FIG. 15A is a plan view of another embodiment of the ridges 76 depicted in FIG. 8C. FIG. 15B is an enlarged cross-sectional view of another embodiment of the ridges 76 depicted in FIG. 8D. FIGS. 15A and 15B depict two ridges 76D on the inner surface 158D of the sheath body 40D and two ridges 76E on the outer surface 160D of the dilator shaft 36D that combine to form a channel 156D between the sheath body 40D and the dilator shaft 36D. For example, if the desired channel thickness is about 0.001 inches, the two ridges 76D on the inner surface 158D of the sheath body 40D can each be about 0.0005 inches thick and the two ridges 76E on the outer surface 160D of the dilator shaft 36D can each be about 0.0005 inches thick.

FIG. 16A is a plan view of another embodiment of the ridges 76 depicted in FIG. 8C. FIG. 16B is an enlarged cross-sectional view of another embodiment of the ridges 76 depicted in FIG. 8D. FIGS. 16A and 16B depict many ridges on the outer surface 160E of the dilator shaft 36E. Between adjacent ridges are splines 76F. The splines 76F form a plurality of channels 156E between the sheath body 40E and the dilator shaft 36E. One or more of the channels 156E can have the same span angle $\Phi$ or different span angles $\Phi$. In the illustrated embodiment the channels 156E have span angles of 120 degrees and 23 degrees. In another embodiment, a single ridge 76 can spiral around the exterior of the dilator along its length.

Figure 17:
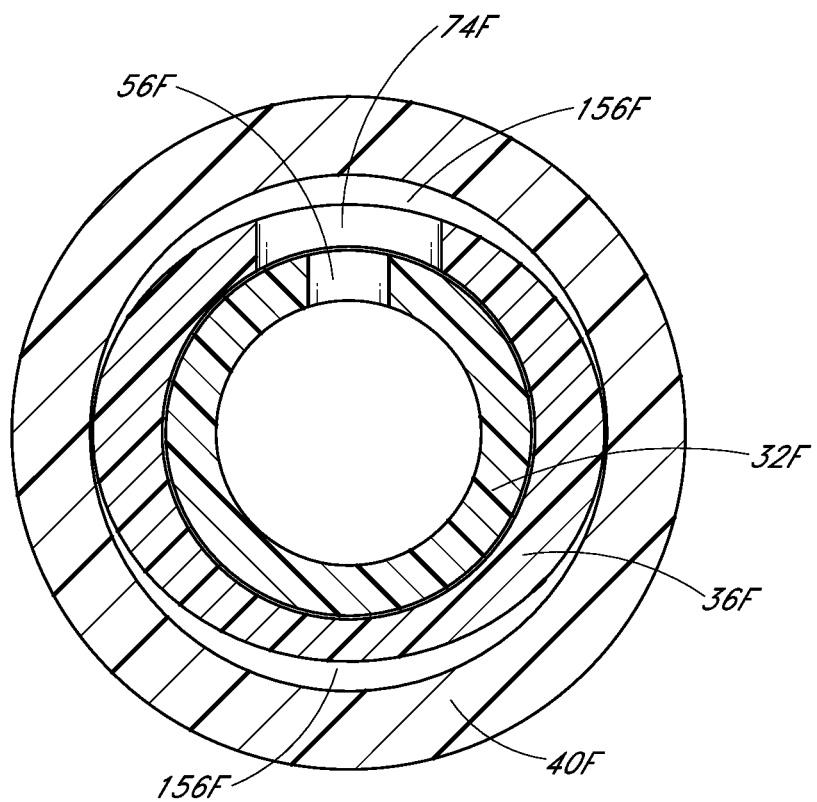
FIG. 17 is an enlarged cross-sectional view through another embodiment of the access device and shows the channel formed between a sheath and a dilator that have dissimilar shapes.

FIG. 17 is an enlarged cross-sectional view through another embodiment of the access device and shows the channel 156F formed between a medical article or sheath body 40F and a dilator shaft 36F that have dissimilar shapes. In the illustrated embodiment, the outer surface of the dilator shaft 36F has an oval shape while the inner surface of the sheath body 40F has a round shape. The oval dilator shaft 36F and the adjacent round sheath body 40F form one or more channels or gaps 156F between the sheath body 40F and the dilator shaft 36F. Of course the shapes of the sheath body 40F and dilator shaft 36F are not limited to round and oval and may include any other combination of dissimilar shapes in adjacent regions of the sheath body 40F and dilator shaft 36F. In some modes, the outer surface of the dilator shaft 36F is oblong and the inner surface of the sheath body or medical article 40F is round. In some modes, the outer surface of the dilator shaft 36F is round and the inner surface of the medical article 40F is square. The gap or channel 156F can follow a longitudinal axis, a spiral path along the longitudinal axis, a linear path along the longitudinal axis or other path along the access device. In some modes, the linear path is parallel to the longitudinal axis. The gap or channel 156F thickness can vary along at least a portion of a length of the gap or channel 156F.

In another mode, the access device includes a blood flash-back space defined between the shaft of the needle and the shaft of the dilator. In this mode, the flash-back space preferably vents to the atmosphere and more preferably vents independent of the sheath. In particular, as described below, a vent passage is formed through the dilator, through the needle, or between the dilator and the needle.

Figure 18D:
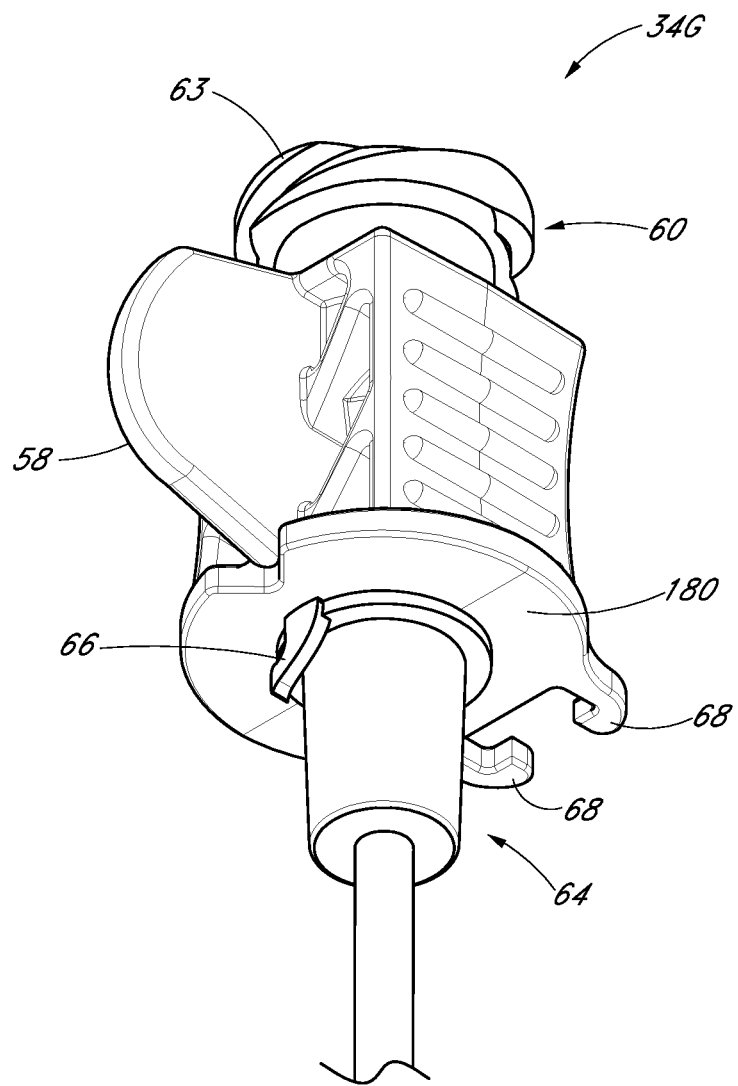
FIG. 18D is an enlarged perspective view of a needle hub configured to form part of the needle depicted in FIG. 18A.
Figure 18E:
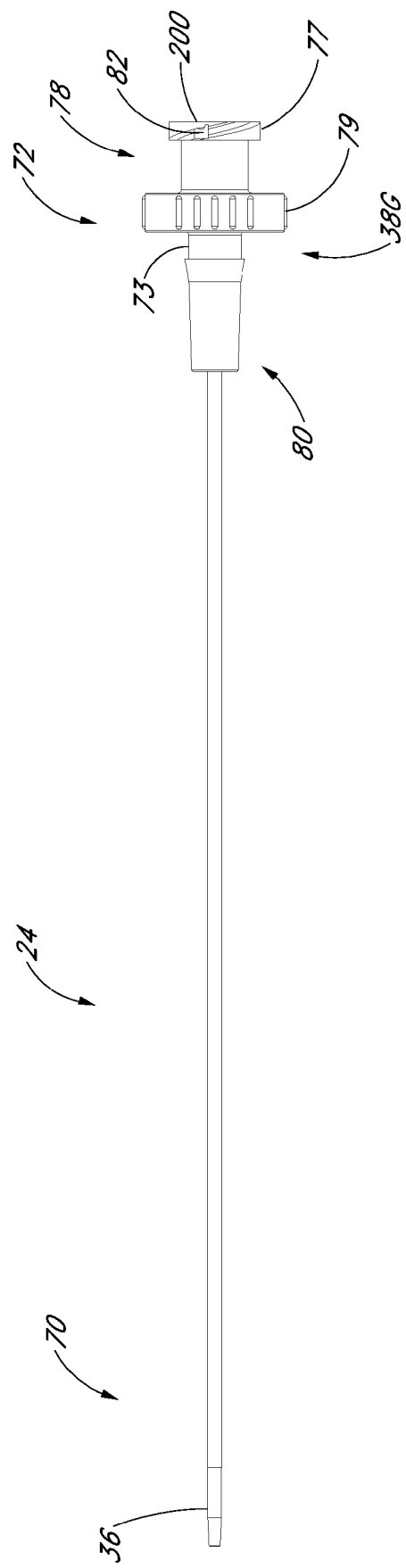
FIG. 18E is a plan view of the dilator of FIG. 18A.

FIGS. 18A-18E illustrate an embodiment of this mode of the access device, wherein a vent channel is formed between the needle and the dilator. As best seen in FIGS. 18A-18C, the needle body 32G includes one or more fenestrations 56 (e.g., like any of the fenestrations depicted in FIGS. 12A-16A), and one or more optional ridges 176 (e.g., two ridges 176 are shown in the illustrated embodiment). The ridges 176 define the sides of at least one channel 256 extending along a length of the needle body 32G. In some embodiments additional channels 256 can be formed with additional ridges. In other embodiments channels 256 can be formed with a protruding ridge, or without a protruding ridge such as with a depression(s) or with a concentric gap. Similarly, a channel 256 can be formed with protruding or non-protruding ridges on the inner surface of the dilator shaft 36G (instead of or in addition to features on the needle body 32G). Although the channel 256 is depicted as straight, it can also form other patterns such as a helix or another shape wrapping about the access device. Further, where multiple channels are present they can form intersecting helices, parallel helices, or other patterns. In other embodiments, a distance between the needle body 32G and a dilator shaft 36G (e.g. where the inner diameter of the dilator shaft exceeds the outer diameter of the needle body) can generally define a space, or a generally annular space, similar to the space created by the channels 256.

As best shown in FIG. 18D, the needle hub 34G can include one or more venting grooves 175. As depicted, the venting grooves 175 are on the luer connection 64, but in other embodiments they can be located on the needle body 32G, on the dilator shaft 36G, pass through the needle hub 34G, pass through a dilator hub 38G, or take some other path. The venting grooves 175 can provide communication between the channels 256 (or similar spaces) and the ambient atmosphere. The luer connection 64 can be configured to cooperate with the dilator hub 38G to form a substantially liquid tight seal, such that a substance can only escape through the venting grooves 175. In embodiments where the venting grooves 175 do not extend radially, a generally radially extending side 180 of the needle hub 34G can be configured to rest far enough apart from a corresponding face 200 of the dilator hub 38G to allow air to pass between them, from the venting grooves 175.

In some embodiments, the venting grooves 175 can form a passage sufficiently small in cross-sectional area to allow the escape of gases (e.g., air) to the ambient atmosphere while hindering the escape to the ambient atmosphere of body liquids (e.g., red blood cells) with high molecular sizes, viscosities, or surface tensions. Further, in some embodiments multiple such passages can be provided, allowing adequate air ventilation despite small cross-sectional passages.

In other embodiments, the small cross-sectional area of the passage can be provided between two opposing surfaces of the dilator hub 38G and the needle hub 34G. For example, at least a portion of the venting groove 175 on the needle hub 34G can be configured to receive a generally correspondingly shaped venting surface on the dilator hub 38G without entirely blocking the venting groove. The resulting passage between the surfaces of the needle hub 34G and the dilator hub 38G thus define at least a region of relatively small cross-sectional area to permit air flow but restrict the flow of bodily fluids.

While the venting structure is depicted as grooves 175 in the illustrated embodiment, other structures can perform similar functions. For example, a single reduced space location between the needle body 32G and the dilator body 34G can permit the escape of air while inhibiting the flow of blood proximally beyond the reduced space location. Similarly, a labyrinth passage can be disposed between the ambient atmosphere and the flash-back space (the space between the needle and dilator).

In other embodiments, one or more of the venting grooves 175 can be filled at least in part by a porous material that permits gases to flow through the material but inhibits the passage of a body fluid (e.g., blood). Such material can be integrally formed into the needle hub 34G or dilator hub 38G such that the material and the hubs are unitary. The material can then comprise any portion of the length of the venting grooves 175. In other embodiments the material can be placed into the venting grooves 175 or a receptacle in communication with the groove(s). When the material is placed into the groove 175, the groove can include a receiving portion such as a groove notch 185 configured to receive the porous material. One or more of the vent passages in other embodiments can be entirely formed by such porous material. Suitable porous materials include, but are not limited to a porous polymer such as HDPE, UHMWPE, PP, PTFE, PVDF, EVA, PE, Nylon, and PU, of pore size approximately 2.5 microns. In further embodiments, a combination of pore volume and pore size can be chosen to allow passage of gases (such as air) but inhibit the passage of body fluids (such as blood).

In further embodiments, the venting passages can be tubes defined solely by either the needle hub 34G or the dilator hub 38G. For example, the channel 256 can lead to an opening in the needle hub 34G. This opening can include any of the characteristics discussed above to control the passage of gases and fluids. The opening can thus allow the escape of gases (e.g. air) through the needle hub 34G to the ambient atmosphere while inhibiting the passage of body fluids (e.g. blood). In other embodiments, a similar venting passage can be a tube defined solely by the dilator hub 38G. It will be clear from the disclosure herein that a variety of passages (e.g. venting grooves 175, tubes, porous material, etc.) can be used to allow the escape of gases (e.g. air) to the ambient atmosphere while inhibiting the escape of body fluids (e.g. blood).

In another embodiment, the venting passages can be within the dilator shaft 36G and the sheath body 40. For example, a venting hole or a patch of venting material can be provided in each of the dilator shaft 36G and the sheath body 40. In some embodiments these venting structures can overlap, allowing gases to pass directly from one to the other. In other embodiments, these venting structures can be positioned some distance away from each other, in which case a channel or groove similar to those in FIG. 18D can be provided between the dilator shaft 36G and the sheath body 40 to bring the venting structures into communication. These venting structures can be provided proximal from the fenestration 56 in the needle body 32G.

As shown, the dilator shaft 36G in this embodiment can have no fenestration and can be generally continuous. The dilator shaft 36G can thus radially close the channel 256 (or similar space). In similar embodiments the same functionality can be accomplished with ridges in the dilator shaft 36G cooperating with an otherwise generally continuous needle 32G including a fenestration 56. The dilator shaft 36G can be formed of a translucent material in the entirety, or alternatively be translucent in at least the region adjacent the channel 256. The sheath body 40 can be similarly formed of a translucent material. In other embodiments, the material can be transparent instead of only translucent. In further embodiments, the material can be only partially translucent both spatially and temporally. Spatially, the material of the dilator shaft 36G and/or the sheath body 40 can be translucent near the channel 256, allowing visual confirmation of e.g. blood flash-back. Temporally, the visual characteristics of the material can change upon entry of a body fluid (e.g. due to temperature change or molecular interaction). The material can thus become translucent upon entry of a body fluid, or in other embodiments change color or provide some other visual indication.

Further, the access device depicted in FIGS. 18A-18E can include surfactants and/or lubricious coatings, as described above. For example, in some embodiments a surfactant can be applied to the interior of the dilator shaft 36G, the exterior of the needle 32G, and/or the interior of the needle. The surfactant can be applied to any combination of these surfaces, depending on the desired effect. For example, the surfactant can be applied solely to the outer surface of the needle, solely to the inner surface of the dilator, or solely to the inner surface of the needle. As another example, a surfactant can be applied to combinations of these surfaces, such as to both the inner surface of the dilator and the outer surface of the needle. The surfactant can ease the passage of a body fluid through spaces within the access device, accelerating flashback. As another example, in some embodiments a similar channel can be provided between a dilator shaft and a sheath body, and the surfactant can be supplied on the inner surface of the sheath and the outer surface of the dilator. Even further, in some embodiments channels can be provided both between the dilator and needle and the dilator and sheath, with the channels being in communication via a fenestration in the dilator, as described herein. Further, as described above, the outer surface of the sheath can be coated with a surfactant, lubricious material, or the like.

In other embodiments, the channel 156 can be formed by having one complete ridge on the inner surface of the sheath and one complete ridge on the outer surface of the dilator. In other embodiments, the inner surface of the sheath can have two ridges that run 50% of the length of the channel 156 and the outer surface of the dilator can have two ridges that run the remaining 50% of the channel 156.

Figure 19A:
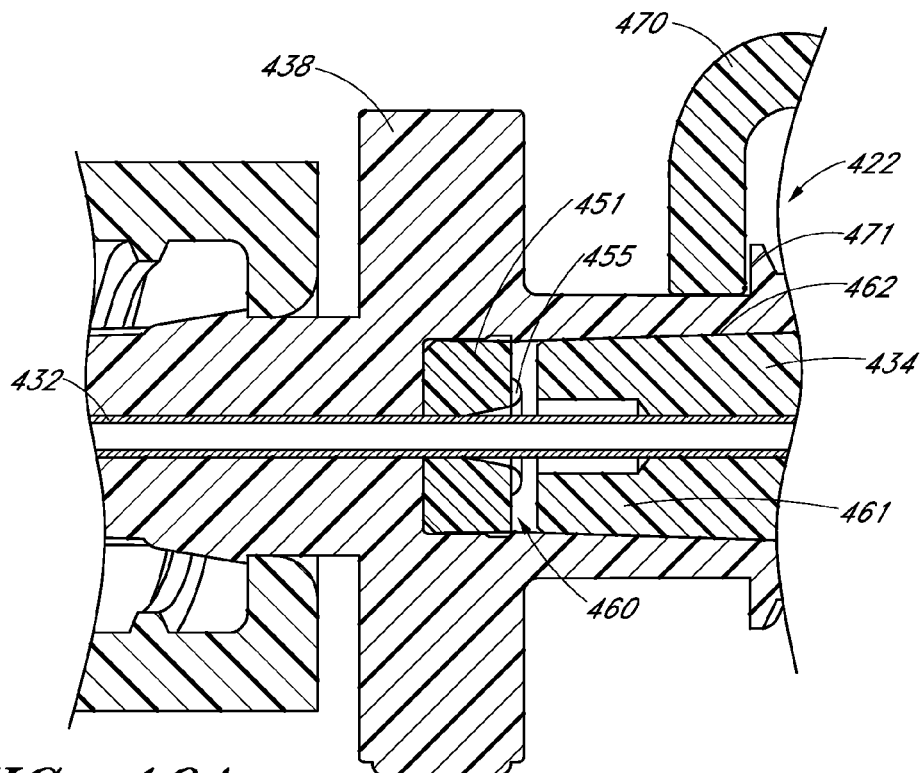
FIG. 19A is an enlargerd cross-sectional view of another embodiment of an access device showing portions of a needle hub, a dilator hub, and an insert.
Figure 19B:
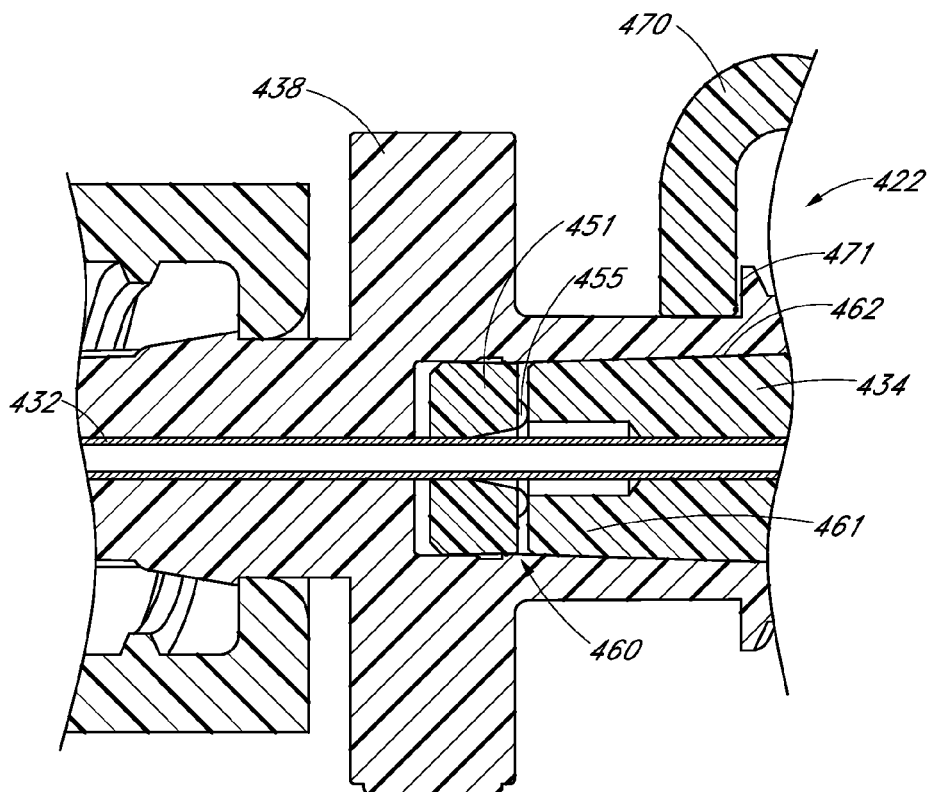
FIG. 19B is an enlarged cross-section view of the access device of FIG. 19A, wherein an insert is not fully inserted.

In even further embodiments, the venting can be provided at least partially through an insert 451 between a dilator hub 438 and needle hub 434, as best shown in FIGS. 19A, 19B. In some embodiments, an additional piece such as the insert 451 can facilitate the provision of certain desirable dimensions, materials, and other design features that might not be otherwise possible or economical. For example, in the embodiment discussed above regarding FIGS. 18A-18E, it may be desirable for a middle portion of the dilator shaft 436 to have an inner diameter substantially larger than the outer diameter of the needle body 432 near a needle fenestration (such as those described in relation to other embodiments). This difference in diameters can create a space that allows a body fluid to flow between the two (such as in the channel 256) from the fenestration. However, as will be discussed further below, in some embodiments it may also be desirable to provide the dilator shaft 436 with a smaller inner diameter near the dilator's distal tip. In further embodiments (such as those described above) it may be desirable to provide a proximal portion of the dilator 424 that also has a smaller diameter to hinder the flow of a body fluid such as blood proximally while still allowing the venting of gases. As discussed above, this venting can facilitate the drawing of a body fluid into the space, cavity, or channel. However, it may be difficult to manufacture a dilator 424 with small inner diameters at its proximal and distal ends, and a large inner diameter in a middle portion.

Figure 19C:
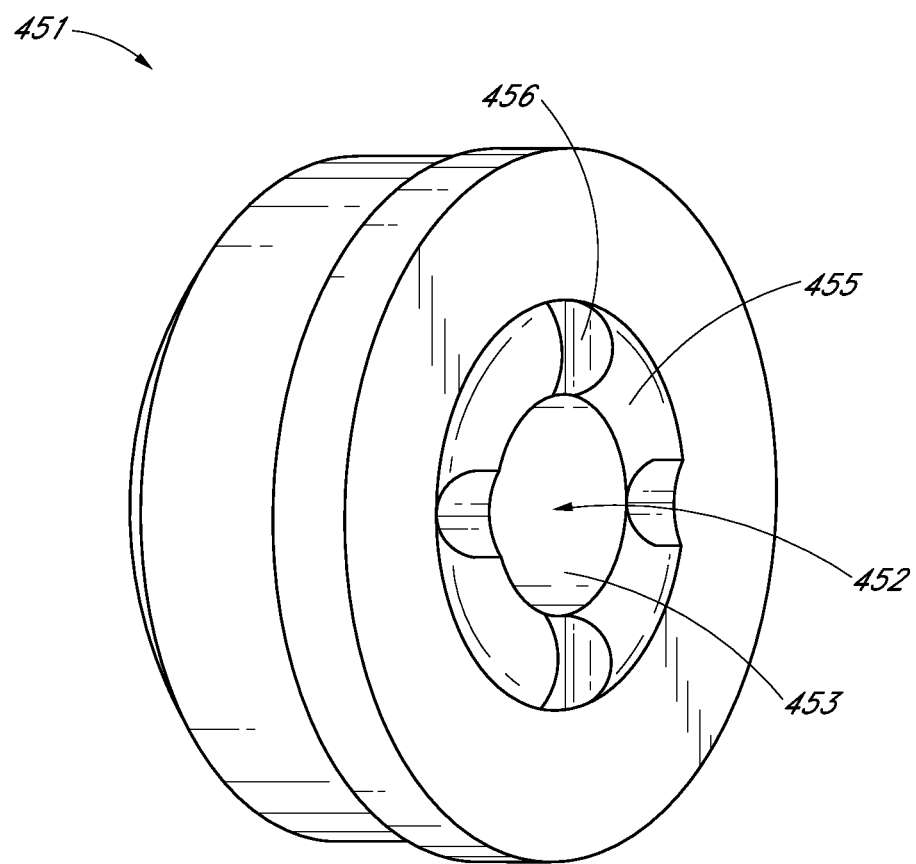
FIG. 19C is an enlarged view of an insert of the access device of FIG. 19A.
Figure 22A:
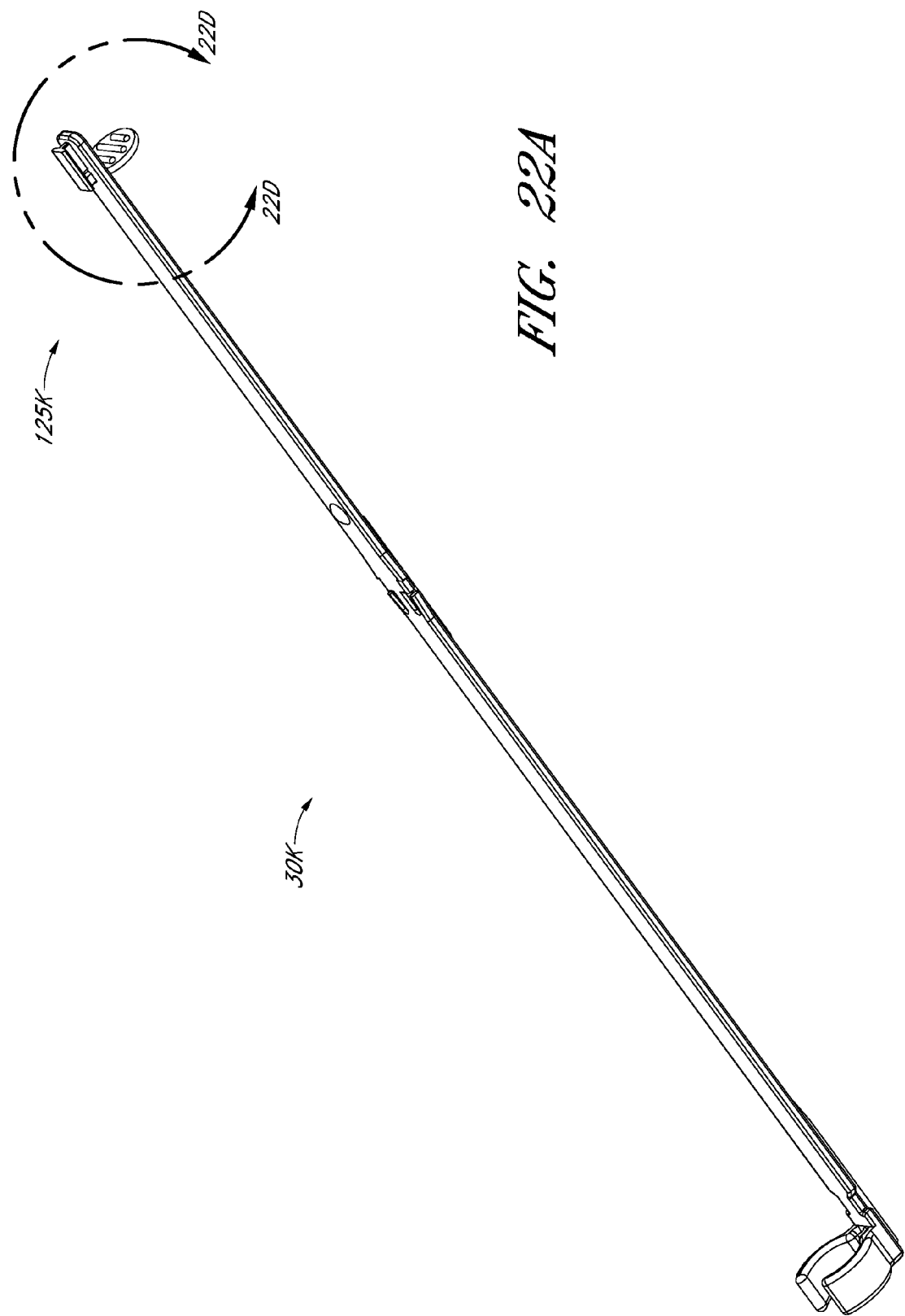
FIG. 22A is a perspective view of another embodiment of a track.
Figure 22B:
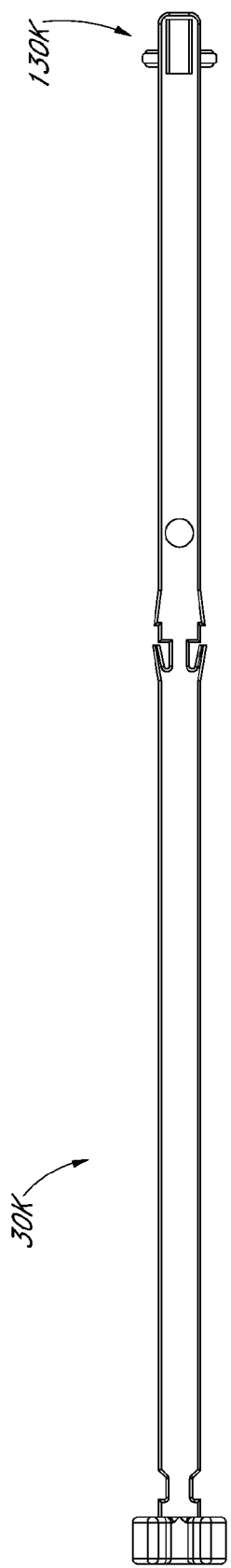
FIG. 22B is a plan view of the track of FIG. 22A.
Figure 22C:
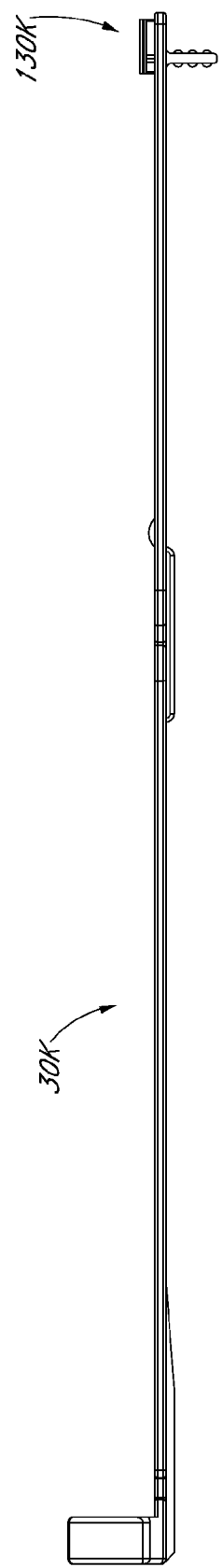
FIG. 22C is a side view of the track of FIG. 22A
Figure 22D:
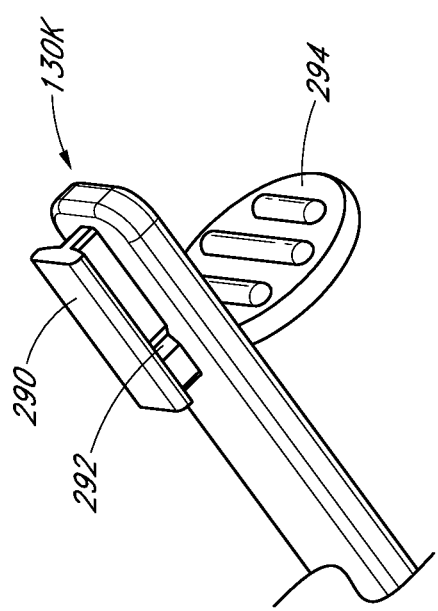
FIG. 22D is an enlarged view of a section of the track of FIG. 22A taken at 22D-22D.

The embodiment depicted in FIGS. 19A-19C provides venting with the assistance of an insert 451. The insert 451 can be disposed within a proximal opening 460 of the dilator hub 438. The proximal opening 460 can be configured to also receive a distally protruding portion 461 of the needle hub 434, as described in similar embodiments above (e.g., the portions forming a luer fitting between the needle and dilator hubs). In some embodiments the insert 451 can be press-fit into the dilator hub 434, while in other embodiments it can be loosely slid onto the needle body 432 (prior to combination with the dilator 424).

As best depicted in FIG. 19C, the insert 451 defines a through-hole 452 that can slidingly receive the needle 422 (or another needle described herein), e.g. along the needle body 432. Further, as depicted, the insert 451 can be substantially circular, or donut-shaped, allowing flexibility in its rotational position within the dilator hub 438. However, in other embodiments the insert 451 can be rotationally fixed within the dilator hub 438, i.e., with a non-circular insert and a corresponding non-circular receiving portion in the dilator hub 438.

Even further, the insert 451 can have particular dimensions to facilitate the release of gases while hindering the release of body fluids. For example, the diameter of the insert's through-hole 452 can be only slightly greater than the outer diameter of the needle body 432, creating a space that allows the release of gases but hinders the release of a body fluid. As best shown in FIGS. 19A, 19B, the gases can then enter a space between the needle hub 434 and the insert 451 within the receiving portion of the dilator hub 438. From this space, the gases can then proceed to the ambient atmosphere in a passage 462 defined between the needle hub 434 and the dilator hub 438. Notably, although in some embodiments the needle hub 434 and the dilator hub 438 can connect via a luer connection that may prevent the passage of gases, additional mechanisms can also attach the two hubs. For example, in the depicted embodiment the needle hub 434 can include a hook portion 470 that can releasably hook to a ledge portion 471 of the dilator. In other embodiments the latch element 66 and the opening 82 (described in previous embodiments) can also attach the two hubs. Thus, components that might otherwise form a luer connection between the two hubs can also be sufficiently separated to allow the escape of gases without compromising a connection between the hubs.

Further, the outer edge of the insert 451 can be shaped to substantially match the receiving portion of the receiving portion of the dilator hub 438 to form a seal between the two that at least hinders the escape of a body fluid therethrough. In some embodiments, a taper within the dilator hub 438 (also used for a luer connection with a needle, as discussed above) can facilitate a seal between the insert 451 and the dilator hub. In some embodiments, the seal between the outer edge of the insert 451 and the receiving portion 460 of the dilator hub 438 can also be impermeable to gases, forcing their passage through the through-hole 452, as described above.

During assembly, when the insert 451 is inserted into the dilator hub 438, the insert can sometimes enter slightly off-angle from the receiving portion and thus be stuck slightly ajar. Due to the size of the pieces and the depth of the receiving portion 460, it may be difficult to detect when the insert 451 is ajar. Thus, the insert 451 can be configured to provide tolerances for such off-angle insertion. For example, as depicted the through-hole 452 can include a proximally-tapered portion 453. The proximally tapered portion 453 can help preserve a venting space between the needle body 432 and the insert 451 through which gases can escape but the escape of a body fluid can be hindered.

The insert 451 can also include a proximally projecting portion depicted as a ridge 455 along its proximal face, which can be of particular relevance as shown in FIG. 19B. If the insert 451 is ajar, it may not completely enter the dilator hub 438, as depicted in FIG. 19B. The insert 451 can then come into contact with the needle hub 434. Such contact between the needle hub 434 and the insert 451 could then potentially form a seal, preventing the escape of gases through the insert's through-hole 452. Thus, in some embodiments, the insert can also include a ridge 455 with grooves 456. The needle hub 434 can contact the ridge 455 before contacting the rest of the proximal end of the insert 451, preserving a space therebetween. Further, the ridge 455 can include one or more grooves 456, providing an opening in the ridge 455 for gases to pass through, to the passage 462 between the hubs 434, 438. In the depicted embodiment, more than one groove can be provided to advantageously allow gases to pass through in multiple directions. Thus, if sealing contact between the insert 451 and the needle hub 434 is made on one side, gases can still escape on the other side.

In other embodiments, the proximally projecting portion on the insert 451 can take other forms. For example, in some embodiments the insert 451 can have one or more distinct projections to maintain separation from the needle hub 434. In further embodiments, the insert 451 can include one or more grooves that allow the escape of gases despite contact with the needle hub 434. Even further, in some embodiments similar structures can be provided on the needle hub instead of or in addition to the structures on the insert.

FIGS. 20A-20E depict another embodiment of a dilator 24H that includes additional elements to enhance the fluid flash-back feature of the access device 20. One additional element involves at least one wiper or seal that interacts with a needle (e.g., the needle 22 described in connection with the embodiment illustrated in FIGS. 1-7 above) about which the dilator 24H is coaxially disposed to inhibit fluid uptake thorough a space occurring between the needle exterior (e.g., needle exterior surface 154 of FIG. 8D) and the dilator interior (e.g., dilator interior surface 152 of FIG. 8D). The seal feature can be incorporated into any of the previously described embodiments of the access device 20, along with or separate from the other elements depicted in FIGS. 19A-19C. For example, the seal feature can have a smaller inner diameter and be on a dilator body associated with the dilator hub 438 depicted in FIGS. 19A-19C. While the illustrated embodiment describes this additional element in connection with a single seal, the dilator can include multiple seals located along the length of the dilator. Such seals can be located in series to the proximal side of the dilator fenestration and/or the needle fenestration. Additional seals can be located on the distal side of such fenestration as well in some embodiments; however, in the illustrated embodiment, the seal is depicted to the proximal side of both the dilator and needle fenestrations.

With reference to FIGS. 20B and 20C, the dilator 24H includes a sealing portion 250 that lies slightly proximal of a fenestration 74H on the dilator 24H. The sealing portion 250 is depicted as an inward protrusion that creates a narrowed region in the interior of the dilator 24H. At this sealing portion 250, the dilator 24H can form a seal with a needle (not shown) to separate the space between the dilator 24H and the needle into proximal and distal sections each lying to one side of the seal. One potential result is that, in embodiments where a fluid is intended to advance from the needle bore to a space between the dilator 24H and a sheath (e.g., the sheath 26 described in connection with the embodiment illustrated in FIGS. 1-7 above), fluid leakage into the proximal space between the dilator 24H and the needle is reduced, as the body fluid is inhibited from passing proximally beyond the sealing portion 250. Further, in some embodiments the sealing portion 250 can serve as a wiper, removing fluid (e.g., blood) from the surface of the distal portion of a needle as it is retracted into the dilator 24H.

The sealing portion 250 can take a variety of cross-sectional shapes, including triangular (an example of which is illustrated in FIG. 20C), rounded or rectangular. In the illustrated embodiment depicted in FIG. 20C, the sealing portion 250 has a generally triangular cross-sectional shape formed in part by a tapering surface 252 that slopes inward preferably in a proximal direction. The tapering surface 252 intersects with a ledge 251 of the sealing portion 250. The ledge 251 lies generally perpendicular to a longitudinal axis of the dilator 24H; however, in other embodiments, the ledge 251 can lie at various angles relative to the longitudinal axis so that an angle formed between the tapering surface 252 and the ledge 251 can be acute, right or obtuse. Advantageously, the tapering surface 252 on the sealing portion 250 can assist movement of the needle through the dilator 24H in a proximal direction. The ledge 251 allows the sealing portion 250 to deflect proximally as a needle is passing through. The dimension of the inward projection of the sealing portion 250 preferably is not significantly less than, and is more preferably greater than half of the difference in diameters between the exterior of the needle and the interior of the dilator at the point of the fenestrations.

As further depicted in FIG. 20B, in some embodiments the dilator 24H can include an expanded portion 260, formed with a taper 262 proximal of the sealing portion 250. The expanded portion 260 can reduce contact and friction between the dilator 24H and a needle (or other article for that matter) passing through the dilator 24H. When the sealing portion 250 inhibits proximal passage of a body fluid, the proximal space within the expanded portion 260 will receive little if not none of the body fluid across the seal formed by sealing portion 250. Additionally, in some embodiments a needle or other article passing through the dilator 24H can include a stop portion extending axially outward to engage the taper and inhibit further advancement of the article. Thus, the expanded portion 260 and its coinciding taper can define a limit on axial movement between the dilator 24H and a corresponding needle or other article.

When the needle is withdrawn into the dilator and locked therein, the distal end of the needle can lie to the proximal side of the sealing portion 250 in some embodiments, and can lie to the distal side of the sealing portion 250 in other embodiments. In either position, the absence or the reduction of fluid on proximal side of the seal lessens the amount of body fluid flowing through the dilator hub once the dilator has been withdrawn from the patient's body.

The sealing portion 250 can be formed on the dilator in any of a wide variety of ways readily known to those skilled in the art. For example, in some embodiments, the sealing portion 250 can be formed during a dilator tipping process after the dilator has been extruded. An internal mandrel can be cut with an annular groove that has the inverse image of the sealing portion 250. The mandrel is then placed within dilator. As the material of the dilator's distal end is heated during the tipping process and then pressed into the desired exterior shape, the material will also be forced into the annular groove on the mandrel to form the sealing portion 250. After sufficient cooling, the dilator can be withdrawn.

In other embodiments, a sealing portion can take a different form. For example, a needle can have an expanded exterior portion, forming an enlarged external diameter on the proximal side of its fenestration, similar to the enlarged internal diameter of the expanded portion 260 of the embodiment depicted in FIGS. 20A-20C. As such, the needle can have a smaller external diameter at a distal portion and a larger external diameter at a distal portion. The enlarged diameter portion can engage or abut against the internal surface of the dilator (e.g., against taper 262) to form a sealing portion similar to that described above. In some embodiments, the contact between the needle and dilator, forming a sealing portion, can be formed between matching tapers such as the taper 262 on the dilator 24H and a similar external taper on the needle. In other embodiments the contact between the needle and the dilator can be on other surfaces, such as surfaces generally parallel with the longitudinal axis of the needle and dilator.

As additionally indicated in FIGS. 20A, 20B, the dilator 24H can have an inner diameter $d1$ in a portion distal from the fenestration 74H. Further, as indicated in FIG. 21B (further discussed below), a needle (such as the needle 22J, or other needles such as the needle 22) can have an outer diameter $d2$. In some embodiments, $d1$ can be less than $d2$; this can provide a number of advantages. For example, the interference fit of the dilator 24H on the needle can put the dilator 24H under a radial or hoop load. This loading can increase the strength of the dilator 24H in an axial direction. The increased strength tends to reduce flaring, crimping or buckling of the material at the distal tip of the dilator when inserting the dilator through tissue (e.g., skin, muscle and/or vascular wall). For example, as the needle and dilator 24H pass through skin (without the use of a skin nick) the dilator can withstand axial forces that may otherwise deform the distal tip of the dilator. In some embodiments, this could cause a dilator to bunch, fold, or curl upon itself, increasing its cross-sectional area at said bunch or fold and inhibiting its functionality as a dilator. In other words, the deformed dilator becomes too difficult to insert into the patient. Providing the dilator with a smaller inner diameter d1 can increase the strength of the dilator, inhibiting the occurrence of such deformations.

In some embodiments, the inner diameter d1 of the dilator 24H can be smaller than the outer diameter d2 of a needle on which it mounts by approximately 15% or less. In other words, the outer diameter d2 of the needle can be approximately 15% larger than the inner diameter d1 of the dilator 24H. In more preferred embodiments, the inner diameter d1 of the dilator 24H is smaller than the outer diameter d2 by approximately 10% or less. In even more preferred embodiments, the inner diameter d1 is smaller than the outer diameter d2 by approximately 2% to 4% of the outer diameter d2. In particularly preferred embodiments, the inner diameter d1 of the dilator 24H can be approximately 97% of the outer diameter d2 of a needle on which it mounts.

Further, as depicted in FIG. 20B, the dilator tip can be beveled to provide a smoother dilation and to ensure further that the dilator tip does not deform upon entrance into the patient's body. As indicated, the tip can have a taper or bevel at an angle φ on each side (it is noted that the indicated angle φ's opposite angle is equal to φ, and thus they are treated as the same herein). The beveled tip can reduce axial forces on the dilator 24H upon passage through tissue (e.g., skin). In some embodiments, the angle φ can be approximately 30 degrees. In other embodiments, the angle φ can be between approximately 40 and 20 degrees. After this initial bevel, the dilator tip can taper at a shallower angle, as depicted in FIG. 20D. For example, in some embodiments the dilator can then taper at approximately 3 degrees, or alternatively at an angle less than approximately 3 degrees.

Additionally, as depicted in FIG. 20E, the dilator 24H can include a ridge or protrusion 264 through which the fenestration 74H passes. Thus, the ridge 264 can separate a sheath overlapping the dilator, facilitating any flow through the fenestrations 74H into a space between the dilator 24H and said sheath. Further, as depicted the ridge 264 can be generally thinner than the fenestration 74H. Thus, the ridge 264 can contact and separate the sheath while also leaving space for a fluid to flow around the ridge. As depicted, the ridge 264 can be generally oriented in an axial, proximal-distal direction. However, in other embodiments the ridge 264 can be oriented in a circumferential direction or otherwise.

FIGS. 21A and 21B depict a further embodiment of a needle 22J that can be used in a manner similar to that of other needles described herein such as the needle 22. The needle 22J can comprise an echogenic portion 270 at the distal tip. The echogenic portion can comprise a material that scatters waves used in imaging, thus facilitating visualization of the needle under ultrasound. Other imaging techniques can also be used, such as using a needle having a radio-opaque portion facilitating visualization under X-rays or fluoroscopy. The echogenicity can be increased by sandblasting the portion 270 to roughen the surface. The tip can be sharpened after sandblasting, allowing the tip of the needle to be echogenic. Echogenicity can also be increased by modifying the internal material of the needle itself, such as by adding granular impurities. However, in some instances modification of the internal material may unacceptably compromise the structural integrity of the needle. Advantageously, the echogenicity or similar imaging compatibility can allow an operator to easily view the needle tip inside the body using a scanning technique such as ultrasound.

In some embodiments a needle with an echogenic portion 270 can further lack fenestrations 56, 74, grooves 75, and/or surfactant. Further, in some embodiments with an echogenic portion 270, the access device can lack a flashback space or flash chamber.

In other embodiments, the needle 22J can have both an echogenic portion 270 and a fenestration 56 (in addition to other optional features described above). Further, in other embodiments, the needle 22J can include a contrast portion 280. The contrast portion 280 can have optical properties that improve the visibility of a fluid surrounding the contrast portion. For example, as described above, in some embodiments a body fluid can flow into a flashback space through the fenestration 56. The contrast portion 280 can then be positioned generally adjacent the flashback space and the contrast portion can have optical properties that contrast with the body fluid. Thus, the body fluid's entry into the flashback space can be more immediately apparent.

For example, in embodiments where the fluid entering the flashback space is a body fluid such as blood, the contrast portion 280 can have a color that contrasts with the color of blood, such as white, green, blue, etc. In further embodiments, other optical properties can be varied such as by choosing between a reflective or matte finish. In other embodiments, the contrast portion 280 can have be striped, checkered, dotted, or have some other pattern wherein the optical properties vary. For example, the contrast portion 280 can have black and white stripes oriented axially and/or circumferentially along the needle. Where a pattern with different optical properties is utilized, the contrast portion 280 can be more generic to different fluids that may be distinguishable from one region of the contrast portion 280 but not another region.

The varying optical properties can be applied in a variety of ways. For example, in some embodiments the contrast portion 280 can be painted to have a particular color, finish, pattern, etc. In other embodiments, portions of the needle can be polished or roughened to effect the reflective properties of the contrast portion 280. In even further embodiments, the contrast portion 280 can be formed from a different material, or have a different material applied to its surface, to yield different optical properties. Even further, in some embodiments the contrast portion 280 can be made echogenic, as in the echogenic portion 270 described above.

As depicted in FIG. 21A, the contrast portion 280 can be positioned just proximal from the fenestration 56 and extend a distance less than the entire distance of the needle 22J. This position can generally correspond to the beginning of a flashback space that may also be just proximal of the fenestration 56. However, in other embodiments the position of either or both the flashback space and the contrast portion 280 can vary. For example, in some embodiments the contrast portion 280 can span across the fenestration 56, or can be offset some distance therefrom. In further embodiments, the contrast portion 280 can extend to the needle hub or can span the entire needle body. As depicted, the contrast portion 280 can span circumferentially about the entire needle. However, in some embodiments the contrast portion 280 can be positioned only along an angularly reduced portion of the needle body, such as an angular portion having an angular span corresponding to the angular span of the fenestration 56.

In embodiments where the flashback space occurs between a dilator and a sheath (as described above), the dilator can have corresponding portions that are clear, translucent, transparent, or semi-opaque, such that the contrast portion 280 can be viewable from outside the access device. Then, as a fluid such as a body fluid enters the flashback space an observer can see both the contrast portion 280 and the body fluid as it enters the flashback space to occlude the contrast portion 280. The contrast in optical properties between the fluid and the contrast portion 280 can then facilitate the visual detection of the fluid's entry.

Additionally, in such embodiments where the flashback space occurs between the dilator and the sheath, the flashback can be enhanced or accelerated by sealing off or restricting air flow from the space between the needle body and the dilator body. In a preferred embodiment, fluid leakage (e.g., air egress) between a dilator and sheath can be reduced by placing a sealing piece such as a washer between the needle and dilator hubs. The washer reduces any fluid flow that might occur between a dilator and needle at their abutting hubs. Thus, a trapped air column can form between the dilator and needle that inhibits the flow of a body fluid (e.g., blood) into the space between the needle and dilator. The body fluid flow can thus be diverted, e.g., into a dilator fenestration 74H and into a space between a dilator and sheath. In some embodiments, the washer can be an elastic material, such as silicone. The washer can mount on the needle and have a planar or an o-ring-like shape.

This concept can also be applied to other embodiments. For example, in some embodiments a flashback space can be provided between a needle and a dilator. As between the dilator and the sheath, as discussed above, a channel can be formed between the needle and the dilator that can receive blood or other fluids through the needle fenestration 56. An example of such a flashback space is described in FIGS. 18B-18D and the accompanying text in Application No. PCT/US2009/037204, filed 13 Mar. 2009, and incorporated herein by reference in its entirety.

Thus, in some embodiments a preassembled access device can optionally be provided with a needle 22J that does not include any fenestrations and that can (but need not) be echogenic (depicted in FIGS. 21A, 21B), along with a guidewire, dilator, sheath, and associated hubs. Further, the preassembled access device can be inserted inside packaging, in the preassembled state. An operator can insert the access device into a patient and stop the advancement of the needle once the needle enters a targeted body space, as viewed from outside the body by ultrasound, X-ray, or some other imaging technique. The preloaded guidewire can then pass through the needle into the body space. The dilator can be advanced over the needle into the body space. The needle can be withdrawn the patient and further actions can be taken to insert the sheath over the dilator, as described above in relation to other embodiments.

In some embodiments, an access device can also include a modified track 30K and guidewire hub 46K, as depicted in FIGS. 22A-23B. As depicted, the track 30K and guidewire hub 46K can be substantially similar to the tracks and hubs discussed above, can be operated in a similar manner, and can be used similarly with other elements such as the needles, dilators, and sheaths described herein. For example, the track 30K can generally define a third position 125K with some similarity to the third position 125 described above. As depicted, the third position 125K can include a releasable coupling mechanism 130K that can engage with the guidewire hubs with corresponding parts, such as the guidewire hub 46K. The coupling mechanism 130K can include a coupling section 290 formed from a T-shaped projection extending from the track 30K. The T-shaped projection can additionally include two latch recesses, on each side of its base, generally toward a distal end of the coupling section 290.

A corresponding guidewire hub 46K can have corresponding structure with the coupling section 290 to releasably connect thereto. As depicted, the guidewire hub 46K can include a receiving section 296 that can be in the form of a recess. The recess can have a T-shaped cross-section at a proximal end to match the coupling section 290, as best depicted in FIG. 23A. Further within the recess of the receiving section 296, the receiving section can receive the base of the coupling section 290 along two tines that can terminate with latch projections 298. The latch projections 298 can interact with the latch recesses 292 on the coupling section 290 to form a reversible snap-fit between the track 30K and the guidewire hub 46K. In some embodiments, the tines can include bending portions 302 (formed e.g. from thinned material, to facilitate the snap-fit. Further, the receiving section 296 can include an end recess 300 in-line with the provided path provided for the coupling section 290 between the tines, such that when the latch recesses 292 and projections 298 interengage, the coupling section 290 can also enter the end recess 300. Thus, the connection between the track 30K and hub 46K can be further stabilized.

Additionally, in the depicted embodiment of the track 30K, the track can include a grip projection 294. The grip projection 294 can extend downward from the track 30K, opposite from the coupling section 290. As depicted, the grip projection 294 can be generally circular with gripping ridges, but other structures and shapes are possible. Advantageously, the grip projection 294 can allow an operator of the access device to hold the proximal end of the track 30K in a pistol-type grip. For example, a ring finger or middle finger can be positioned around the grip projection 294 to contact it on the distal side. The thumb of the same hand can then be placed on the proximal end of a guidewire hub 46K coupled in the third position 125K. The thumb can then easily apply pressure to move the hub 46K off of the coupling section 290 and out of the third position 125K. A similar grip projection can be applied to other tracks, such as the track 30 described above. Further, similar grip projections can be applied to other elements, such as a needle. Applying a grip projection to the needle can, for example, allow a needle to be easily gripped and moved along a track as described herein.

Figure 24A:
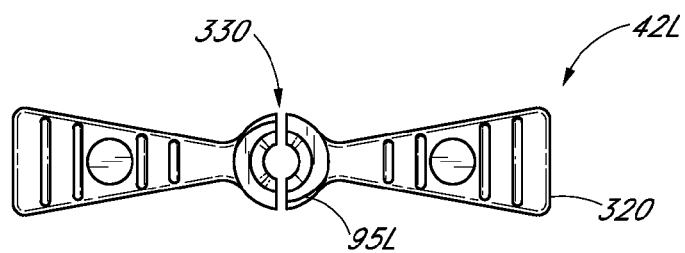
FIG. 24A is a proximal end view of another embodiment of a sheath.
Figure 24B:
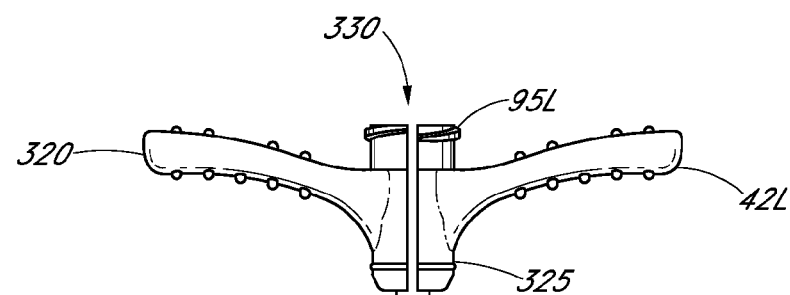
FIG. 24B is a plan view of the sheath of FIG. 24A.

In some further embodiments, a modified sheath 26L, with some similarities to the previous sheaths discussed, can be combined with the other element described. As depicted in FIGS. 24A and 24B, the sheath 26L can be a splittable sheath. As depicted, the sheath hub 42L can have two or more tabs 320 that can be gripped. The tabs 320 can then be pulled to split the splittable sheath 40L along a split line 330. As depicted, the split line 330 can extend through both the sheath hub 42L and the sheath body 40L. Thus, splitting the sheath 26L along the split line 330 can separate the sheath into two halves. The sheath 26L also can have a lip 95, allowing engagement with other elements described above, such as the dilator 24, in a manner similar to the sheath 26.

The sheath hub 42L can additionally include a ridge 325 toward a distal end of the hub. The ridge 325 can facilitate gripping of the hub 42L. Additionally, in some embodiments the ridge 325 can receive a tubular or cylindrical cover that can extend over the distal portions of the sheath, dilator, and needle to protect the tip, and press onto the ridge 325. Thus, the ridge 325 can hold the cover in place.

The embodiments herein described are comprised of conventional, biocompatible materials. For example, the needle preferably consists of ceramic, a rigid polymer, or a metal such as stainless steel, nitinol, or the like. The other elements can be formed of suitable polymeric materials, such as polycarbonate, nylon, polyethylene, high-density polyethylene, polypropylene, fluoropolymers and copolymers such as perfluoro (ethylene-propylene) copolymer, polyurethane polymers or co-polymers. For example, in some embodiments the dilator can be formed from nylon.

As noted above, the present access device can be used to place a catheter at other locations within a patient's body. Thus, for example, but without limitation, the access device can be used as or with a variety of catheters to drain fluids from abscesses, to drain air from a pneumotorax, and to access the peritoneal cavity. In such applications, body fluids flow into the viewing space to indicate when the needle has been properly placed.

Although this invention has been disclosed in the context of certain preferred embodiments and examples, it will be understood by those skilled in the art that the present invention extends beyond the specifically disclosed embodiments to other alternative embodiments and/or uses of the invention and obvious modifications and equivalents thereof. In addition, while a number of variations of the invention have been shown and described in detail, other modifications, which are within the scope of this invention, will be readily apparent to those of skill in the art based upon this disclosure. It is also contemplated that various combinations or sub-combinations of the specific features and aspects of the embodiments may be made and still fall within the scope of the invention. Accordingly, it should be understood that various features and aspects of the disclosed embodiments can be combined with or substituted for one another in order to form varying modes of the disclosed invention. For example, the general shape of the needle hub depicted in FIG. 18D differs in additional ways from the needle hub depicted in FIG. 2F. However, these general needle hub shapes can be interchanged between the described and depicted embodiments. Thus, it is intended that the scope of the present invention herein disclosed should not be limited by the particular disclosed embodiments described above, but should be determined only by a fair reading of the disclosure and the claims that follow.

What is claimed is:

1. An access device for placing a medical article within a body space, comprising:
a needle having an elongated needle body with a distal end and a hub from which the needle body extends, the elongated needle body comprising at least one side fenestration and an outer diameter;
a dilator slideably disposed on the needle body, comprising a dilator hub and an elongated dilator shaft that extends from the dilator hub, wherein the dilator shaft comprises at least one side fenestration in communication with the needle side fenestration, wherein the dilator shaft comprises an inner diameter that is less than the outer diameter of the needle, and wherein the dilator hub comprises a receiving portion;
a medical article comprising a tubular section and a hub, the tubular section being disposed on the dilator and defining a space between the medical article and the dilator in communication with the needle side fenestration through the dilator side fenestration, wherein at a least portion of the medical article is configured to allow visual determination of the presence of a body fluid within the space; and
an insert disposed within the dilator receiving portion, the insert comprising a through-hole configured to receive the needle body therethrough, the through-hole being slightly larger than the needle body so as to form a passage between the insert and the needle body that allows gases to pass through the passage and to the atmosphere but hinders the passage of a body fluid.

2. The access device of claim 1, wherein the inner diameter of the dilator is approximately 3% smaller than the outer diameter of the needle.

3. The access device of claim 1, wherein the dilator shaft comprises nylon.

4. The access device of claim 1, wherein the space comprises a surfactant or lubricious coating.

5. The access device of claim 1, wherein the fenestrations comprise different aspect ratios.

6. The access device of claim 1, wherein the fenestrations are aligned such that fluid can flow substantially unobstructed through both fenestrations.

7. The access device of claim 1, wherein at least one of the fenestrations forms an oblong opening.

8. The access device of claim 1, wherein both fenestrations form oblong openings that are generally perpendicular to each other when aligned.

9. The access device of claim 1, further comprising at least one elongated channel disposed between the needle and an exterior surface of the medical article that extends along at least a substantial portion of the length of the dilator shaft, the channel communicating with the fenestration in the needle and having a span angle of less than 360 degrees about a longitudinal axis of the dilator.

10. The access device of claim 1, wherein at least one of the dilator and medical article further comprise a vent in communication with the space that allows for the escape of air from the space and inhibits the escape of the bodily fluid from the space.

11. The access device of claim 1, wherein the needle and dilator are moveable relative to each other from a first position, wherein the distal end of the needle lies distal of the dilator, and a second position wherein the distal end of the needle lies within the dilator.

12. The access device of claim 11, further comprising a locking mechanism operating between the needle and the dilator to inhibit movement of the needle relative to the dilator when in the second position, the locking mechanism being configured to allow movement of the needle from the first position toward the second position without engagement by the locking mechanism so as to lessen resistance to the movement.

13. The access device of claim 12, wherein an elongated support suspends the first member of the locking mechanism at a location spaced from the dilator hub.

14. An access device for placing a medical article within a body space, comprising:
a needle having an elongated needle body with a distal end and a hub comprising a distal portion from which the needle body extends, the elongated needle body comprising at least one side fenestration;
a dilator comprising a dilator hub and an elongated dilator shaft that extends from the dilator hub, the dilator slideably disposed on the needle body and defining a space between the dilator shaft and the needle body in communication with the needle side fenestration, wherein the dilator hub comprises a receiving portion and at least a portion of the dilator shaft is configured to allow visual determination of the presence of a body fluid within the space; and
an insert disposed within the dilator receiving portion, the insert comprising a through-hole configured to receive the needle body therethrough, the through-hole being slightly larger than the needle body so as to form a passage between the insert and the needle body that allows gases to pass through the passage and to the atmosphere but hinders the passage of a body fluid.

15. The access device of claim 14, wherein the insert is shaped and sized to substantially match the inner surface of the receiving portion of the dilator to form a seal.

16. The access device of claim 14, wherein the insert comprises a proximal face that faces the needle hub and comprises one or more projections or grooves that can preserve a passage for gases between the insert and the needle hub.

17. The access device of claim 14, wherein the distal portion of the needle hub comprises a distal face that faces the insert and comprises one or more projections or grooves configured to preserve a passage for gases between the insert and the needle hub.

18. The access device of claim 14, further comprising a medical article comprising a tubular section and a hub, the tubular section being disposed on the dilator, wherein at least a portion of the medical article is configured to allow visual determination of the presence of a body fluid within the space.

19. The access device of claim 14, wherein a distal portion of the dilator shaft comprises an inner diameter that is less than the outer diameter of the needle.

20. The access device of claim 14, wherein the through-hole is disposed axially central within the insert.

21. The access device of claim 14, wherein the insert is disposed distal of the needle hub.

22. The access device of claim 14, wherein the insert comprises ridges or grooves that make the through-hole slightly larger than the needle body so as to form the passage.

23. An access device for placing a medical article within a body space, comprising:
a guidewire section comprising a guidewire and a guidewire hub;
a needle disposed on the guidewire and having an elongated needle body with a distal end and a hub from which the needle body extends;
a dilator disposed on the needle body, the needle and the dilator being moveable relative to each other from a first position, wherein the distal end of the needle lies distal of the dilator, and a second position wherein the distal end of the needle lies within the dilator, the dilator including a dilator hub and an elongated dilator shaft that extends from the dilator hub, and wherein the dilator hub comprises a receiving portion;
an insert disposed within the dilator receiving portion, the insert comprising a through-hole configured to receive the needle body therethrough, the through-hole being slightly larger than the needle body so as to form a passage between the insert and the needle body that allows gases to pass through the passage but hinders the passage of a body fluid;
a locking mechanism operating between the needle and the dilator, the locking mechanism comprising a portion spaced from the dilator that inhibits movement of the needle relative to the dilator when in the second position, the locking mechanism being configured to allow movement of the needle from the first position toward the second position without engagement by the locking mechanism so as to lessen resistance to the movement; and
a coupling mechanism operating between the dilator and the guidewire, the coupling mechanism comprising a T-shaped locking section disposed on the guidewire that interengages with the guidewire hub to form a reversible snap-fit grip.

24. The access device of claim 23, wherein the guidewire hub comprises two bendable tines that form a portion of the snap-fit grip.

25. The access device of claim 24, wherein the guidewire hub comprises an end recess in-line with a path between the tines.

26. An access device for placing a medical article within a body space, comprising:
a needle having an elongated needle body with a distal end and a hub from which the needle body extends, the elongated needle body comprising at least one needle side fenestration;
a dilator slideably disposed on the needle body, comprising a dilator hub and an elongated dilator shaft that extends from the dilator hub, wherein the dilator shaft comprises at least one dilator side fenestration in communication with the needle side fenestration and a raised ridge through which the dilator side fenestration passes, and wherein the dilator hub comprises a receiving portion;
a medical article comprising a tubular section and a hub, the tubular section being disposed on the dilator and defining a space between the medical article and the dilator in communication with the needle side fenestration through the dilator side fenestration, wherein at a least portion of the medical article is configured to allow visual determination of the presence of a body fluid within the space; and
an insert disposed within the dilator receiving portion, the insert comprising a through-hole configured to receive the needle body therethrough, the through-hole being slightly larger than the needle body so as to form a passage between the insert and the needle body that allows gases to pass through the passage and to the atmosphere but hinders the passage of a body fluid.

27. The access device of claim 26, wherein the ridge is oriented in a generally axial direction.

28. The access device of claim 26, wherein the ridge is narrower than the dilator side fenestration.

29. An access device for placing a medical article within a body space, comprising:
a needle having an elongated needle body with a distal end and a hub from which the needle body extends, the elongated needle body comprising at least one side fenestration;
a dilator slideably disposed on the needle body, comprising a dilator hub and an elongated dilator shaft that extends from the dilator hub to a distal end, wherein the dilator shaft comprises at least one side fenestration in communication with the needle side fenestration, wherein the dilator distal end tapers at approximately 30 degrees, and wherein the dilator hub comprises a receiving portion;
a medical article comprising a tubular section and a hub, the tubular section being disposed on the dilator and defining a space between the medical article and the dilator in communication with the needle side fenestration through the dilator side fenestration, wherein at a least portion of the medical article is configured to allow visual determination of the presence of a body fluid within the space; and
an insert disposed within the dilator receiving portion, the insert comprising a through-hole configured to receive the needle body therethrough, the through-hole being slightly larger than the needle body so as to form a passage between the insert and the needle body that allows gases to pass through the passage and to the atmosphere but hinders the passage of a body fluid.

30. The access device of claim 29, wherein the dilator has a secondary taper at approximately 3 degrees proximal from the 30 degree taper.

\* \* \* \* \*

UNITED STATES PATENT AND TRADEMARK OFFICE
CERTIFICATE OF CORRECTION

PATENT NO.         : 8,956,327 B2                                    Page 1 of 1
APPLICATION NO.    : 13/577653
DATED              : February 17, 2015
INVENTOR(S)        : Steven F. Bierman It is certified that error appears in the above-identified patent and that said Letters Patent is hereby corrected as shown below:

In the specification

In column 5 at line 64, Change "dilator" to --dilator.--.

In column 6 at line 29 (approx.), Change "enlargerd" to --enlarged--.

In column 6 at line 52, Change "22A" to --22A.--.

In column 17 at line 21, Change "bodily" to --body--.

In column 19 at line 31, Change "bodily" to --body--.

In column 23 at line 35, Change "bodily" to --body--.

In column 33 at line 9, Change "pneumotorax," to --pneumothorax,--.

In the claims

In column 33 at lines 59-60, In Claim 1, change "at a least" to --at least a--.

In column 34 at line 30, In Claim 10, change "bodily" to --body--.

In column 36 at lines 24-25, In Claim 26, change "at a least" to --at least a--.

In column 36 at lines 57-58, In Claim 29, change "at a least" to --at least a--.

Signed and Sealed this
Twenty-seventh Day of October, 2015

Michelle K. Lee
*Director of the United States Patent and Trademark Office*